(12) United States Patent
Whittamore et al.

(10) Patent No.: US 7,122,567 B2
(45) Date of Patent: Oct. 17, 2006

(54) HETEROCYCLIC AMIDE DERIVATIVES HAVING GLYCOGEN PHOSPHORYLASE INHIBITORY ACTIVITY

(75) Inventors: Paul Whittamore, Cheshire (GB); Stuart Norman Lile Bennett, Cheshire (GB); Iain Simpson, Cheshire (GB)

(73) Assignee: AstraZeneca AB, Södertälje (SE)

( * ) Notice: Subject to any disclaimer, the term of this patent is extended or adjusted under 35 U.S.C. 154(b) by 48 days.

(21) Appl. No.: 10/506,746

(22) PCT Filed: Mar. 4, 2003

(86) PCT No.: PCT/GB03/00875

§ 371 (c)(1),
(2), (4) Date: Sep. 3, 2004

(87) PCT Pub. No.: WO03/074531

PCT Pub. Date: Sep. 12, 2003

(65) Prior Publication Data

US 2005/0131052 A1 Jun. 16, 2005

(30) Foreign Application Priority Data

Mar. 6, 2002 (GB) .................... 0205170.4

(51) Int. Cl.
- A61K 31/40 (2006.01)
- A61K 31/415 (2006.01)
- C07D 235/02 (2006.01)
- C07D 409/00 (2006.01)

(52) U.S. Cl. .............. 514/393; 514/412; 544/358; 548/303.7; 548/454

(58) Field of Classification Search ............... 514/393, 514/412; 548/303.7, 453
See application file for complete search history.

(56) References Cited

U.S. PATENT DOCUMENTS

| | | | |
|---|---|---|---|
| 3,706,810 A | 12/1972 | Cyanamid | |
| 4,599,198 A | 7/1986 | Hoover | |
| 4,668,769 A | 5/1987 | Hoover | |
| 4,720,503 A | 1/1988 | Witzel | |
| 4,751,231 A | 6/1988 | Halczenko | |
| 4,786,641 A | 11/1988 | Goldmann | |
| 4,794,120 A | 12/1988 | Manoury | |
| 5,863,903 A | 1/1999 | Lundgren | |
| 5,998,463 A * | 12/1999 | Hulin et al. ............... | 514/418 |
| 2004/0002495 A1 | 1/2004 | Sher | |
| 2004/0142938 A1 | 7/2004 | Sher et al. | |
| 2004/0220229 A1 | 11/2004 | Bussolotti et al. | |
| 2004/0266768 A1 | 12/2004 | Schoenafinger et al. | |

FOREIGN PATENT DOCUMENTS

| | | |
|---|---|---|
| DE | 200740 | 6/1983 |
| DE | 4445968 | 6/1996 |
| EP | 697403 | 2/1996 |
| EP | 0846464 | 6/1998 |
| EP | 0884050 | 12/1998 |
| EP | 0978279 | 2/2000 |
| EP | 1149580 | 2/2001 |
| EP | 1177791 | 7/2001 |
| EP | 1125580 | 8/2001 |
| EP | 1134213 | 9/2001 |
| EP | 1136071 | 9/2001 |

(Continued)

OTHER PUBLICATIONS

U.S. Appl. No. 10/344,506, by Whittamore et al.*

(Continued)

*Primary Examiner*—Kamal A. Saeed
*Assistant Examiner*—Susannah L. Chung

(57) ABSTRACT

Heterocyclic amides of formula (1)

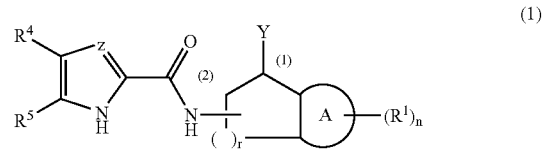

wherein:
Z is CH or nitrogen;
$R^4$ and $R^5$ together are either —S—C($R^6$)=C($R^7$)— or —C($R^7$)=C($R^6$)—S—;
$R^6$ and $R^7$ are selected from for example hydrogen, halo, $C_{1-4}$alkyl, and $C_{1-4}$alkanoyl;
A is phenylene or heteroarylene;
n is 0, 1 or 2;
$R^1$ is selected from for example halo, nitro, cyano, hydroxy, carboxy;
r is 1 or 2;
Y is —$NR^2R^3$ or —$OR^3$;
$R^2$ and $R^3$ are selected from for example hydrogen, hydroxy, aryl, heterocyclyl and $C_{1-4}$alkyl(optionally substituted by 1 or 2 $R^8$ groups);
$R^4$ is selected from for example hydrogen, halo, nitro, cyano, hydroxy, $C_{1-4}$alkyl, and $C_{1-4}$alkanoyl;
$R^8$ is selected from for example hydroxy, —$COCOOR^9$, —C(O)N($R^9$)($R^{10}$), —NHC(O)$R^9$, ($R^9$)($R^{10}$)N— and —$COOR^9$;
$R^9$ and $R^{10}$ are selected from for example hydrogen, hydroxy, $C_{1-4}$alkyl (optionally substituted by 1 or 2 $R^{13}$);
$R^{13}$ is selected from hydroxy, halo, trihalomethyl and $C_{1-4}$alkoxy;
or a pharmaceutically acceptable salt or pro-drug thereof; possess glycogen phosphorylase inhibitory activity and accordingly have value in the treatment of disease states associated with increased glycogen phosphorylase activity. Processes for the manufacture of said heterocyclic amide derivatives and pharmaceutical compositions containing them are described.

16 Claims, No Drawings

FOREIGN PATENT DOCUMENTS

| | | |
|---|---|---|
| EP | 1 338 594 A1 | 8/2003 |
| EP | 1 340 500 A1 | 9/2003 |
| EP | 1088824 | 1/2004 |
| EP | 1145717 | 5/2004 |
| ES | 2081747 | 3/1996 |
| JP | 021247565 | 5/1990 |
| JP | 04179949 | 6/1992 |
| JP | 2001 089368 | 4/2001 |
| JP | 2001 206856 | 7/2001 |
| JP | 2001247565 A | 9/2001 |
| JP | 2004196702 A | 7/2004 |
| WO | WO-93/25574 | 12/1993 |
| WO | WO-95/24391 | 9/1995 |
| WO | WO-96/39384 | 12/1996 |
| WO | WO-96/39385 | 12/1996 |
| WO | WO-97/09040 | 3/1997 |
| WO | WO-97/31901 | 9/1997 |
| WO | WO-97/45425 | 12/1997 |
| WO | WO-98/27108 | 6/1998 |
| WO | WO-98/40353 | 9/1998 |
| WO | WO-98/50359 | 11/1998 |
| WO | WO-99/26659 | 6/1999 |
| WO | WO-99/36393 | 7/1999 |
| WO | WO-00/42213 | 7/2000 |
| WO | WO-00/47206 | 8/2000 |
| WO | WO-01/05954 | 1/2001 |
| WO | WO-01/23347 | 4/2001 |
| WO | 01/32622 A1 | 5/2001 |
| WO | WO-01/32654 | 5/2001 |
| WO | WO-01/52825 | 7/2001 |
| WO | WO-01/68055 | 9/2001 |
| WO | WO-01/68092 | 9/2001 |
| WO | WO-01/68603 | 9/2001 |
| WO | WO-01/94300 | 12/2001 |
| WO | WO-01/96311 | 12/2001 |
| WO | WO-01/96347 | 12/2001 |
| WO | 02/20530 A1 | 3/2002 |
| WO | WO-02/26714 | 4/2002 |
| WO | WO-02/34718 | 5/2002 |
| WO | WO-02/080844 | 10/2002 |
| WO | WO-02/096864 | 12/2002 |
| WO | WO-02/098348 | 12/2002 |
| WO | WO-03/037864 | 5/2003 |
| WO | 03/045920 A1 | 6/2003 |
| WO | 03/072570 A1 | 9/2003 |
| WO | 03/074484 A1 | 9/2003 |
| WO | 03/074485 A2 | 9/2003 |
| WO | 03/074513 A2 | 9/2003 |
| WO | 03/074517 A1 | 9/2003 |
| WO | 03/074532 A1 | 9/2003 |
| WO | 03/091213 A1 | 11/2003 |
| WO | 2004/031193 A1 | 4/2004 |
| WO | 2004/031194 A1 | 4/2004 |
| WO | 2004/041780 A2 | 5/2004 |
| WO | 2004/092158 A1 | 10/2004 |
| WO | 2004/113345 A1 | 12/2004 |
| WO | 2005/013975 A1 | 2/2005 |
| WO | 2005/013981 A1 | 2/2005 |
| WO | 2005/018637 A1 | 3/2005 |
| WO | 2005/019172 A1 | 3/2005 |
| WO | 2005/020985 A1 | 3/2005 |
| WO | 2005/020986 A1 | 3/2005 |
| WO | 2005/020987 A1 | 3/2005 |

OTHER PUBLICATIONS

Clore & Blackgard (1994), Diabetes 43: 256-262.*
DeFronzo, R.A. et al, (1992) Diabetes Care 15; 318-355.*
Reaven, G.M. (1995) Diabetologia 38:3-13.*

Birch, A., et al., "Novel Thienopyrrole Glycogen Phosphorylase inhibitors: In Vitro SAR and Crystallographic Studies," Poster, AstraZeneca UK, CVGI Research, Mereside, Alderley Park, Macclesfield, Cheshire.

Crochet, R.A., et al., "Synthesis of Substituted Thieno[2,3-b] pyrroles," vol. 11, 143-150 (Apr. 1974).

Freeman, S., et al., "Effect of Glucose on Rat and Human Liver Glycogen Phosphorylasea Activity and Potency of a Glycogen Phosphoylase Inhibitor," Diabetes, 52, Supp., 1470-P, A340.

Hartman, G.D., et al., "The Synthesis of 5-Alkylaminomethylthieno[2,3-b]Pyrrole-5-Sulfonamides," Heterocycles, 29(10):1943-1949 (1989).

Hoover, D.J., et al., "Indole-2-carboxamide Inhibitors of Human Liver Glycogen Phosphorylase," J. Med. Chem., 41:2934-2938 (1998).

Hudson, S., et al., "The effect of a glycogen phosphorylase inhibitor upon muscle fatigue in anaesthetised rats," J. Physiol., 539:52-53 (2002).

Jakobsen, P., et al., "Iminosugars: Potential Inhibitors of Liver Glycogen Phosphorylase.," Bioorganic Med. Chem., 9:733-744 (2001).

Martin, W.H., et al., "Discovery of a human liver glycogen phosphorylase inhibitor that lowers blood glucose in vivo," PNAS, 95:1776-1781 (Feb. 1998).

McCormack, J.G., et al., "Pharmacological Approaches to Inhibit Endogenous Glucose Production as a Means of Anti-diabetic Therapy," Curr. Pharmaceutical Design, 7:1451-1474 (2001).

Oikonomakos, N.G., et al., "Allosteric inhibition of glycogen phosphorylase alpha by the potential antidiabetic drug 3-isopropyl 4-(2-chlorophenyl)-1,4-dihydro-1-ethyl-2-methyl-pyridine-3,5,6-tricarboxylate," Protein Sci., 8:1930-1945 (1999).

Rath, V.L. et al., "Activation of Human Liver Glycogen Phosphorylase by Alteration of the Secondary Structure and Packing of the Catalytic Core," Mol. Cell, 6:139-148 (Jul. 2000).

Rosauer, K.G., et al., "Novel, 3,4-Dihydroquinolin-2(1H)-one Inhibitors of Human Glycogen Phosphorylase a," Bioorganic & Medicinal Chemistry Letters, 13:4385-4388 (2003).

Soman, G., et al. "Aromatic Compounds as Allosteric Inhibitors of Glycogen Phosphorylase beta," biochimica et Biophysica Acta, 358:359-362 (1974).

Soman, G., et al., "The Nature of the Binding Site for Aromatic Compounds in Glycogen Phosphorylase beta," Biochem. J., 147:369-371 (1975).

Teague, J., "Mobilisation of Tissue Glycogen Following Inhibition of Glycogen Phosphorylase in fa/fa Rat," Diabetes, 53, Supp. 1, A365, 1521-P.

Treadway, J.L., et al., "Glycogen phosphorlase inhibitors for treatment of type 2 diabetes mellitus," Exp. Opin. Invest. Drugs, 10(2):439-454 (2001).

Turnbull, A., et al., "Pharmacological Inhibition of Glycogen Phosphorylase (GP) Lowers Plasma Glucose in Rat Models of Type 2 Diabetes," Dibetes, 52, Supp., 1485-P, A343.

Venkatarangan, P., et al., "Prediction of Ligand-REceptor Binding Thermodynamics by Free Energy Force Field Three-Dimensional Quantitative Structure-Activity Relationship Analysis: Applications to a Set of Glucose Analogue Inhibitors of Glycogen Phosphorylase," J. Med. Chem., 42:2169-2179 (1999).

Vertigan, H., "impact of cell glycogen content on modulation of hepatocyte glucose metabolism by pharmacological agents," Diabetes, 47, Supp., 589, A214.

Font, M. et al. "Indoles and pyridazino[4,5-b]indoles as nonucleoside analog inhibitors of HIV-1 reverse transcripptase", European Journal Med Chem (1995), 30(12), 963-71.

Vertigan, H. et al. "Impact of cell glycogen content on modulation of hepatocyte glucose metabolism by pharmacological agents", EASD Munich(2004).

Bartlett, J. et al. "In Vitro and In Vivo Profile of Gpi688, a Novel, Potent Inhibitor of Glycogen Phosphorylase", ADA San Diego(2005).

Green, A R. et al. "The Glycogenic Action of Protein Targeting to Glycogen in Hepatocytes Involves Multiple Mechanisms Including Phosphorylase Inactivation and Glycogen Synthase Translocation", J Biol Chem, 279(45), 46474-46482,(2004).

Roberts, P A. et al. "The temporal relationship between glycogen phosphorylase and activation of the pyruvate dehydrogenase complex during adrenaline infusion in resting canine skeletal muscle", J Physiology-London 545(1), 297-304,(2002).

Simpson, I. et al. "Novel Orally Active Amino-indan Inhibitors of Glycogen Phosphorylase", Cambridge Med Chem Conference,(Sep. 2005) Poster EOM.

Crochet, R.A., et al., J. Het. Chem., "Synthesis of Substituted Thieno[2,3-b] pyrroles," vol. 11, 143-150 (Apr. 1974).

Teague, J., "Mobilisation of Tissue Glycogen Following Inhibition of Glycogen Phosphorylase in fa/fa Rat," Diabetes, 52, Supp. 2, A365, 1521-P (2003).

Vertigan, H., "Impact of cell glycogen content on modulation of hepatocyte glucose metabolism by pharmacological agents," Diabetologia, 47, Supp. 1, 589, A214, (2004).

* cited by examiner

HETEROCYCLIC AMIDE DERIVATIVES HAVING GLYCOGEN PHOSPHORYLASE INHIBITORY ACTIVITY

This application is a national stage filing under 35 U.S.C. 371 of International Application No. PCT/GB03/00875, filed Mar. 4, 2003, which claims priority from United Kingdom Patent Application No. 0205170.4, filed Mar. 6, 2002, the specification of which is incorporated by reference herein. International Application No. PCT/GB03/00875 was published under PCT Article 21(2) in English.

The present invention relates to heterocyclic amide derivatives, pharmaceutically acceptable salts and in vivo hydrolysable esters thereof. These heterocyclic amides possess glycogen phosphorylase inhibitory activity and accordingly have value in the treatment of disease states associated with increased glycogen phosphorylase activity and thus are potentially useful in methods of treatment of a warm-blooded animal such as man. The invention also relates to processes for the manufacture of said heterocyclic amide derivatives, to pharmaceutical compositions containing them and to their use in the manufacture of medicaments to inhibit glycogen phosphorylase activity in a warm-blooded animal such as man.

The liver is the major organ regulating glycaemia in the post-absorptive state. Additionally, although having a smaller role in the contribution to post-prandial blood glucose levels, the response of the liver to exogenous sources of plasma glucose is key to an ability to maintain euglycaemia. An increased hepatic glucose output (HGO) is considered to play an important role in maintaining the elevated fasting plasma glucose (FPG) levels seen in type 2 diabetics; particularly those with a FPG>140 mg/dl (7.8 mM). (Weyer et al, (1999), J Clin Invest 104: 787–794; Clore & Blackgard (1994), Diabetes 43: 256–262; De Fronzo, R. A., et al, (1992) Diabetes Care 15; 318–355; Reaven, G. M. (1995) Diabetologia 38; 3–13).

Since current oral, anti-diabetic therapies fail to bring FPG levels to within the normal, non-diabetic range and since raised FPG (and glycHbA1c) levels are risk factors for both macro- (Charles, M. A. et al (1996) Lancet 348, 1657–1658; Coutinho, M. et al (1999) Diabetes Care 22; 233–240; Shaw, J. E. et al (2000) Diabetes Care 23, 34–39) and micro-vascular disease (DCCT Research Group (1993) New. Eng. J. Med. 329; 977–986); the reduction and normalisation of elevated FPG levels remains a treatment goal in type 2 DM.

It has been estimated that, after an overnight fast, 74% of HGO was derived from glycogenolysis with the remainder derived from gluconeogenic precursors (Hellerstein et al (1997) Am J Physiol, 272: E163). Glycogen phosphorylase is a key enzyme in the generation by glycogenolysis of glucose-1-phosphate, and hence glucose in liver and also in other tissues such as muscle and neuronal tissue.

Liver glycogen phosphorylase a activity is elevated in diabetic animal models including the db/db mouse and the fa/fa rat (Aiston S et al (2000). Diabetalogia 43, 589–597).

Inhibition of hepatic glycogen phosphorylase with chloroindole inhibitors (CP91149 and CP320626) has been shown to reduce both glucagon stimulated glycogenolysis and glucose output in hepatocytes (Hoover et al (1998) J Med Chem 41, 2934–8; Martin et al (1998) PNAS 95, 1776–81). Additionally, plasma glucose concentration is reduced, in a dose related manner, db/db and ob/ob mice following treatment with these compounds.

Studies in conscious dogs with glucagon challenge in the absence and presence of another glycogen phosphorylase inhibitor, Bay K 3401, also show the potential utility of such agents where there is elevated circulating levels of glucagon, as in both Type 1 and Type 2 diabetes. In the presence of Bay R 3401, hepatic glucose output and arterial plasma glucose following a glucagon challenge were reduced significantly (Shiota et al, (1997), Am J Physiol, 273: E868).

The heterocyclic amides of the present invention possess glycogen phosphorylase inhibitory activity and accordingly are expected to be of use in the treatment of type 2 diabetes, insulin resistance, syndrome X, hyperinsulinaemia, hyperglucagonaemia, cardiac ischaemia and obesity, particularly type 2 diabetes.

According to one aspect of the present invention there is provided a compound of formula (1):

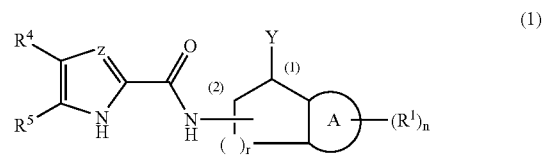

wherein:

Z is CH or nitrogen;

$R^4$ and $R^5$ together are either —S—C($R^6$)=C($R^7$)— or —C($R^7$)=C($R^6$)—S—;

$R^6$ and $R^7$ are independently selected from hydrogen, halo, nitro, cyano, hydroxy, fluoromethyl, difluoromethyl, trifluoromethyl, trifluoromethoxy, carboxy, carbamoyl, $C_{1-4}$alkyl, $C_{2-4}$alkenyl, $C_{2-4}$alkynyl, $C_{1-4}$alkoxy and $C_{1-4}$alkanoyl;

A is phenylene or heteroarylene;

n is 0, 1 or 2;

$R^1$ is independently selected from halo, nitro, cyano, hydroxy, carboxy, carbamoyl, N—$C_{1-4}$alkylcarbamoyl, N,N—($C_{1-4}$alkyl)$_2$carbamoyl, sulphamoyl, N—$C_{1-4}$alkylsulphamoyl, N,N—($C_{1-4}$alkyl)$_2$sulphamoyl, —S(O)$_b$$C_{1-4}$alkyl (wherein b is 0, 1, or 2), $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, hydroxy$C_{1-4}$alkyl, fluoromethyl, difluoromethyl, trifluoromethyl and trifluoromethoxy;

or, when n is 2, the two $R^1$ groups, together with the carbon atoms of A to which they are attached, may form a 4 to 7 membered ring, optionally containing 1 or 2 heteroatoms independently selected from O, S and N, and optionally being substituted by one or two methyl groups;

r is 1 or 2; and when r is 1 the group

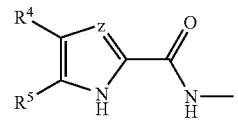

is a substituent on carbon (2) and when r is 2 (hereby forming a six membered ring) the same group is a substituent on carbon (2) or on carbon (3);

Y is —NR$^2$R$^3$ or —OR$^3$;

R$^2$ and R$^3$ are independently selected from hydrogen, hydroxy, C$_{1-4}$alkoxy, C$_{1-4}$alkanoyl, carbamoyl, C$_{3-7}$cycloalkyl (optionally substituted with 1 or 2 hydroxy groups), cyano(C$_{1-4}$)alkyl, heterocyclyl, aryl, C$_{1-4}$alkyl [optionally substituted by 1 or 2 R$^8$ groups], —COR$^8$, —SO$_b$R$^8$ (wherein b is 0, 1 or 2) and groups of the formulae B and B':

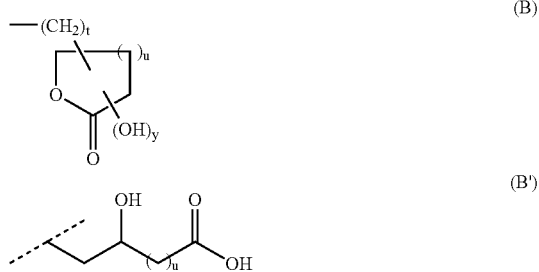

wherein y is 0 or 1, t is 0, 1, 2 or 3 and u is 1 or 2; provided that the hydroxy group is not a substituent on the ring carbon adjacent to the ring oxygen; or wherein NR$^2$R$^3$ may form a 4 to 7 membered saturated, partially saturated or unsaturated ring, optionally containing 1, 2 or 3 additional heteroatoms independently selected from N, O and S, wherein any —CH$_2$— may optionally be replaced by —C(=O)—, and any N or S atom may optionally be oxidised to form an N-oxide or SO or SO$_2$ group respectively, and wherein the ring is optionally substituted by 1 or 2 substituents independently selected from halo, cyano, C$_{1-4}$alkyl, hydroxy, C$_{1-4}$alkoxy and C$_{1-4}$alkylS(O)$_b$— (wherein b is 0, 1 or 2);

R$^8$ is independently selected from hydrogen, hydroxy, C$_{1-4}$alkyl, C$_{2-4}$alkenyl, C$_{1-4}$alkoxy, cyano(C$_{1-4}$)alkyl, amino(C$_{1-4}$)alkyl [optionally substituted on nitrogen by 1 or 2 groups selected from C$_{1-4}$alkyl, hydroxy, hydroxy(C$_{1-4}$)alkyl, dihydroxy(C$_{1-4}$)alkyl, —CO$_2$C$_{1-4}$alkyl, aryl and aryl(C$_{1-4}$)alkyl], halo(C$_{1-4}$)alkyl, dihalo(C$_{1-4}$)alkyl, trihalo(C$_{1-4}$)alkyl, hydroxy(C$_{1-4}$)alkyl, dihydroxy(C$_{1-4}$)alkyl, C$_{1-4}$alkoxyC$_{1-4}$alkoxy, C$_{1-4}$alkoxyC$_{1-4}$alkyl, hydroxyC$_{1-4}$alkoxy, 5- and 6-membered cyclic acetals and mono- and di-methyl derivatives thereof, aryl, heterocyclyl, (heterocyclyl)C$_{1-4}$alkyl, C$_{3-7}$cycloalkyl (optionally substituted with 1 or 2 hydroxy groups, C$_{1-4}$alkyl or —C(O)OC$_{1-4}$alkyl), C$_{1-4}$alkanoyl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), C$_{1-4}$alkylS(O)$_c$(C$_{1-4}$)alkyl (wherein c is 0, 1 or 2), —N(OH)CHO, —C(=N—OH)NH$_2$, —C(=N—OH)NHC$_{1-4}$alkyl, —C(=N—OH)N(C$_{1-4}$alkyl)$_2$, —C(=N—OH)NHC$_{3-6}$cycloalkyl, —C(=N—OH)N(C$_{3-6}$cycloalkyl)$_2$, —COCOOR$^9$, —C(O)N(R$^9$)(R$^{10}$), —NHC(O)R$^9$, —C(O)NHSO$_2$(C$_{1-4}$alkyl), —NHSO$_2$R$^9$, (R$^9$)(R$^{10}$)NSO$_2$—, —COCH$_2$OR$^{11}$, (R$^9$)(R$^{10}$)N— and —COOR$^9$, —CH$_2$OR$^9$, —CH$_2$COOR$^9$, —CH$_2$OCOR$^9$, —CH$_2$CH(CO$_2$R$^9$)OH, —CH$_2$C(O)NR$^9$R$^{10}$, —(CH$_2$)$_w$CH(NR$^9$R$^{10}$)CO$_2$R$^{9'}$ (wherein w is 1, 2 or 3), and —(CH$_2$)$_w$CH(NR$^9$R$^{10}$)CO(NR$^9$R$^{10'}$) (wherein w is 1, 2 or 3);

R$^9$, R$^{9'}$, R$^{10}$ and R$^{10'}$ are independently selected from hydrogen, hydroxy, C$_{1-4}$alkyl (optionally substituted by 1 or 2 R$^{13}$), C$_{2-4}$alkenyl, C$_{3-7}$cycloalkyl (optionally substituted by 1 or 2 hydroxy groups), cyano(C$_{1-4}$)alkyl, trihaloalkyl, aryl, heterocyclyl, heterocyclyl(C$_{1-4}$alkyl), and —C(=O)O(C$_4$)alkyl; or R$^9$ and R$^{10}$ together with the nitrogen to which they are attached, and/or R$^{9'}$ and R$^{10'}$ together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl, C$_{1-4}$alkoxy and heterocyclyl; or the ring may be optionally substituted on two adjacent carbons by —O—CH$_2$—O— to form a cyclic acetal wherein one or both of the hydrogens of the —O—CH$_2$—O— group may be replaced by a methyl;

R$^{13}$ is selected from halo, trihalomethyl, and C$_{1-4}$alkoxy;

R$^{11}$ is independently selected from hydrogen, C$_{1-4}$alkyl, and hydroxyC$_{1-4}$alkyl;

or a pharmaceutically acceptable salt or pro-drug thereof;

with the proviso that the compound of formula (1) is not:
i) 2,3-dichloro-5-(N-{1-[N-(1,1-dimethylethoxy)carbonylamino]indan-2-yl}carbamoyl)-4H-thieno[3,2-b]pyrrole;
ii) 5-[N-(1-aminoindan-2-yl)carbamoyl]-2,3-dichloro-4-H-thieno[3,2-b]pyyrrole;
iii) 5-[N-(1-acetamidoindan-2-yl)carbamoyl]-2,3-dichloro-4H-thieno[3,2-b]pyrrole;
iv) 2,3-dichloro-5-{N-[1-(methanesulphonamido)indan-2-yl]carbamoyl}-4H-thienol[3,2-b]pyrrole;
v) 2,3-dichloro-5-{N-[1-(methylamino)indan-2-yl]carbamoyl}-4H-thieno[3,2-b]pyrrole;
vi) 2,3-dichloro-5-{N-[1-(methylacetamido)indan-2-yl]carbamoyl}-4H-thieno[3,2-b]pyrrole;
vii) 2,3-dichloro-5-[N-(1-hydroxyindan-2-yl)carbamoyl]-4H-thieno[3,2-b]pyrrole;
viii) 2-chloro-5-[N-(1-hydroxyindan-2-yl)carbamoyl]-6H-thieno[2,3-b]pyrrole;
ix) 2,3-dichloro-5-[N-(6-fluoro-1-hydroxyindan-2-yl)carbamoyl]-4H-thieno[3,2-b]pyrrole;
x) 2,3-dichloro-5-[N-(1-methoxyindan-2-yl)carbamoyl]-4H-thieno[3,2-b]pyrrole;
xi) 2,3-dichloro-5-[N-(1-hydroxy-1,2,3,4-tetrahydronaphth-2-yl)carbamoyl]-4H-thieno[3,2-b]pyrrole.

According to another aspect of the present invention there is provided a compound of formula (1):

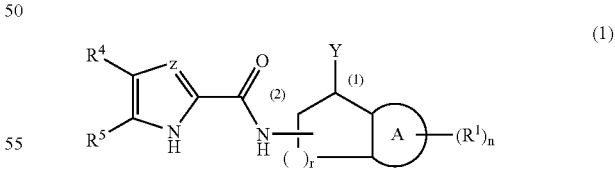

wherein:

Z is CH or nitrogen;

R$^4$ and R$^5$ together are either —S—C(R$^6$)=C(R$^7$)— or —C(R$^7$)=C(R$^6$)—S—;

R$^6$ and R$^7$ are independently selected from hydrogen, halo, nitro, cyano, hydroxy, fluoromethyl, difluoromethyl, trifluoromethyl, trifluoromethoxy, amino, carboxy, carbamoyl, mercapto, sulfamoyl, ureido, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N—(C$_{1-6}$alkyl)amino, N,N—(C$_{1-6}$alkyl)$_2$amino, C$_{1-6}$alkanoylamino, N—(C$_{1-6}$alkyl)carbamoyl, N,N—(C$_{1-6}$alkyl)$_2$carbamoyl, C$_{1-6}$alkylS(O)$_a$ wherein a is 0 to 2, C$_{1-6}$alkoxycarbonyl, C$_{1-6}$alkoxycarbonylamino, N-(C$_{1-6}$alkyl)sulphamoyl, N,N—(C$_{1-6}$alkyl)$_2$sulphamoyl, C$_{1-6}$alkylsulphonylamino and C$_{1-6}$alkylsulphonyl-N—(C$_{1-6}$alkyl)amino;

A is phenylene or heteroarylene;

n is 0, 1 or 2;

R$^1$ is independently selected from hydrogen, halo, nitro, cyano, hydroxy, amino, carboxy, carbamoyl, N—C$_{1-4}$alkylcarbamoyl, N,N—(C$_{1-4}$alkyl)$_2$carbamoyl, sulphamoyl, N—C$_{1-4}$alkylsulphamoyl, N,N—(C$_{1-4}$alkyl)$_2$sulphamoyl, sulfino, sulfo, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$alkyl)amino, N,N—(C$_{1-4}$alkyl)$_2$amino, hydroxyC$_{1-4}$alkyl, fluoromethyl, difluoromethyl, trifluoromethyl, trifluoromethoxy, C$_{1-4}$alkoxy and R$^1$ is of the formula A' or A":

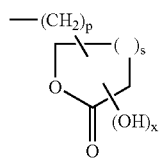

(A)

—CH$_2$CH(OH)(CH$_2$)$_u$CO$_2$H   (A')

wherein x is 0 or 1, p is 0, 1, 2 or 3 and s is 1 or 2; provided that the hydroxy group is not a substituent on the ring carbon adjacent to the ring oxygen;

r is 1 or 2; and when r is 1 the group

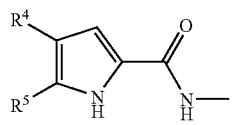

is a substituent on carbon (2) and when r is 2 (hereby forming a six membered ring) the same group is a substituent on carbon (2) or on carbon (3);

Y is —NR$^2$R$^3$ or —OR$^3$;

R$^2$ and R$^3$ are independently selected from hydrogen, hydroxy, C$_{1-4}$alkyl (substituted by 1 or 2 hydroxy groups provided that when there are 2 hydroxy groups they are not substituents on the same carbon), C$_{5-7}$cycloalkyl (optionally substituted with 1 or 2 hydroxy groups provided that when there are 2 hydroxy groups they are not substituents on the same carbon), cyano(C$_{1-4}$)alkyl, 4-butanolidyl, 5-pentanolidyl, tetrahydrothiopyranyl, 1-oxotetrahydrothiopyranyl group, 1,1-dioxotetrahydrothiopyranyl, fluoromethylcarbonyl, difluoromethylcarbonyl, trifluoromethylcarbonyl, C$_{1-4}$alkyl [substituted by 1 or 2 R$^8$ groups (provided that when there are 2 R$^8$ groups they are not substituents on the same carbon)], —COR$^8$, —SO$^b$R$^8$ (wherein b is 0, 1 or 2) and groups of the formulae B and B':

(B)

—CH$_2$CH(OH)(CH$_2$)$_u$CO$_2$H   (B')

wherein y is 0 or 1, t is 0, 1, 2 or 3 and u is 1 or 2; provided that the hydroxy group is not a substituent on the ring carbon adjacent to the ring oxygen);

{wherein R$^8$ is independently selected from hydrogen, hydroxy, C$_{1-4}$alkoxyC$_{1-4}$alkoxy, hydroxyC$_{1-4}$alkoxy, 2,2-dimethyl-1,3-dioxolan-4-yl, heterocyclyl (optionally substituted on carbon or nitrogen by 1 or 2 groups selected from hydrogen, nitro, halo, cyano, hydroxy and C$_{1-4}$alkyl), (heterocyclyl)C$_{1-4}$alkyl (wherein the heterocyclyl is optionally substituted on carbon or nitrogen by 1 or 2 groups selected from hydrogen, nitro, halo, cyano, hydroxy and C$_{1-4}$alkyl), aryl (optionally substituted by 1 or 2 groups selected from nitro, halo, cyano, hydroxy and C$_{1-4}$alkyl), C$_{1-4}$alkyl, C$_{2-4}$alkenyl, cyclo(C$_{3-8}$)alkyl, C$_{1-4}$alkoxy, cyano(C$_{1-4}$)alkyl, amino(C$_{1-4}$)alkyl (optionally substituted on nitrogen by 1 or 2 groups selected from hydrogen, C$_{1-4}$alkyl, hydroxy, hydroxy(C$_{1-4}$)alkyl, dihydroxy(C$_{1-4}$)alkyl, aryl and aryl (C$_{1-4}$)alkyl), C$_{1-4}$alkylS(O)$_c$(C$_{1-4}$) alkyl (wherein c is 0, 1 or 2), —N(OH)CHO, —CH$_2$CH(CO$_2$R$^9$)N(R$^9$R$^{10}$), —CH$_2$OR$^9$, (R$^9$)(R$^{10}$)N—, —COOR$^9$ and —CH$_2$COOR$^9$, —CH$_2$CONR$^9$R$^{10}$, —(CH$_2$)$_u$CH(NR$^9$R$^{10}$)CO$_2$R$^9$ (wherein u is 1, 2 or 3);

[wherein R$^9$ and R$^{10}$ are independently selected from hydrogen, hydroxy, C$_{1-4}$alkyl (optionally substituted by 1 or 2 hydroxy groups provided that when there are 2 hydroxy groups they are not substituents on the same carbon), C$_{5-7}$cycloalkyl (optionally substituted by 1 or 2 hydroxy groups provided that when there are 2 hydroxy groups they are not substituents on the same carbon), C$_{2-4}$alkenyl, cyano (C$_{1-4}$) alkyl, 4-butanolidyl, 5-pentanolidyl, tetrahydrothiopyranyl, 1-oxotetrahydrothiopyranyl group, 1,1-dioxotetrahydrothiopyranyl, 2,2-dimethyl-1,3-dioxolan-4-yl, aryl (optionally substituted by 1 or 2 substituents selected from hydrogen, nitro, halo, hydroxy and C$_{1-4}$alkyl) and C$_{1-4}$alkyl substituted by R$^{13}$;

(wherein R$^{13}$ is selected from hydroxy, C$_{1-4}$alkoxy, heterocyclyl, C$_{1-4}$alkanoyl, C$_{1-4}$alkylS(O)$_d$ (wherein d is 0, 1 or 2)1, —N(OH)CHO, (R$^{11}$)(R$^{12}$)NCO—, (R$^{11}$)(R$^{12}$)NSO$_2$—, —COCH$_2$OR$^{11}$ and (R$^{11}$)(R$^{12}$)N—;

{wherein R$^{11}$ and R$^{12}$ are independently selected from hydrogen, C$_{1-4}$alkyl, C$_{1-4}$alkoxy, hydroxyC$_{1-4}$alkyl, C$_{1-4}$alkylS(O)$_e$ (wherein e is 0, 1 or 2)}); and R$^9$ and R$^{10}$ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N—C$_{1-4}$alkylamino, N,N—(C$_{1-4}$)$_2$alkylamino, carbonyl, sulfo, C$_{1-4}$alkoxy, heterocyclyl, C$_{1-4}$alkanoyl, C$_{1-4}$alkylS(O)$_f$(C$_{1-4}$)alkyl (wherein f is 0, 1 or 2), —N(OH)CHO, (R$^{11}$)(R$^{12}$)NCO—, (R$^{11}$)(R$^{12}$) NSO$_2$—, —COCH$_2$OR$^{11}$, (R$^{11}$)(R$^{12}$)N—; wherein R$^{11}$ and R$^{12}$ are as defined above]};

provided that when R$^1$ is of the formula A' or A" then R$^2$ and R$^3$ do not contain a group of the formula B or B' and when $R^2$ or $R^3$ is of the formula B or B' then $R^1$ does not contain a group of the formula A' or A" such that a compound of formula (1) can contain only one of A', A", B and B';
or a pharmaceutically acceptable salt or in vivo hydrolysable ester thereof;

with the proviso that the compound of formula (1) is not:
i) 2,3-dichloro-5-(N-{1-[N-(1,1-dimethylethoxy)carbonylamino]indan-2-yl}carbamoyl)4H-thieno[3,2-b]pyrrole;
ii) 5-[N-(1-aminoindan-2-yl)carbamoyl]-2,3-dichloro-4H-thieno[3,2-b]pyrrole;
iii) 5-[N-(1-acetamidoindan-2-yl)carbamoyl]-2,3-dichloro-4H-thieno[3,2-b]pyrrole;
iv) 2,3-dichloro-5-{N-[1-(methanesulphonamido)indan-2-yl]carbamoyl}-4H-thieno[3,2-b]pyrrole;
v) 2,3-dichloro-5-{N-[1-(methylamino)indan-2-yl]carbamoyl}-4H-thieno[3,2-b]pyrrole;
vi) 2,3-dichloro-5-{N-[1-(methylacetamido)indan-2-yl]carbamoyl}4H-thieno[3,2-b]pyrrole;
vii) 2,3-dichloro-5-[N-(1-hydroxyindan-2-yl)carbamoyl]4H-thieno[3,2-b]pyrrole;
viii) 2-chloro-5-[N-(1-hydroxyindan-2-yl)carbamoyl]-6H-thieno[2,3-b]pyrrole;
ix) 2,3dichloro-5-[N-(6-fluoro-1-hydroxyindan-2-yl)carbamoyl]-4H-thieno[3,2-b]pyrrole;
x) 2,3-dichloro-5-[N-(1-methoxyindan-2-yl)carbamoyl]-4H-thieno[3,2-b]pyrrole;
xi) 2,3-dichloro-5-[N-(1-hydroxy-1,2,3,4-tetrahydronaphth-2-yl)carbamoyl]4H-thieno[3,2-b]pyrrole.

It is to be understood that when A is heteroarylene, the bridgehead atoms joining ring A to the piperidinone ring may be heteroatoms. Therefore, for example, the definition of

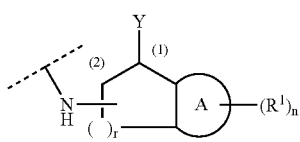

when A is heteroarylene encompasses the structures:

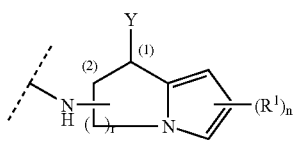

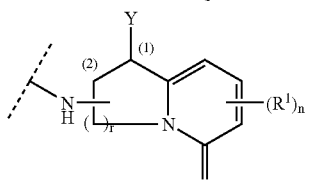

It is to be understood that, where optional substitution on alkyl or cycloalkyl groups in $R^3$, $R^9$ and $R^{10}$ (as defined hereinbefore or hereinafter) allows two hydroxy substituents on the alkyl or cycloalkyl group, or one hydroxy substituent and a second substituent linked by a heteroatom (for example alkoxy), then these two substituents are not substituents on the same carbon atom of the alkyl or cycloalkyl group.

In another aspect, the invention relates to compounds of formula (1) as hereinabove defined or to a pharmaceutically acceptable salt.

In another aspect, the invention relates to compounds of formula (1) as hereinabove defined or to a pro-drug thereof. Suitable examples of pro-drugs of compounds of formula (1) are in-vivo hydrolysable esters of compounds of formula (1). Therefore in another aspect, the invention relates to compounds of formula (1) as hereinabove defined or to an in-vivo hydrolysable ester thereof.

It is to be understood that, insofar as certain of the compounds of formula (1) defined above may exist in optically active or racemic forms by virtue of one or more asymmetric carbon atoms, the invention includes in its definition any such optically active or racemic form which possesses glycogen phosphorylase inhibition activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of the formula (1) or a salt thereof may exhibit the phenomenon of tautomerism and that the formulae drawings within this specification can represent only one of the possible tautomeric forms. It is to be understood that the invention encompasses any tautomeric form which has glycogen phosphorylase inhibition activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of the formula (1) and salts thereof can exist in solvated as well as unsolvated forms such as, for example, hydrated forms. It is to be understood that the invention encompasses all such solvated forms which have glycogen phosphorylase inhibition activity.

It is also to be understood that certain compounds of the formula (1) may exhibit polymorphism, and that the invention encompasses all such forms which possess glycogen phosphorylase inhibition activity.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula (1) are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

The compounds of the invention may be administered in the form of a pro-drug which is broken down in the human or animal body to give a compound of the invention. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the invention or a pharmaceutically-acceptable salt thereof.

Various forms of prodrugs are known in the art, for examples see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in vivo hydrolysable ester of a compound of formula (1) containing carboxy or hydroxy group is, for example. A pharmaceutically acceptable ester which is cleaved in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example acetyl; benzoyl; phenylacetyl; substituted benzoyl and phenylacetyl, $C_{1-10}$alkoxycarbonyl (to give alkyl carbonate esters), for example ethoxycarbonyl; di-$(C_{1-4})$alkylcarbamoyl and N-(di-$(C_{1-4})$alkylaminoethyl)-N-$(C_{1-4})$alkylcarbamoyl (to give carbamates); di-$(C_{1-4})$alkylaminoacetyl and carboxyacetyl. Examples of ring substituents on phenylacetyl and benzoyl include aminomethyl, $(C_{1-4})$alkylaminomethyl and di-$((C_{1-4})$alkyl)aminomethyl, and morpholino or piperazino linked from a ring nitrogen atom via a methylene linking group to the 3- or 4-position of the benzoyl ring. Other interesting in-vivo hyrolysable esters include, for example, $R^A C(O)O(C_{1-6})$alkyl-CO—, wherein $R^A$ is for example, benzyloxy-$(C_{1-4})$alkyl, or phenyl). Suitable substituents on a phenyl group in such esters include, for example, 4-$(C_{1-4})$piperazino-$(C_{1-4})$alkyl, piperazino-$(C_{1-4})$alkyl and morpholino-$(C_1-C_4)$alkyl.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "$C_{1-4}$alkyl" includes methyl, ethyl, propyl, isopropyl and t-butyl and examples of "$C_{1-6}$alkyl" include the examples of "$C_{1-4}$alkyl" and additionally pentyl, 2,3-dimethylpropyl, 3-methylbutyl and hexyl. An analogous convention applies to other generic terms, for example "$C_{2-4}$alkenyl" includes vinyl, allyl and 1-propenyl and examples of "$C_{2-6}$alkenyl" include the examples of "$C_{2-4}$alkenyl" and additionally 1-butenyl, 2-butenyl, 3-butenyl, 2-methylbut-2-enyl, 3-methylbut-1-enyl, 1-pentenyl, 3-pentenyl and 4-hexenyl. Examples of "$C_{2-4}$alkynyl" includes ethynyl, 1-propynyl and 2-propynyl and examples of "$C_{2-6}$alkynyl" include the examples of "$C_{2-4}$alkynyl" and additionally 3-butynyl, 2-pentynyl and 1-methylpent-2-ynyl.

The term "hydroxy$C_{1-4}$alkyl" includes hydroxymethyl, hydroxyethyl, hydroxypropyl, hydroxyisopropyl and hydroxybutyl. The term "hydroxyethyl" includes 1-hydroxyethyl and 2-hydroxyethyl. The term "hydroxypropyl" includes 1-hydroxypropyl, 2-hydroxypropyl and 3-hydroxypropyl and an analogous convention applies to terms such as hydroxybutyl. The term "dihydroxy$C_{1-4}$alkyl" includes dihydroxyethyl, dihydroxypropyl, dihydroxyisopropyl and dihydroxybutyl. The term "dihydroxypropyl" includes 1,2-dihydroxypropyl and 1,3-dihydroxypropyl. An analogous convention applies to terms such as dihydroxyisopropyl and dihydroxybutyl.

The term "halo" refers to fluoro, chloro, bromo and iodo. The term "dihalo$C_{1-4}$alkyl" includes difluoromethyl and dichloromethyl. The term "trihalo$C_{1-4}$alkyl" includes trifluoromethyl.

Examples of "5- and 6-membered cyclic acetals and mono- and di-methyl derivatives thereof" are:

1,3-dioxolan-4-yl, 2-methyl-1,3-dioxolan-4-yl, 2,2-dimethyl-1,3-dioxolan-4-yl; 2,2-dimethyl-1,3-dioxan-4-yl; 2,2-dimethyl-1,3-dioxan-5-yl; 1,3-dioxan-2-yl.

Examples of "$C_{1-4}$alkoxy" include methoxy, ethoxy, propoxy and isopropoxy. Examples of "$C_{1-6}$alkoxy" include the examples of "$C_{1-4}$alkoxy" and additionally butyloxy, t-butyloxy, pentoxy and 1,2-(methyl)$_2$propoxy. Examples of "$C_{1-4}$alkanoyl" include formyl, acetyl and propionyl. Examples of "$C_{1-6}$alkanoyl" include the example of "$C_{1-4}$alkanoyl" and additionally butanoyl, pentanoyl, hexanoyl and 1,2-(methyl)$_2$propionyl. Examples of "$C_{1-4}$alkanoyloxy" are formyloxy, acetoxy and propionoxy. Examples of "$C_{1-6}$alkanoyloxy" include the examples of "$C_{1-4}$alkanoyloxy" and additionally butanoyloxy, pentanoyloxy, hexanoyloxy and 1,2-(methyl)$_2$propionyloxy. Examples of "N—$(C_{1-4}$alkyl)amino" include methylamino and ethylamino. Examples of "N—$(C_{1-6}$alkyl)amino" include the examples of "N—$(C_{1-4}$alkyl)amino" and additionally pentylamino, hexylamino and 3-methylbutylamino. Examples of "N,N—$(C_{1-4}$alkyl)$_2$amino" include N—N-

(methyl)$_2$amino, N—N-(ethyl)$_2$amino and N-ethyl-N-methylamino. Examples of "N,N—(C$_{1-6}$alkyl)$_2$amino" include the example of "N,N—(C$_{1-4}$alkyl)$_2$amino" and additionally N-methyl-N-pentylamino and N,N-(pentyl)$_2$amino. Examples of "N—(C$_{1-4}$alkyl)carbamoyl" are methylcarbamoyl and ethylcarbamoyl. Examples of "N—(C$_{1-6}$alkyl) carbamoyl" are the examples of "N—(C$_{1-4}$alkyl)carbamoyl" and additionally pentylcarbamoyl, hexylcarbamoyl and 1,2-(methyl)$_2$propylcarbamoyl. Examples of "N,N—(C$_{1-4}$ alkyl)$_2$carbamoyl" are N,N-(methyl)$_2$carbamoyl, N,N-(ethyl)$_2$carbamoyl and N-methyl-N-ethylcarbamoyl. Examples of "N,N—(C$_{1-6}$alkyl)$_2$carbamoyl" are the examples of "N,N—(C$_{1-4}$alkyl)$_2$carbamoyl" and additionally N,N-(pentyl)$_2$carbamoyl, N-methyl-N-pentylcarbamoyl and N-ethyl-N-hexylcarbamoyl. Examples of "N—(C$_{1-4}$alkyl)sulphamoyl" are N-(methyl)sulphamoyl and N-(ethyl)sulphamoyl. Examples of "N—(C$_{1-6}$alkyl)sulphamoyl" are the examples of "N—(C$_{1-4}$alkyl)sulphamoyl" and additionally N-pentylsulphamoyl, N-hexylsulphamoyl and 1,2-(methyl)$_2$propylsulphamoyl. Examples of "N,N—(C$_{1-4}$alkyl)$_2$sulphamoyl" are N,N-(methyl)$_2$sulphamoyl, N,N-(ethyl)$_2$sulphamoyl and N-(methyl)-N-(ethyl)sulphamoyl. Examples of "N,N—(C$_{1-6}$alkyl)$_2$sulphamoyl" are the examples of "N,N—(C$_{1-4}$alkyl)$_2$sulphamoyl" and additionally N,N-(pentyl)$_2$sulphamoyl, N-methyl-N-pentylsulphamoyl and N-ethyl-N-hexylsulphamoyl.

Examples of "cyano(C$_{1-4}$)alkyl" are cyanomethyl, cyanoethyl and cyanopropyl. Examples of "C$_{5-7}$cycloalkyl" are cyclopentyl, cyclohexyl and cycloheptyl. Examples of "C$_{3-8}$cycloalkyl" and "C$_{3-7}$cycloalkyl" include "C$_{5-7}$cycloalkyl", cyclopropyl, cyclobutyl and cyclooctyl. Examples of "C$_{3-6}$cycloalkyl" inclulde cyclopropyl, cyclobutyl, cyclopentyl and cyclohexyl.

The term "aminoC$_{1-4}$alkyl" includes aminomethyl, aminoethyl, aminopropyl, aminoisopropyl and aminobutyl. The term "aminoethyl" includes 1-aminoethyl and 2-aminoethyl. The term "aminopropyl" includes 1-aminopropyl, 2-aminopropyl and 3-aminopropyl and an analogous convention applies to terms such as aminoethyl and aminobutyl.

Examples of "C$_{1-4}$alkoxyC$_{1-4}$alkoxy" are methoxymethoxy, ethoxymethoxy, ethoxyethoxy and methoxyethoxy. Examples of "hydroxyC$_{1-4}$alkoxy" are hydroxyethoxy and hydroxypropoxy. Examples of "hydroxypropoxy" are 1-hydroxypropoxy, 2-hydroxypropoxy and 3-hydroxypropoxy.

Examples of "C$_{1-4}$alkylS(O)$_b$ (wherein b is 0, 1 or 2)", "C$_{1-4}$alkylS(O)$_c$ (wherein c is 0 to 2)", "C$_{1-4}$alkylS(O)$_d$ (wherein d is 0 to 2)", "C$_{1-4}$alkylS(O)$_e$ (wherein e is 0 to 2)", and "C$_4$alkylS(O)$_f$ (wherein f is 0 to 2)" independently include methylthio, ethylthio, propylthio, methanesulphinyl, ethanesulphinyl, propanesulphinyl, mesyl, ethanesulphonyl, propanesulphonyl and isopropanesulphonyl.

Examples of "C$_{3-6}$cycloalkylS(O)$_b$ (wherein b is 0, 1 or 2)" include cyclopropylthio, cyclopropylsulphinyl, cyclopropylsulphonyl, cyclobutylthio, cyclobutylsulphinyl, cyclobutylsulphonyl, cyclopentylthio, cyclopentylsulphinyl and cyclopentylsulphonyl.

Examples of "arylS(O)$_b$ (wherein b is 0, 1 or 2)" include phenylthio, phenylsulphinyl and phenylsulfonyl. Examples of "benzylS(O)$_b$ (wherein b is 0, 1 or 2)" inculde benzylthio, benzylsulfinyl and benzylsulfonyl. Examples of "heterocyclylS(O)$_b$ (wherein b is 0, 1 or 2)" include pyridylthio, pyridylsulfinyl, pyridylsulfonyl, imidazolylthio, imidazolylsulfinyl, imidazolylsulfonyl, pyrimidinylthio, pyrimidinyl-sufinyl, pyrimidinylsulfonyl, piperidylthio, piperidylsulfinyl and piperidylsulfonyl.

Examples of "C$_{1-6}$alkoxycarbonyl" include methoxycarbonyl, ethoxycarbonyl, n- and t-butoxycarbonyl. Examples of "C$_{1-6}$alkoxycarbonylamino" include methoxycarbonylamino, ethoxycarbonylamino, n- and t-butoxycarbonylamino. Examples of "C$_{1-6}$alkylsulphonyl-N-(C$_{1-6}$alkyl) amino" include methylsulphonyl-N-methylamino, ethylsulphonyl-N-methylamino and propylsulphonyl-N-ethylamino. Examples of "C$_{1-6}$alkylsulphonylamino" include methylsulphonylamino, ethylsulphonylamino and propylsulphonylamino. Examples of "C$_{1-6}$alkanoylamino" include formamido, acetamido and propionylamino. Where optional substituents are chosen from "0, 1, 2 or 3" groups it is to be understood that this definition includes all substituents being chosen from one of the specified groups or the substituents being chosen from two or more of the specified groups. An analogous convention applies to substituents chose from "0, 1 or 2" groups and "1 or 2" groups.

"Heterocyclyl" is a saturated, partially saturated or unsaturated, optionally substituted monocyclic ring containing 5 to 7 atoms of which 1, 2, 3 or 4 ring atoms are chosen from nitrogen, sulphur or oxygen, which may, unless otherwise specified, be carbon or nitrogen linked, wherein a —CH$_2$— group can optionally be replaced by a —C(O)— and a ring sulphur atom may be optionally oxidised to form the S-oxide(s). Examples and suitable values of the term "heterocyclyl" are morpholino, morpholinyl, piperidino, piperidyl, pyridyl, pyranyl, pyrrolyl, imidazolyl, thiazolyl, thienyl, dioxolanyl, thiadiazolyl, piperazinyl, isothiazolidinyl, triazolyl, tetrazolyl, pyrrolidinyl, 2-oxazolidinonyl, 5-isoxazolonyl, thiomorpholino, pyrrolinyl, homopiperazinyl, 3,5-dioxapiperidinyl, 3-oxopyrazolin-5-yl, tetrahydropyranyl, tetrahydrothiopyranyl, 1-oxotetrahydrothiopyranyl, 1,1-dioxotetrahydrothiopyranyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, and oxadiazolyl.

Suitably a "heterocyclyl" is morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl.

Conveniently "heterocyclyl" is oxazolyl, 1,3,4-oxadiazolyl, 1,2,4-oxadiazolyl, tetrazolyl, thizoyl, thiadiazolyl, pyridyl, imidazolyl, furyl, thienyl, morpholine, pyrimidyl, pyrazinyl, pyridazinyl, pyrazolyl, pyrazolinyl, and piperazinyl.

Suitable optional substituents for "heterocyclyl" as a saturated or partially saturated ring are 1, 2 or 3 substituents independently selected from halo, cyano, hydroxy, C$_{1-4}$alkyl, C$_{1-4}$alkoxy and C$_{1-4}$alkylS(O)$_b$ (wherein b is 0, 1 or 2). Further suitable substituents for "heterocyclyl" as a saturated or partially saturated ring are 1, 2 or 3 substituents independently selected from fluoro, chloro, cyano, hydroxy, methyl, ethyl, methoxy, methylthio, methylsulfinyl and methylsulfonyl.

Suitable optional susbtituents for "heterocyclyl" as an unsaturated ring are 1, 2 or 3 substituents independently selected from halo, cyano, nitro, amino, hydroxy, C$_{1-4}$alkyl, C$_{1-4}$alkoxy, C$_{1-4}$alkylS(O)$_b$ (wherein b is 0, 1 or 2), N—(C$_{1-4}$alkyl)amino and N,N—(C$_{1-4}$alkyl)$_2$amino. Further suitable optional susbtituents for "heterocyclyl" as an unsaturated ring are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Examples of "(heterocyclyl)$C_{1-4}$alkyl" are morpholinomethyl, morpholinethyl, morpholinylmethyl, morpholinylethyl, piperidinomethyl, piperidinoethyl, piperidylmethyl, piperidylethyl, imidazolylmethyl, imidazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl.

Examples of "aryl" are optionally substituted phenyl and naphthyl.

Examples of "aryl($C_{1-4}$)alkyl" are benzyl, phenethyl, naphthylmethyl and naphthylethyl.

Suitable optional substituents for "aryl" groups are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N—($C_{1-4}$alkyl)amino and N,N—($C_{1-4}$alkyl)$_2$amino. Further suitable optional susbtituents for "aryl" groups are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

"Heteroarylene" is a diradical of a heteroaryl group. A heteroaryl group is an aryl, monocyclic ring containing 5 to 7 atoms of which 1, 2, 3 or 4 ring atoms are chosen from nitrogen, sulphur or oxygen. Examples of heteroarylene are oxazolylene, oxadiazolylene, pyridylene, pyrimidinylene, imidazolylene, triazolylene, tetrazolylene, pyrazinylene, pyridazinylene, pyrrolylene, thienylene and furylene.

Suitable optional substituents for heteroaryl groups, unless otherwise defined, are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N—($C_{1-4}$alkyl)amino and N,N—($C_{1-4}$alkyl)$_2$amino. Further suitable optional susbtituents for "heteroaryl" groups are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Preferred values of A, Y, $R^1$, $R^4$, $R^5$, r and n are as follows. Such values may be used where appropriate with any of the definitions, claims, aspects or embodiments defined hereinbefore or hereinafter.

In one embodiment of the invention are provided compounds of formula (1), in an alternative embodiment are provided pharmaceutically-acceptable salts of compounds of formula (1), in a further alternative embodiment are provided in-vivo hydrolysable esters of compounds of formula (1), and in a further alternative embodiment are provided pharmaceutically-acceptable salts of in-vivo hydrolysable esters of compounds of formula (1).

Particular examples of in-vivo hydrolysable esters of compounds of the formula (1) are such esters of compounds of the formula (1) wherein Y comprises a group containing a carboxy group. Suitable esters are those hereinbefore described for carboxy groups.

In one aspect of the present invention there is provided a compound of formula (1) as depicted above wherein z is CH.

In another aspect of the invention Z is nitrogen.

In one aspect of the present invention there is provided a compound of formula (1) as depicted above wherein $R^4$ and $R^5$ are together —S—C($R^6$)=C($R^7$)—.

In another aspect of the invention $R^4$ and $R^5$ are together —C($R^7$)=C($R^6$)—S—.

In a further aspect of the invention, $R^6$ and $R^7$ are independently selected from hydrogen, halo or $C_{1-6}$alkyl.

Preferably $R^6$ and $R^7$ are independently selected from hydrogen, chloro, bromo or methyl.

Particularly $R^6$ and $R^7$ are independently selected from hydrogen or chloro.

More particularly one of $R^6$ and $R^7$ is chloro.

In one embodiment, one of R and $R^7$ is chloro and the other is hydrogen.

In another embodiment, both $R^6$ and $R^7$ are chloro.

In one aspect of the invention A is phenylene.

In another aspect of the invention A is heteroarylene.

Preferably A is selected from phenylene, pyridylene, pyrimidinylene, pyrrolylene, imidazolylene, triazolylene, tetrazolylene, oxazolylene, oxadiazolylene, thienylene and furylene.

In one embodiment, when A is heteroarylene, there is a nitrogen in a bridgehead position. In another embodiment, when A is heteroarylene, the heteroatoms are not in bridgehead positions. It will be appreciated that the preferred (more stable) bridgehead position is as shown below:

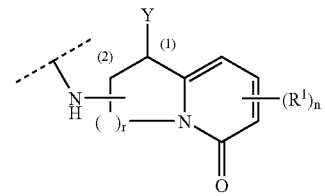

In one aspect of the invention n is 0 or 1.

In one aspect preferably n is 1.

In another aspect, preferably n is 0.

When n is 2, and the two $R^1$ groups, together with the carbon atoms of A to which they are attached, form a 4 to 7 membered ring, optionally containing 1 or 2 heteroatoms independently selected from O, S and N, conveniently such a ring is a 5 or 6 membered ring containing two O atoms (ie a cyclic acetal). When the two $R^1$ groups together form such a cyclic acetal, preferably it is not substituted. Most preferably the two $R^1$ groups together are the group —O—$CH_2$—O—.

In another aspect of the present invention $R^1$ is selected from halo, nitro, cyano, hydroxy, fluoromethyl, difluoromethyl, trifluoromethyl and $C_{1-4}$alkoxy.

In a further aspect $R^1$ is selected from halo, nitro, cyano, hydroxy, fluoromethyl, difluoromethyl, trifluoromethyl, —S(O)$_b$$C_{1-4}$alkyl (wherein b is 0, 1 or 2), $C_{1-4}$alkyl and $C_{1-4}$alkoxy.

In a further aspect $R^1$ is selected from halo, nitro, cyano, hydroxy, fluoromethyl, difluoromethyl, trifluoromethyl, —S(O)$_b$Me (wherein b is 0, 1 or 2), methyl and methoxy.

In a further aspect, $R^1$ is $C_{1-4}$alkyl.

Preferably $R^1$ is selected from halo and $C_{1-4}$alkoxy.

In another embodiment preferably $R^1$ is selected from fluoro, chloro, methyl, ethyl, methoxy and —O—$CH_2$—O—.

In one aspect of the invention r is 1 and when r is 1 the group

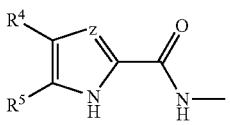

is a substituent on carbon (2) such that an example of when r is 1 is:

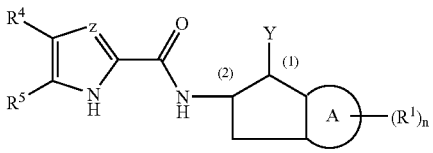

In another aspect of the invention r is 2 and when r is 2 the group

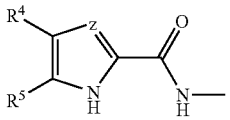

is a substituent on carbon (2) such that an example of when r is 2 is:

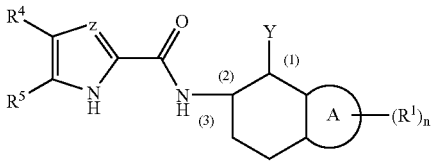

In another aspect of the invention r is 2 and when r is 2 the group

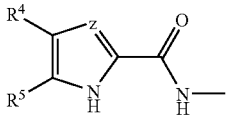

is a substituent on carbon (3) such that an example of when r is 2 is:

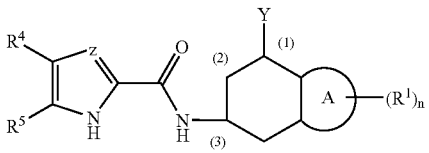

In one aspect of the invention Y is $-NR^2R^3$.
In another aspect of the invention Y is $-OR^3$.
Suitable values for $R^2$ and $R^3$ as heterocyclyl are morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl.

More suitable values for $R^2$ and $R^3$ as heterocyclyl are pyridyl, pyrimidinyl and imidazolyl.

Further suitable values for $R^2$ and $R^3$ as heterocyclyl are tetrahydrothiopyranyl, 1-oxotetrahydrothiopyranyl, 1,1-dioxotetrahydrothiopyranyl.

In one aspect of the invention, $R^2$ and $R^3$ are independently selected from groups of the formulae B and B' as hereinbefore described.

In one aspect of the invention $R^2$ and $R^3$ are independently selected from hydrogen, hydroxy, $C_{1-4}$alkyl [optionally substituted by 1 or 2 $R^8$ groups], $C_{3-7}$cycloalkyl (optionally substituted with 1 or 2 hydroxy groups), cyano($C_{1-4}$)alkyl, phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl, $-COR^8$ and $-SO_bR^8$ (wherein b is 0, 1 or 2);

$R^8$ is independently selected from hydrogen, hydroxy, $C_{1-4}$alkoxy, $C_{1-4}$alkoxyC$_{1-4}$alkyl, $C_{1-4}$alkoxyC$_{1-4}$alkoxy, hydroxyC$_{1-4}$alkoxy, C$_4$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, $-CO_2C_{1-4}$alkyl, aryl and aryl($C_{1-4}$)alkyl], $C_{2-4}$alkenyl, $C_{3-7}$cycloalkyl (optionally substituted by $-C(O)O$ $C_{1-4}$alkyl), 5- and 6-membered cyclic acetals and mono- and di-methyl derivatives thereof, halo($C_{1-4}$)alkyl, dihalo($C_{1-4}$)alkyl, trihalo($C_{1-4}$)alkyl, hydroxy($C_{1-4}$)alkyl, dihydroxy($C_{1-4}$)alkyl, cyano($C_{1-4}$)alkyl, heterocyclyl, heterocyclylC$_{1-4}$alkyl, aryl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$($C_{1-4}$)alkyl (wherein c is 0, 1 or 2), $-CH_2CH(NR^9R^{10})CO(NR^{9'}R^{10'})$, $-CH_2OR^9$, $(R^9)(R^{10})N-$, $-COOR^9$, $-CH_2COOR^9$, $-C(O)N(R^9)(R^{10})$, $-CH_2CH(CO_2R^9)OH$, $-CH_2CONR^9R^{10}$, $-CH_2CH(NR^9R^{10})CO_2R^{9'}$ and $-CH_2OCOR^9$;

$R^9$, $R^{9'}$, $R^{10}$ and $R^{10'}$ are independently selected from hydrogen, $C_{1-4}$alkyl (optionally substituted by 1 or 2 $R^{13}$), $C_{3-7}$cycloalkyl (optionally substituted by 1 or 2 hydroxy groups), $-C(=O)O^tBu$, $C_{2-4}$alkenyl, cyano($C_{1-4}$)alkyl and phenyl (optionally substituted by 1 or 2 groups selected from nitro, halo, hydroxy and cyano); or $R^9$ and $R^{10}$ together with the nitrogen to which they are attached, and/or $R^{9'}$ and $R^{10'}$ together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl and $C_{1-4}$alkoxy; or the ring may be optionally substituted on two adjacent carbons by —O—$CH_2$—O— to form a cyclic acetal wherein one or both of the hydrogens of the —O—$CH_2$—O— group may be replaced by a methyl;

$R^{13}$ is selected from halo, trihalomethyl and $C_{1-4}$alkoxy.

In a further aspect of the invention $R^2$ and $R^3$ are independently selected from hydrogen, $C_{1-4}$alkyl [optionally substituted by 1 or 2 $R^8$ groups], $C_{3-7}$cycloalkyl (optionally substituted with 1 or 2 hydroxy groups), —$COR^8$ and —$SO^bR^8$ (wherein b is 0, 1 or 2);

$R^8$ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —$CO_2C_{1-4}$alkyl, aryl and aryl($C_{1-4}$)alkyl], $C_{2-4}$alkenyl, $C_{3-7}$cycloalkyl (optionally substituted by —C(O)O$C_{1-4}$alkyl), 5- and 6-membered cyclic acetals and mono- and di-methyl derivatives thereof, halo($C_{1-4}$)alkyl, dihalo($C_{1-4}$)alkyl, trihalo($C_{1-4}$)alkyl, hydroxy($C_{1-4}$)alkyl, dihydroxy($C_{1-4}$)alkyl, cyano($C_{1-4}$)alkyl, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$($C_{1-4}$)alkyl (wherein c is 0, 1 or 2), —$CH_2CH(NR^9R^{10})CO(NR^{9'}R^{10'})$, —$CH_2OR^9$, $(R^9)(R^{10})N$—, —$COOR^9$, —$CH_2COOR^9$, —$C(O)N(R^9)(R^{10})$, —$CH_2CH(CO_2R^9)OH$, —$CH_2CONR^9R^{10}$, —$CH_2CH(NR^9R^{10})CO_2R^{9'}$ and —$CH_2OCOR^9$;

$R^9$, $R^{9'}$, $R^{10}$ and $R^{10'}$ are independently selected from hydrogen, $C_{1-4}$alkyl (optionally substituted by 1 or 2 $R^{13}$), —C(=O)O'Bu, $C_{2-4}$alkenyl, cyano($C_{1-4}$)alkyl, phenyl (optionally substituted by 1 or 2 groups selected from nitro, halo, hydroxy and cyano);

or $R^9$ and $R^{10}$ together with the nitrogen to which they are attached, and/or $R^{9'}$ and $R^{10'}$ together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl and $C_{1-4}$alkoxy; or the ring may be optionally substituted on two adjacent carbons by —O—$CH_2$—O— to form a cyclic acetal wherein one or both of the hydrogens of the —O—$CH_2$—O— group may be replaced by a methyl;

$R^{13}$ is selected from halo, trihalomethyl and $C_{1-4}$alkoxy.

In another aspect of the invention $R^2$ and $R^3$ are independently selected from hydrogen, $C_{1-4}$alkyl [optionally substituted by 1 or 2 $R^8$ groups], —$COR^8$ and —$SO_bR^8$ (wherein b is 0, 1 or 2);

$R^8$ is independently selected from hydrogen, hydroxy, $C_{1-4}$alkoxy, $C_{1-4}$alkoxy$C_{1-4}$alkyl, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —$CO_2C_{1-4}$alkyl, phenyl and aryl($C_{1-4}$)alkyl], $C_{2-4}$alkenyl, $C_{3-7}$cycloalkyl (optionally substituted by —C(O)O$C_{1-4}$alkyl), 5- and 6-membered cyclic acetals and mono- and di-methyl derivatives thereof, halo($C_{1-4}$)alkyl, trihalo($C_{1-4}$)alkyl, hydroxy($C_4$)alkyl, dihydroxy($C_{1-4}$)alkyl, cyano($C_{1-4}$)alkyl, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2 —$CH_2CH(NR^9R^{10})CO(NR^{9'}R^{10'})$, —$CH_2OR^9$, $(R^9)(R^{10})N$—, —$COOR^9$, —$CH_2COOR^9$, —$C(O)N(R^9)(R^{10})$, —$CH_2CH(CO_2R^9)OH$, —$CH_2CONR^9R^{10}$, —$CH_2CH(NR^9R^{10})CO_2R^{9'}$ and —$CH_2OCOR^9$;

$R^9$, $R^{9'}$, $R^{10}$ and $R^{10'}$ are independently selected from hydrogen, $C_{1-4}$alkyl (optionally substituted by 1 or 2 hydroxy groups), $C_{2-4}$alkenyl, and phenyl (optionally substituted by 1 or 2 groups selected from nitro, halo, hydroxy and cyano).

In one aspect, one of $R^9$ and $R^{10}$ is hydrogen and the other is selected from heterocyclyl and heterocyclyl($C_{1-4}$alkyl). Conveniently $R^9$ or $R^{10}$ as heterocyclyl and heterocyclyl ($C_{1-4}$alkyl) is selected from oxazolyl, 1,3,4-oxadiazolyl, 1,2,4-oxadiazolyl, tetrazolyl, thiazoyl, thiadiazolyl, pyridyl, imidazolyl, furyl, thienyl, morpholine, pyrimidyl, pyrazinyl, pyridazinyl, pyrazolyl, pyrazolinyl, piperazinyl, morpholinomethyl, morpholinethyl, morpholinylmethyl, morpholinylethyl, piperidinomethyl, piperidinoethyl, piperidylmethyl, piperidylethyl, tetrahydrothiopyranyl, 1-oxotetrahydrothiopyranyl, 1,1-dioxotetrahydrothiopyranyl, imidazolylmethyl, imidazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl;

wherein the heterocylic ring is optional substituted on any available atom by 1, 2 or 3 substituents independently selected from halo, cyano, hydroxy, $C_{1-4}$alkyl, $C_{1-4}$alkoxy and $C_{1-4}$alkylS(O)$_b$ (wherein b is 0, 1 or 2), and additionally when the heterocyclyl ring is a heteroaryl ring, further suitable optional substituents are selected from nitro, amino, N—($C_{1-4}$alkyl)amino and N,N—($C_{1-4}$alkyl)$_2$amino, end/or wherein any heterocyclic ring is optionally oxidised such that a —$CH_2$— group is replaced by a —C(O)— and/or a ring sulphur atom is oxidised to form the S-oxide(s).

In another aspect of the invention $R^2$ is selected from hydrogen, acetyl and $C_{1-4}$alkyl.

In a further aspect of the invention, Y is $NR^2R^3$ and $NR^2R^3$ forms a 4 to 7 membered saturated, partially saturated or unsaturated ring, optionally containing 1, 2 or 3 additional heteroatoms independently selected from N, O and S, wherein any —$CH_2$— may optionally be replaced by —C(=O)—, and any N or S atom may optionally be oxidised to form an N-oxide or SO or $SO_2$ group respectively, and wherein the ring is optionally substituted by 1 or 2 substituents independently selected from halo, cyano, $C_{1-4}$alkyl, hydroxy, $C_{1-4}$alkoxy and $C_{1-4}$alkylS(O)$_b$— (wherein b is 0, 1 or 2).

Suitable values for NR$^2$R$^3$ as a 4 to 7 membered ring are morpholino, 2,5-dioxomorpholino, piperidinyl, pyrrolidinyl, pyrazolyl, pyrrolyl, imidazolyl, piperazinyl and thiomorpholinyl.

In yet a further aspect of the inventions R$^3$ is selected from hydrogen, 1,3-dihydroxyisopropyl, 1,2-dihydroxypropyl, cyanomethyl, trifluoromethylcarbonyl, carboxyacetyl, carboxymethyl, formyl, acetyl, carbamoylacetyl, carbamoylmethyl, methoxyacetyl, methoxypropanoyl, acetoxyacetyl, methanesulfonyl, chloromethylsulfonyl, trifluoromethylsulfonyl, morpholinomethylcarbonyl, furylcarbonyl, thienylcarbonyl, nitrofurylcarbonyl, N,N-dimethylcarbamoyl, 4-methylpiperazinocarbonyl, N-ethylcarbamoyl, N-allylcarbamoyl, N-dinitrophenylcarbamoyl, pyridinylcarbonyl, tetrahydrofuran-2-on-5-ylcarbonyl, hydroxyphenylcarbonyl, acryloyl, 2-(tert-butoxycarbonyl)methylcarbonyl, aminoacetyl, 1-amino-1-carboxypropanoyl, chloroacetyl, hydroxyacetyl, carbamoylacetyl, carbamoylmethyl, methoxyacetyl, methoxypropanoyl, acetoxyacetyl, hydroxypiperidinoaminoacetyl, hydroxypyrrolidinylaminoacetyl, N-methyl-N-hydroxyethylaminoacetyl, N-benzyl-N-hydroxyethylaminoacetyl, N-(2,3-dihydroxypropyl)-N-methylaminoacetyl, N,N-bis(hydroxyethyl)aminoacetyl, N,N-bis(hydroxypropyl)aminoacetyl, (1-amino-1-carbonylamino)ethylcarbonyl, 1-hydroxy-1-carboxyethylcarbonyl, tert-butoxycarbonylmethyl, 1,3-dihydroxyisoprop-2-ylcarbonyl, 1-(tert-butoxycarbonylamino)-1-(carbamoyl)propanoyl, N-ethyl-N-(2-hydroxyethyl)aminoacetyl, thienylmethyl, tetrazolylmethyl, [2-(ethoxycarbonyl)cyclopropyl]methyl, N-(tert-butoxycarbonyl)aminoacetyl and N-(aminocarbonyl)-N-(tert-butoxycarbonyl)aminoacetyl.

In yet a further aspect of the inventions R$^3$ is selected from trifluoromethylcarbonyl, carboxyacetyl, formyl, acetyl, methanesulfonyl, morpholinomethylcarbonyl, furylcarbonyl, thienylcarbonyl, nitrofurylcarbonyl, N,N-dimethylcarbamoyl, 4-methylpiperazinocarbonyl, N-ethylcarbamoyl, N-allylcarbamoyl, N-dinitrophenylcarbamoyl, pyridinylcarbonyl, tetrahydrofuran-2-on-5-ylcarbonyl, hydroxyphenylcarbonyl, acryloyl, 2-(tert-butoxycarbonyl)methylcarbonyl, aminoacetyl, 1-amino-1-carboxypropanoyl, chloroacetyl, hydroxyacetyl, carbamoylacetyl, carbamoylmethyl, methoxyacetyl, methoxypropanoyl, acetoxyacetyl, N-methyl-N-hydroxyethylaminoacetyl, N-benzyl-N-hydroxyethylaminoacetyl, N-(2,3-dihydroxypropyl)-N-methylaminoacetyl, N,N-bis(hydroxyethyl)aminoacetyl, N,N-bis(hydroxypropyl)aminoacetyl, (1-amino-1-carbonylamino)ethylcarbonyl, 1-hydroxy-1-carboxyethylcarbonyl, tert-butoxycarbonylmethyl, 1,3-dihydroxyisoprop-2-ylcarbonyl, 1-(tert-butoxycarbonylamino)-1-(carbamoyl)propanoyl and N-ethyl-N-(2-hydroxyethyl)aminoacetyl.

A preferred class of compound is of the formula (1) wherein;

Z is CH;

R$^4$ and R$^5$ are together —S—C(R$^6$)=C(R$^7$)—;

R$^6$ is halo or hydrogen;

R$^7$ is halo or hydrogen;

A is phenylene;

n is 0, 1 or 2;

R$^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;

r is 1 or 2;

Y is —NR$^2$R$^3$ or —OR$^3$;

R$^2$ and R$^3$ are independently selected from hydrogen, $C_{1-4}$alkyl [optionally substituted by 1 or 2 R$^8$ groups], $C_{3-7}$cycloalkyl (optionally substituted with 1 or 2 hydroxy groups), phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopyridyl, 2-oxopyrrolidyl, 4-oxothiazolidyl, furyl, thienyl, oxazolyl, 1,3,4-oxadiazolyl, 1,2,4-oxadiazolyl, tetrahydrothiopyranyl, 1-oxotetrahydrothiopyranyl, 1,1-dioxotetrahydrothiopyranyl, —COR$^8$ and —SO$_b$R$^8$ (wherein b is 0, 1 or 2);

R$^8$ is independently selected from hydrogen, hydroxy, $C_{1-4}$alkoxy, $C_{1-4}$alkoxyC$_{1-4}$alkyl, $C_{1-4}$alkoxyC$_{1-4}$alkoxy, hydroxyC$_{1-4}$alkoxy, $C_{1-4}$alkyl, amino(C$_{1-4}$)alkyl [optionally substituted on nitrogen by 1 or 2 groups selected from $C_{1-4}$alkyl, hydroxy(C$_{1-4}$)alkyl, dihydroxy(C$_{1-4}$)alkyl, —CO$_2$C$_{1-4}$alkyl, aryl and aryl(C$_{1-4}$)alkyl], $C_{2-4}$alkenyl, $C_{3-7}$cycloalkyl (optionally substituted by —C(O)O C$_{1-4}$alkyl), 5- and 6-membered cyclic acetals and mono- and di-methyl derivatives thereof, halo(C$_{1-4}$)alkyl, dihalo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$)alkyl, heterocyclyl, heterocyclyl C$_{1-4}$alkyl, aryl, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), C$_{1-4}$alkylS(O)$_c$(C$_{1-4}$)alkyl (wherein c is 0, 1 or 2), —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and —CH$_2$OCOR$^9$;

R$^9$, R$^{9'}$, R$^{10}$ and R$^{10'}$ are independently selected from hydrogen, C$_{1-4}$alkyl (optionally substituted by 1 or 2 R$^{13}$), C$_{3-7}$cycloalkyl (optionally substituted by 1 or 2 hydroxy groups), —C(=O)O$^t$Bu, C$_{2-4}$alkenyl, cyano(C$_{1-4}$)alkyl and phenyl (optionally substituted by 1 or 2 groups selected from nitro, halo, hydroxy and cyano); or R$^9$ and R$^{10}$ together with the nitrogen to which they are attached, and/or R$^{9'}$ and R$^{10'}$, together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl and C$_{1-4}$alkoxy; or the ring may be optionally substituted on two adjacent carbons by —O—CH$_2$—O— to form a cyclic acetal wherein one or both of the hydrogens of the —O—CH$_2$—O— group may be replaced by a methyl;

R$^{13}$ is selected from halo, trihalomethyl and C$_{1-4}$alkoxy;

or a pharmaceutically acceptable salt or in vivo hydrolysable ester thereof;

with the proviso that the compound of formula (1) is not:
  i) 2,3-dichloro-5-(N-{1-[N-(1,1-dimethylethoxy)carbonylamino]indan-2-yl}carbamoyl)-4H-thieno[3,2-b]pyrrole;
  ii) 5-[N-(1-aminoindan-2-yl)carbamoyl]-2,3-dichloro-4H-thieno[3,2-b]pyrrole;
  iii) 5-[N-(1-acetamidoindan-2-yl)carbamoyl]-2,3-dichloro-4H-thieno[3,2-b]pyrrole;
  iv) 2,3-dichloro-5-{N-[1-(methanesulphonamido)indan-2-yl]carbamoyl}-4H-thieno[3,2-b]pyrrole;

v) 2,3-dichloro-5-{N-[1-(methylamino)indan-2-yl]carbamoyl}-4H-thieno[3,2-b]pyrrole;

vi) 2,3-dichloro-5-{N-[1-(methylacetamido)indan-2-yl]carbamoyl}-4H-thieno[3,2-b]pyrrole;

vii) 2,3-dichloro-5-[N-(1-hydroxyindan-2-yl)carbamoyl]-4H-thieno[3,2-b]pyrrole;

viii) 2,3-dichloro-5-[N-(6fluoro-1-hydroxyindan-2yl)carbamoyl]-4H-thieno[3,2-b]pyrrole;

ix) 2,3-dichloro-5-[N-(-1-methoxyindan-2-yl)carbamoyl]-4-thieno[3,2-b]pyrrole;

x) 2,3-dichloro-5-[N-(1-hydroxy-1,2,3,4-tetrahydronaphth-2-yl)carbamoyl]-4H-thieno[3,2-b]pyrrole.

Another preferred class of compounds is of formula (1) wherein:

Z is CH;

$R^4$ and $R^5$ are together —$C(R^7)$=$C(R^6)$—S—;

$R^6$ is chloro;

$R^7$ is hydrogen;

A is phenylene;

n is 0, 1 or 2;

$R^1$ is independently selected from halo, cyano, nitro, hydroxy, methyl, fluoromethyl, difluoromethyl, trifluoromethyl, methoxy, —SMe, —SOMe, —$SO_2$Me and, (when n is 2) methylenedioxy;

r is 1 or 2;

Y is —$NR^2R^3$ or —$OR^3$;

$R^2$ and $R^3$ are independently selected from hydrogen, $C_{1-4}$alkyl [optionally substituted by 1 or 2 $R^8$ groups], $C_{3-7}$cycloalkyl (optionally substituted with 1 or 2 hydroxy groups), phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl, —$COR^8$ and —$SO_bR^8$ (wherein b is 0, 1 or 2);

$R^8$ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —$CO_2C_{1-4}$alkyl, aryl and aryl($C_{1-4}$)alkyl], $C_{2-4}$alkenyl, $C_{3-7}$cycloalkyl (optionally substituted by —C(O)O $C_{1-4}$alkyl), 5- and 6-membered cyclic acetals and mono- and di-methyl derivatives thereof, halo($C_{1-4}$)alkyl, dihalo($C_{1-4}$) alkyl, trihalo($C_{1-4}$)alkyl, hydroxy($C_{1-4}$)alkyl, dihydroxy ($C_{1-4}$)alkyl, cyano($C_{1-4}$)alkyl, heterocyclyl, heterocyclyl $C_{1-4}$alkyl, aryl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS (O)$_c$($C_{1-4}$)alkyl (wherein c is 0, 1 or 2), —$CH_2CH(NR^9R^{10}$) $CO(NR^{9'}R^{10'}$), —$CH_2OR^9$, ($R^9$)($R^{10}$)N—, —$COOR^9$, —$CH_2COOR^9$, —C(O)N($R^9$)($R^{10}$), —$CH_2CH(CO_2R^9)$OH, —$CH_2CONR^9R^0$, —$CH_2CH(NR^9R^{10})CO_2R^{9'}$ and —$CH_2OCOR^9$;

$R^9$, $R^{9'}$, $R^{10}$ and $R^{1'}$ are independently selected from hydrogen, $C_{1-4}$alkyl (optionally substituted by 1 or 2 $R^{13}$), $C_{3-7}$cycloalkyl (optionally substituted by 1 or 2 hydroxy groups), —C(=O)O$^t$Bu, $C_{2-4}$alkenyl, cyano($C_{1-4}$)alkyl and phenyl (optionally substituted by 1 or 2 groups selected from nitro, halo, hydroxy and cyano); or $R^9$ and $R^{10}$ together with the nitrogen to which they are attached, and/or $R^{9'}$ and $R^{10'}$ together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl and $C_4$alkoxy; or the ring may be optionally substituted on two adjacent carbons by —O—$CH_2$—O— to form a cyclic acetal wherein one or both of the hydrogens of the —O—$CH_2$—O— group may be replaced by a methyl;

$R^{13}$ is selected from halo, trihalomethyl and $C_{1-4}$alkoxy;

or a pharmaceutically acceptable salt or in vivo hydrolysable ester thereof;

with the proviso that the compound of formula (1) is not:
i) 2-chloro-5-[N-(1-hydroxyindan-2-yl)carbamoyl]-6H-thieno[2,3-b]pyrrole.

Another preferred class of compound is of the formula (1) wherein:

Z is CH;

$R^4$ and $R^5$ are together —S—$C(R^6)$=$C(R^7)$—;

$R^6$ is chloro;

$R^7$ is hydrogen or chloro;

A is phenylene;

n is 0, 1 or 2;

$R^1$ is independently selected from halo, cyano, nitro, hydroxy, methyl, fluoromethyl, difluoromethyl, trifluoromethyl, methoxy, —SMe, —SOMe, —$SO_2$Me and, (when n is 2) methylenedioxy;

r is 1 or 2;

Y is —$NR^2R^3$;

$R^2$ and $R^3$ are independently selected from hydrogen, $C_{1-4}$alkyl [optionally substituted by 1 or 2 $R^8$ groups], —$COR^8$ and —$SO_bR^8$ (wherein b is 0, 1 or 2);

$R^8$ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —$CO_2C_{1-4}$alkyl, aryl and aryl($C_{1-4}$)alkyl], $C_{2-4}$alkenyl, $C_{3-7}$cycloalkyl (optionally substituted by —C(O)O $C_{1-4}$alkyl), 5- and 6-membered cyclic acetals and mono- and di-methyl derivatives thereof, halo($C_{1-4}$)alkyl, dihalo($C_{1-4}$) alkyl, trihalo($C_{1-4}$)alkyl, hydroxy($C_{1-4}$)alkyl, dihydroxy ($C_{1-4}$)alkyl, cyano($C_{1-4}$)alkyl, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS (O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$($C_{1-4}$)alkyl (wherein c is 0, 1 or 2), —$CH_2CH(NR^9R^{10})CO(NR^{9'}R^{10'}$), —$CH_2OR^9$, ($R^9$)($R^{10}$) N—, —$COOR^9$, —$CH_2COOR^9$, —C(O)N($R^9$)($R^{10}$), —$CH_2CH(CO_2R^9)$OH, —$CH_2CONR^9R^{10}$, —$CH_2CH (NR^9R^{10})CO_2R^{9'}$ and —$CH_2OCOR^9$;

$R^9$, $R^{9'}$, $R^{10}$ and $R^{10'}$ are independently selected from hydrogen, $C_{1-4}$alkyl (optionally substituted by 1 or 2 $R^{13}$), —C(=O)O$^t$Bu, $C_{2-4}$alkenyl, cyano($C_{1-4}$)alkyl, phenyl (optionally substituted by 1 or 2 groups selected from nitro, halo, hydroxy and cyano);

$R^{13}$ is selected from halo, trihalomethyl and $C_{1-4}$alkoxy;

or a pharmaceutically acceptable salt or in vivo hydrolysable ester thereof;

with the proviso that the compound of formula (1) is not:
  i) 2,3-dichloro-5-(N-{1-[N-(1,1-dimethylethoxy)carbonylamino]indan-2-yl}carbamoyl)-4H-thieno[3,2-b]pyrrole;
  ii) 5-[N-(1-aminoindan-2-yl)carbamoyl]-2,3-dichloro-4H-thieno[3,2-b]pyrrole;
  iii) 5-[N-(1-acetamidoindan-2-yl)carbamoyl]-2,3-dichloro-4H-thieno[3,2-b]pyrrole;
  iv) 2,3-dichloro-5-{N-[1-(methanesulphonamido)indan-2-yl]carbamoyl}-4H-thieno[3,2-b]pyrrole;
  v) 2,3-dichloro-5-{N-[1-(methylamino)indan-2-yl]carbamoyl}-4H-thieno[3,2-b]pyrrole;
  vi) 2,3-dichloro-5-{N-[1-(methylacetamido)indan-2-yl]carbamoyl}-4H-thieno[3,2-b]pyrrole.

Another preferred class of compound is of the formula (1) wherein:
  Z is CH;
  $R^4$ and $R^5$ are together —S—C($R^6$)=C($R^7$)—;
  $R^6$ is hydrogen or halo;
  $R^7$ is hydrogen or halo;
  A is phenylene;
  n is 0, 1 or 2;
  $R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
  r is 1 or 2;
  Y is —OR$^3$;
  $R^3$ is selected from hydrogen, $C_{1-4}$alkyl [optionally substituted by 1 or 2 $R^8$ groups], —COR$^8$ and —SO$_b$R$^8$ (wherein b is 0, 1 or 2);
    wherein $R^8$ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —CO$_2$C$_{1-4}$alkyl, aryl and aryl($C_{1-4}$)alkyl], $C_{2-4}$alkenyl, $C_{3-7}$cycloalkyl (optionally substituted by —C(O)O $C_{1-4}$alkyl), 5- and 6-membered cyclic acetals and mono- and di-methyl derivatives thereof, halo($C_{1-4}$)alkyl, dihalo($C_{1-4}$) alkyl, trihalo($C_{1-4}$)alkyl, hydroxy($C_{1-4}$)alkyl, dihydroxy ($C_{1-4}$)alkyl, cyano($C_{1-4}$)alkyl, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$($C_{1-4}$)alkyl (wherein c is 0, 1 or 2), —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, CH$_2$CONR$^9$R$^{10}$, —CH$_2$CH(NR$^9$R$^{10}$)CO$_2$R$^{9'}$ and —CH$_2$OCOR$^9$;

$R^9$, $R^{9'}$ $R^{10}$ and $R^{10'}$ are independently selected from hydrogen, $C_{1-4}$alkyl (optionally substituted by 1 or 2 $R^{13}$), —C(=O)O$^t$Bu, $C_{2-4}$alkenyl, cyano($C_{1-4}$)alkyl and phenyl (optionally substituted by 1 or 2 groups selected from nitro, halo, hydroxy and cyano);

$R^{13}$ is selected from halo, trihalomethyl and $C_{1-4}$alkoxy;

or a pharmaceutically acceptable salt or in vivo hydrolysable ester thereof;

with the proviso that the compound of formula (1) is not:
  i) 2,3-dichloro-5-[N-(1-hydroxyindan-2-yl)carbamoyl]-4H-thieno[3,2-b]pyrrole;
  ii) 2,3dichloro-5-[N-(6-fluoro-1-hydroxyindan-2-yl)carbamoyl]-4H-thieno[3,2-b]pyrrole;
  iii) 2,3-dichloro-5-[N-(1methoxyindan-2yl)carbamoyl]-4H-thieno[3,2-b]pyrrole;
  iv) 2,3-dichloro-5-[N-(1-hydroxy-1,2,3,4-tetrahydronaphth-2-yl)carbamoyl]-4H-thieno[3,2-b]pyrrole.

A further preferred class of compound is of the formula (1) wherein;
  Z is CH;
  $R^4$ and $R^5$ are together —C($R^7$)=C($R^6$)—S—;
  $R^6$ is halo;
  $R^7$ is hydrogen;
  A is phenylene;
  n is 0, 1 or 2;
  $R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
  r is 1 or 2;
  Y is —NR$^2$R$^3$;
  $R^2$ and $R^3$ are independently selected from hydrogen, $C_4$alkyl [optionally substituted by 1 or 2 $R^8$ groups], —COR$^8$ and —SO$_b$R$^8$ (wherein b is 0, 1 or 2);

$R^8$ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —CO$_2$C$_{1-4}$alkyl, aryl and aryl($C_{1-4}$)alkyl], $C_{2-4}$alkenyl, $C_{3-7}$cycloalkyl (optionally substituted by —C(O)O $C_{1-4}$alkyl), 5- and 6-membered cyclic acetals and mono- and di-methyl derivatives thereof, halo($C_{1-4}$)alkyl, dihalo($C_{1-4}$) alkyl, trihalo($C_{1-4}$)alkyl, hydroxy($C_{1-4}$)alkyl, dihydroxy ($C_{1-4}$)alkyl, cyano($C_{1-4}$)alkyl, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$($C_{1-4}$)alkyl (wherein c is 0, 1 or 2), —CH$_2$CH(NR$^9$R$^{10}$)CO(NR$^{9'}$R$^{10'}$), —CH$_2$OR$^9$, (R$^9$)(R$^{10}$)

N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and

—CH$_2$OCOR$^9$;

R$^9$, R$^{9'}$, R$^{10}$ and R$^{10'}$ are independently selected from hydrogen, C$_{1-4}$alkyl (optionally substituted by 1 or 2 R$^{13}$), —C(=O)O$^t$Bu, C$_{2-4}$alkenyl, cyano(C$_{1-4}$)alkyl and phenyl (optionally substituted by 1 or 2 groups selected from nitro, halo, hydroxy and cyano);

R$^{13}$ is selected from halo, trihalomethyl and C$_{1-4}$alkoxy;

or a pharmaceutically acceptable salt or in vivo hydrolysable ester thereof.

Another preferred class of compound is of the formula (1) wherein:

Z is CH;
R$^4$ and R$^5$ are together —C(R$^7$)=C(R$^6$)—S—;
R$^6$ is hydrogen or halo;
R$^7$ is hydrogen or halo;
A is phenylene;
n is 0, 1 or 2;
R$^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
r is 1 or 2;
Y is —OR$^3$;
R$^3$ is selected from hydrogen, C$_{1-4}$alkyl [optionally substituted by 1 or 2 R$^8$ groups], —COR$^8$ and —SO$_b$R$^8$ (wherein b is 0, 1 or 2);
R$^8$ is independently selected from hydrogen, hydroxy, C$_{1-4}$alkoxy, C$_{1-4}$alkoxyC$_{1-4}$alkyl, C$_{1-4}$alkoxyC$_{1-4}$alkoxy, hydroxyC$_{1-4}$alkoxy, C$_{1-4}$alkyl, amino(C$_{1-4}$)alkyl [optionally substituted on nitrogen by 1 or 2 groups selected from C$_{1-4}$alkyl, hydroxy(C$_{1-4}$)alkyl, dihydroxy(C$_{1-4}$)alkyl, —CO$_2$C$_4$alkyl, aryl and aryl(C$_{1-4}$)alkyl], C$_{2-4}$alkenyl, C$_{3-7}$cycloalkyl (optionally substituted by —C(O)OC$_{1-4}$alkyl), 5- and 6-membered cyclic acetals and mono- and di-methyl derivatives thereof, halo(C$_{1-4}$)alkyl, dihalo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$)alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and C$_{1-4}$alkyl), pyrazinyl, piperazinyl, 4-methylpiperazino, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), C$_{1-4}$alkylS(O)$_c$(C$_{1-4}$)alkyl (wherein c is 0, 1 or 2), —CH$_2$CH(NR$^9$R$^{0}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and

—CH$_2$OCOR$^9$;

R$^9$, R$^{9'}$, R$^{10}$ and R$^{10'}$ are independently selected from hydrogen, C$_{1-4}$alkyl (optionally substituted by 1 or 2 R$^{13}$), —C(=O)O$^t$Bu, C$_{2-4}$alkenyl, cyano(C$_{1-4}$)alkyl, phenyl (optionally substituted by 1 or 2 groups selected from nitro, halo, hydroxy and cyano);

or a pharmaceutically acceptable salt or in vivo hydrolysable ester thereof;

provided that the compound of formula (1) is not:

2-chloro-5-[N-(1-hydroxyindan-2-yl)carbamoyl]-6H-thieno[2,3-b]pyrrole.

A further preferred class of compound is of the formula (1) wherein;

Z is CH;
R$^4$ and R$^5$ are together —C(R$^7$)=C(R$^6$)—S—;
R$^6$ is halo;
R$^7$ is hydrogen;
A is phenylene;
n is 0
r is 1;
Y is —NR$^2$R$^3$;
R$^2$ is hydrogen or C$_{1-4}$alkyl;
R$^3$ is selected from C$_{1-4}$alkyl [optionally substituted by 1 or 2 R$^8$ groups], —COR$^8$ and —SO$_b$R$^8$ (wherein b is 0, 1 or 2);
R$^8$ is independently selected from hydrogen, hydroxy, C$_{1-4}$alkoxy, C$_{1-4}$alkoxyC$_{1-4}$alkyl, C$_{1-4}$alkyl, amino(C$_{1-4}$)alkyl [optionally substituted on nitrogen by 1 or 2 groups selected from C$_{1-4}$alkyl, hydroxy(C$_{1-4}$)alkyl, dihydroxy(C$_{1-4}$)alkyl, —CO$_2$C$_{1-4}$alkyl, phenyl and aryl(C$_{1-4}$)alkyl], C$_{2-4}$alkenyl, C$_{3-7}$cycloalkyl (optionally substituted by —C(O)OC$_{1-4}$alkyl), 5- and 6-membered cyclic acetals and mono- and di-methyl derivatives thereof, halo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$)alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and C$_{1-4}$alkyl), pyrazinyl, piperazinyl, 4-methylpiperazino, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2 —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and

—CH$_2$OCOR$^9$;

R$^9$, R$^{9'}$, R$^{10}$ and R$^{10'}$ are independently selected from hydrogen, C$_{1-4}$alkyl (optionally substituted by 1 or 2 hydroxy groups), C$_{2-4}$alkenyl, and phenyl (optionally substituted by 1 or 2 groups selected from nitro, halo, hydroxy and cyano);

or a pharmaceutically acceptable salt or in vivo hydrolysable ester thereof.

A further preferred class of compound is of the formula (1) wherein;

Z is CH;
R$^4$ and R$^5$ are together —S—C(R$^6$)=C(R$^7$)—;
R$^6$ is halo;
R$^7$ is hydrogen;
A is phenylene;
n is 0;
r is 1;

Y is —NR²R³;

R² is hydrogen or $C_{1-4}$alkyl;

R³ is selected from $C_{1-4}$alkyl [optionally substituted by 1 or 2 R⁸ groups], —COR⁸ and —SO$_b$R⁸ (wherein b is 0, 1 or 2);

R⁸ is independently selected from hydrogen, hydroxy, $C_{1-4}$alkoxy, $C_{1-4}$alkoxy$C_{1-4}$alkyl, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$), —CO$_2$$C_{1-4}$alkyl, phenyl and aryl($C_{1-4}$)alkyl], $C_{2-4}$alkenyl, $C_{3-7}$cycloalkyl (optionally substituted by —C(O)OC$_{1-4}$alkyl), 5- and 6-membered cyclic acetals and mono- and di-methyl derivatives thereof, halo(C-4)alkyl, trihalo($C_{1-4}$)alkyl, hydroxy($C_{1-4}$)alkyl, dihydroxy($C_{1-4}$)alkyl, cyano($C_{1-4}$)alkyl, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxotetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2 -CH$_2$CH(NR⁹R¹⁰)CO(NR⁹'R¹⁰'), —CH$_2$OR⁹, (R⁹)(R¹⁰)N—, —COOR⁹, —CH$_2$COOR⁹, —C(O)N(R⁹)(R¹⁰), —CH$_2$CH(CO$_2$R⁹)OH, —CH$_2$CONR⁹R¹⁰, —CH$_2$CH(NR⁹R¹⁰)CO$_2$R⁹' and —CH$_2$OCOR⁹';

R⁹, R⁹', R¹⁰ and R¹⁰' are independently selected from hydrogen, $C_{1-4}$alkyl (optionally substituted by 1 or 2 hydroxy groups), $C_{2-4}$alkenyl, and phenyl (optionally substituted by 1 or 2 groups selected from nitro, halo, hydroxy and cyano);

or a pharmaceutically acceptable salt or in vivo hydrolysable ester thereof;

provided that the compound of formula (1) is not:
(i) 2,3-dichloro-5-(N-{1-[N-(1,1-dimethylethoxy)carbonylamino]indan-2-yl}carbamoyl)-4H-thieno [3,2-b]pyrrole;
(ii) 5-[N-(1-aminoindan-2-yl)carbamoyl]-2,3-dichloro-4H-thieno[3,2-b]pyrrole;
(iii) 5-[N-(1-acetamidoindan-2-yl)carbamoyl]-2,3-dichloro-4H-thieno[3,2-b]pyrrole;
(iv) 2,3-dichloro-5-{N-[1-(methansulphonamido)indan-2-yl]carbamoyl}-4H-thieno[3,2-b]pyrrole;
(v) 2,3-dichloro-5-{N-[1-(methylamino)indan-2-yl]carbamoyl}-4H-thieno[3,2-b]pyrrole;
(iv) 2,3-dichloro-5-{N-[1-methylacetamido)indan-2-yl]carbamoyl}-4H-thieno[3,2-b]pyrrole.

A preferred class of compound is of the formula (1) wherein;

Z is nitrogen;

R⁴ and R⁵ are together —S—C(R⁶)═C(R⁷)—;

R⁶ is halo or hydrogen;

R⁷ is halo or hydrogen;

A is phenylene;

n is 0, 1 or 2;

R¹ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;

r is 1 or 2;

Y is —NR²R³ or —OR³;

R² and R³ are independently selected from hydrogen, $C_{1-4}$alkyl [optionally substituted by 1 or 2 R⁸ groups], $C_{3-7}$cycloalkyl (optionally substituted with 1 or 2 hydroxy groups), phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopyridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl, —COR⁸ and —SO$_b$R⁸ (wherein b is 0, 1 or 2);

R⁸ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —CO$_2$$C_{1-4}$alkyl, aryl and aryl($C_{1-4}$)alkyl], $C_{2-4}$alkenyl, $C_{3-7}$cycloalkyl (optionally substituted by —C(O)OC$_{1-4}$alkyl), 5- and 6-membered cyclic acetals and mono- and di-methyl derivatives thereof, halo($C_{1-4}$)alkyl, dihalo($C_{1-4}$)alkyl, trihalo($C_{1-4}$)alkyl, hydroxy(C$_4$)alkyl, dihydroxy($C_{1-4}$)alkyl, cyano($C_{1-4}$)alkyl, heterocyclyl, heterocyclylC$_{1-4}$alkyl, aryl, C$_4$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$(C$_{1-4}$)alkyl (wherein c is 0, 1 or 2), —CH$_2$CH(NR⁹R¹⁰)CO(NR⁹'R¹⁰'), —CH$_2$OR⁹, (R⁹)(R¹⁰)N—, —COOR⁹, —CH$_2$COOR⁹, —C(O)N(R⁹)(R¹⁰), —CH$_2$CH(CO$_2$R⁹)OH, —CH$_2$CONR⁹R¹⁰, —CH$_2$CH(NR⁹R¹⁰)CO$_2$R⁹' and —CH$_2$OCOR⁹;

R⁹, R⁹', R¹⁰ and R¹⁰' are independently selected from hydrogen, $C_{1-4}$alkyl (optionally substituted by 1 or 2 R¹³), $C_{3-7}$cycloalkyl (optionally substituted by 1 or 2 hydroxy groups), —C(═O)O$^t$Bu, $C_{2-4}$alkenyl, cyano($C_{1-4}$)alkyl, phenyl (optionally substituted by 1 or 2 groups selected from nitro, halo, hydroxy and cyano); or R⁹ and R¹⁰ together with the nitrogen to which they are attached, and/or R⁹' and R¹⁰' together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl and $C_{1-4}$alkoxy; or the ring may be optionally substituted on two adjacent carbons by —O—CH$_2$—O— to form a cyclic acetal wherein one or both of the hydrogens of the —O—CH$_2$—O— group may be replaced by a methyl;

R¹³ is selected from halo, trihalomethyl and $C_{1-4}$alkoxy;

or a pharmaceutically acceptable salt or in vivo hydrolysable ester thereof;

with the proviso that the compound of formula (1) is not:
(i) 2,3-dichloro-5-(N-{1-[N-(1,1-dimethylethoxy)carbonylamino]indan-2-yl}carbamoyl)-4H-thieno[3,2-b]pyrrole;
(ii) 5-[N-(1-aminoindan-2-yl)carbamoyl]-2,3-dichloro-4H-thieno[3,2-b]pyrrole;

(iii) 5-[N-(1-acetamidoindan-2-yl)carbamoyl]-2,3-dichloro-4H-thieno[3,2-b]pyrrole;
(iv) 2,3-dicholor-5-{N-[1-(methansulphonamido)indan-2-yl]carbamoyl}-4H-thieno [3,2-b]pyrrole;
(v) 2,3-dichloro-5-{N-[1-(methylamino)indan-2-yl]carbamoyl}-4H-thieno[3,2-b]pyrrole;
(vi) 2,3-dichloro-5-{N-[1-(methylacetamido)indan-2-yl]carbamoyl}-4H-thieno[3,2-b]pyrrole;
(vii) 2,3-dichloro-5-[N-(1-hydroxyindan-2-yl)carbamoyl]-4H-thieno[3,2-b]pyrrole;
(viii) 2,3-dichloro-5-[N-(6-fluoro-1-hydroxyindan-2-yl)carbamoyl]-4H-thieno[3,2-b]pyrrole;
(ix) 2,3-dichloro-5-[N-(1-methoxyindan-2-yl)carbamoyl]-4H-thieno[3,2-b]pyrrole;
(x) 2,3-dichloro-5-[N-(1-hydroxy-1,2,3,4-tetrahydronaphth-2-yl)carbamoyl]-4H-thieno[3,2-b]pyrrole.

Another preferred class of compounds is of formula (1) wherein:
Z is nitrogen;
$R^4$ and $R^5$ are together —C($R^7$)=C($R^6$)—S—;
$R^6$ is chloro;
$R^7$ is hydrogen;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —$SO_2$Me and, (when n is 2) methylenedioxy;
r is 1 or 2;
Y is —$NR^2R^3$ or —$OR^3$;
$R^2$ and $R^3$ are independently selected from hydrogen, $C_{1-4}$alkyl [optionally substituted by 1 or 2 $R^8$ groups], $C_{3-7}$cycloalkyl (optionally substituted with 1 or 2 hydroxy groups), phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl, —$COR^8$ and —$SO_bR^8$ (wherein b is 0, 1 or 2);
$R^8$ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_4$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —$CO_2C_{1-4}$alkyl, aryl and aryl($C_{1-4}$)alkyl], $C_{2-4}$alkenyl, $C_{3-7}$cycloalkyl (optionally substituted by —C(O)O $C_{1-4}$alkyl), 5- and 6-membered cyclic acetals and mono- and di-methyl derivatives thereof, halo($C_{1-4}$)alkyl, dihalo($C_{1-4}$) alkyl, trihalo($C_{1-4}$)alkyl, hydroxy($C_{1-4}$)alkyl, dihydroxy ($C_{1-4}$)alkyl, cyano($C_{1-4}$)alkyl, heterocyclyl, heterocyclyl $C_{1-4}$alkyl, aryl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$($C_{1-4}$)alkyl (wherein c is 0, 1 or 2), —$CH_2CH(NR^9R^{10})$ CO(N$R^{9'}R^{10'}$), —$CH_2OR^9$, ($R^9$)($R^{10}$)N—, —$COOR^9$, —$CH_2COOR^9$, —C(O)N($R^9$)($R^{10}$), —$CH_2CH(CO_2R^9)$OH, —$CH_2CONR^9R^{10}$, —$CH_2CH(NR^9R^{10})CO_2R^9$ and —$CH_2OCOR^9$;
$R^9$, $R^{9'}$, $R^{10}$ and $R^{10'}$ are independently selected from hydrogen, $C_{1-4}$alkyl (optionally substituted by 1 or 2 $R^{13}$), $C_{3-7}$cycloalkyl (optionally substituted by 1 or 2 hydroxy groups), —C(=O)O$^t$Bu, $C_{2-4}$alkenyl, cyano($C_{1-4}$)alkyl and phenyl (optionally substituted by 1 or 2 groups selected from nitro, halo, hydroxy and cyano); or $R^9$ and $R^{10}$ together with the nitrogen to which they are attached, and/or $R^{9'}$ and $R^{10'}$ together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl and $C_{1-4}$alkoxy; or the ring may be optionally substituted on two adjacent carbons by —O—$CH_2$—O— to form a cyclic acetal wherein one or both of the hydrogens of the —O—$CH_2$—O— group may be replaced by a methyl;

$R^{13}$ is selected from halo, trihalomethyl, and $C_{1-4}$alkoxy;

or a pharmaceutically acceptable salt or in vivo hydrolysable ester thereof;

with the proviso that the compound of formula (1) is not:
2-chloro-5-[N-(1-hydroxyindan-2-yl)carbamoyl]-6H-thieno[2,3-b]pyrrole.

Another preferred class of compound is of the formula (1) wherein:
Z is nitrogen;
$R^4$ and $R^5$ are together —S—C($R^6$)=C($R^7$)—;
$R^6$ is chloro;
$R^7$ is hydrogen or chloro;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —$SO_2$Me and, (when n is 2) methylenedioxy;
r is 1 or 2;
Y is —$NR^2R^3$;
$R^2$ and $R^3$ are independently selected from hydrogen, $C_{1-4}$alkyl [optionally substituted by 1 or 2 $R^8$ groups], —$COR^8$ and —$SO_bR^8$ (wherein b is 0, 1 or 2);
$R^8$ is independently selected from hydrogen, hydroxy, $C_{1-4}$alkoxy, $C_{1-4}$alkoxy$C_{1-4}$alkyl, $C_{1-4}$alkoxy$C_{1-4}$alkoxy, hydroxy$C_{1-4}$alkoxy, $C_{1-4}$alkyl, amino($C_{1-4}$)alkyl [optionally substituted on nitrogen by 1 or 2 groups selected from $C_{1-4}$alkyl, hydroxy($C_{1-4}$)alkyl, dihydroxy($C_{1-4}$)alkyl, —$CO_2C_{1-4}$alkyl, aryl and aryl($C_{1-4}$)alkyl], $C_{2-4}$alkenyl, $C_{3-7}$cycloalkyl (optionally substituted by —C(O)O $C_{1-4}$alkyl), 5- and 6-membered cyclic acetals and mono- and di-methyl derivatives thereof, halo($C_{1-4}$)alkyl, dihalo($C_{1-4}$) alkyl, trihalo($C_{1-4}$)alkyl, hydroxy($C_{1-4}$)alkyl, dihydroxy ($C_{1-4}$)alkyl, cyano($C_{1-4}$)alkyl, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS (O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$($C_{1-4}$)alkyl (wherein c is 0, 1 or 2), —$CH_2CH(NR^9R^{10})CO(NR^{9'}R^{10'})$, —$CH_2OR^9$, ($R^9$)($R^{10}$)

N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and

—CH$_2$OCOR$^9$;

R$^9$, R$^{9'}$, R$^{10}$ and R$^{10'}$ are independently selected from hydrogen, C$_{1-4}$alkyl (optionally substituted by 1 or 2 R$^{13}$), —C(=O)O$^t$Bu, C$_{2-4}$alkenyl, cyano(C$_{1-4}$)alkyl and phenyl (optionally substituted by 1 or 2 groups selected from nitro, halo, hydroxy and cyano);

R$^{13}$ is selected from halo, trihalomethyl, and C$_{1-4}$alkoxy;

or a pharmaceutically acceptable salt or in vivo hydrolysable ester thereof.

Another preferred class of compound is of the formula (1) wherein:

Z is nitrogen;
R$^4$ and R$^5$ are together —S—C(R$^6$)=C(R$^7$)—;
R$^6$ is hydrogen or halo;
R$^7$ is hydrogen or halo;
A is phenylene;
n is 0, 1 or 2;
R$^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
r is 1 or 2;
Y is —OR$^3$;
R$^3$ is selected from hydrogen, C$_{1-4}$alkyl [optionally substituted by 1 or 2 R$^8$ groups], —COR$^8$ and —SO$_b$R$^8$ (wherein b is 0, 1 or 2);
R$^8$ is independently selected from hydrogen, hydroxy, C$_{1-4}$alkoxy, C$_{1-4}$alkoxyC$_{1-4}$alkyl, C$_{1-4}$alkoxyC$_{1-4}$alkoxy, hydroxyC$_{1-4}$alkoxy, C$_{1-4}$alkyl, amino(C$_{1-4}$)alkyl [optionally substituted on nitrogen by 1 or 2 groups selected from C$_{1-4}$alkyl, hydroxy(C$_{1-4}$)alkyl, dihydroxy(C$_{1-4}$)alkyl, —CO$_2$C$_{1-4}$alkyl, aryl and aryl(C$_{1-4}$)alkyl], C$_{2-4}$alkenyl, C$_{3-7}$cycloalkyl (optionally substituted by —C(O)O C$_{1-4}$alkyl), 5- and 6-membered cyclic acetals and mono- and di-methyl derivatives thereof, halo(C$_{1-4}$)alkyl, dihalo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$)alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and C$_{1-4}$alkyl), pyrazinyl, piperazinyl, 4-methylpiperazino, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), C$_{1-4}$alkylS(O)$_c$(C$_{1-4}$)alkyl (wherein c is 0, 1 or 2), —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and

—CH$_2$OCOR$^9$;

R$^9$, R$^{9'}$, R$^{10}$ and R$^{10'}$ are independently selected from hydrogen, C$_{1-4}$alkyl (optionally substituted by 1 or 2 R$^{13}$), —C(=O)O$^t$Bu, C$_{2-4}$alkenyl, cyano(C$_{1-4}$)alkyl and phenyl (optionally substituted by 1 or 2 groups selected from nitro, halo, hydroxy and cyano);

R$^{13}$ is selected from halo, trihalomethyl, and C$_{1-4}$alkoxy;

or a pharmaceutically acceptable salt or in vivo hydrolysable ester thereof.

A further preferred class of compound is of the formula (1) wherein;

Z is nitrogen;
R$^4$ and R$^5$ are together —C(R$^7$)=C(R$^6$)—S—;
R$^6$ is halo;
R$^7$ is hydrogen;
A is phenylene;
n is 0, 1 or 2;
R$^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
r is 1 or 2;
Y is —NR$^2$R;
R$^2$ and R$^3$ are independently selected from hydrogen, C$_{1-4}$alkyl [optionally substituted by 1 or 2 R$^8$ groups], —COR$^8$ and —SO$_b$R$^8$ (wherein b is 0, 1 or 2);
R$^8$ is independently selected from hydrogen, hydroxy, C$_{1-4}$alkoxy, C$_{1-4}$alkoxyC$_{1-4}$alkyl, C$_{1-4}$alkoxyC$_{1-4}$alkoxy, hydroxyC$_{1-4}$alkoxy, C$_{1-4}$alkyl, amino(C$_{1-4}$)alkyl [optionally substituted on nitrogen by 1 or 2 groups selected from C$_{1-4}$alkyl, hydroxy(C$_{1-4}$)alkyl, dihydroxy(C$_{1-4}$)alkyl, —CO$_2$C$_{1-4}$alkyl, aryl and aryl(C$_{1-4}$)alkyl], C$_{2-4}$alkenyl, C$_{3-7}$cycloalkyl (optionally substituted by —C(O)O C$_{1-4}$alkyl), 5- and 6-membered cyclic acetals and mono- and di-methyl derivatives thereof, halo(C$_{1-4}$)alkyl, dihalo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$)alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and C$_{1-4}$alkyl), pyrazinyl, piperazinyl, 4-methylpiperazino, C$_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), C$_{1-4}$alkylS(O)$_c$(C$_{1-4}$)alkyl (wherein c is 0, 1 or 2), —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and

—CH$_2$OCOR$^9$;

R$^9$, R$^{9'}$, R$^{10}$ and R$^{10'}$ are independently selected from hydrogen, C$_{1-4}$alkyl (optionally substituted by 1 or 2 R$^{13}$), —C(=O)O$^t$Bu, C$_{2-4}$alkenyl, cyano(C$_{1-4}$)alkyl and phenyl (optionally substituted by 1 or 2 groups selected from nitro, halo, hydroxy and cyano);

R$^{13}$ is selected from halo, trihalomethyl, and C$_{1-4}$alkoxy;

or a pharmaceutically acceptable salt or in vivo hydrolysable ester thereof.

Another preferred class of compound is of the formula (1) wherein:

Z is nitrogen;
R$^4$ and R$^5$ are together —C(R$^7$)=C(R$^6$)—S—;
R$^6$ is hydrogen or halo;

$R^7$ is hydrogen or halo;

A is phenylene;

n is 0, 1 or 2;

$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;

r is 1 or 2;

Y is —OR$^3$;

$R^3$ is selected from hydrogen, $C_{1-4}$alkyl [optionally substituted by 1 or 2 $R^8$ groups], —COR$^8$ and —SO$_b$R$^8$ (wherein b is 0, 1 or 2);

$R^8$ is independently selected from hydrogen, hydroxy, $C_{1-4}$alkoxy, $C_{1-4}$alkoxyC$_{1-4}$alkyl, $C_{1-4}$alkoxyC$_{1-4}$alkoxy, hydroxyC$_{1-4}$alkoxy, $C_{1-4}$alkyl, amino(C$_{1-4}$)alkyl [optionally substituted on nitrogen by 1 or 2 groups selected from $C_{1-4}$alkyl, hydroxy(C$_{1-4}$)alkyl, dihydroxy(C$_{1-4}$)alkyl, —CO$_2$C$_{1-4}$alkyl, aryl and aryl(C$_{1-4}$)alkyl], C$_{2-4}$alkenyl, C$_{3-7}$cycloalkyl (optionally substituted by —C(O)O C$_{1-4}$alkyl), 5- and 6-membered cyclic acetals and mono- and di-methyl derivatives thereof, halo(C$_{1-4}$)alkyl, dihalo(C$_{1-4}$) alkyl, trihalo(C$_{1-4}$)alkyl, hydroxy(C$_{1-4}$)alkyl, dihydroxy (C$_{1-4}$)alkyl, cyano(C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$)alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), C$_{1-4}$alkylS(O)$_c$(C$_{1-4}$)alkyl (wherein c is 0, 1 or 2), —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and

—CH$_2$OCOR$^9$;

$R^9$, $R^{9'}$, $R^{10}$ and $R^{10'}$ are independently selected from hydrogen, $C_{1-4}$alkyl (optionally substituted by 1 or 2 $R^{13}$), —C(=O)O$^t$Bu, C$_{2-4}$alkenyl, cyano(C$_{1-4}$)alkyl, phenyl (optionally substituted by 1 or 2 groups selected from nitro, halo, hydroxy and cyano);

$R^{13}$ is selected from halo, trihalomethyl, and $C_{1-4}$alkoxy;

or a pharmaceutically acceptable salt or in vivo hydrolysable ester thereof;

A further preferred class of compound is of the formula (1) wherein;

Z is nitrogen;

$R^4$ and $R^5$ are together —C(R$^7$)=C(R$^6$)—S—;

$R^6$ is halo;

$R^7$ is hydrogen;

A is phenylene;

n is 0;

r is 1;

Y is —NR$^2$R$^3$;

$R^2$ is hydrogen or $C_{1-4}$alkyl;

$R^3$ is selected from $C_{1-4}$alkyl [optionally substituted by 1 or 2 $R^8$ groups], —COR$^8$ and —SO$_b$R$^8$ (wherein b is 0, 1 or 2);

$R^8$ is independently selected from hydrogen, hydroxy, $C_{1-4}$alkoxy, $C_{1-4}$alkoxyC$_4$alkyl, $C_{1-4}$alkyl, amino(C$_{1-4}$)alkyl [optionally substituted on nitrogen by 1 or 2 groups selected from $C_{1-4}$alkyl, hydroxy(C$_{1-4}$)alkyl, dihydroxy(C$_{1-4}$)alkyl, —CO$_2$C$_{1-4}$alkyl, phenyl and aryl(C$_{1-4}$)alkyl], C$_{2-4}$alkenyl, C$_{3-7}$cycloalkyl (optionally substituted by —C(O)O C$_{1-4}$alkyl), 5- and 6-membered cyclic acetals and mono- and di-methyl derivatives thereof, halo(C$_{1-4}$)alkyl, trihalo(C$_{1-4}$) alkyl, hydroxy(C$_{1-4}$)alkyl, dihydroxy(C$_{1-4}$)alkyl, cyano (C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$)alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), C$_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), —CH$_2$CH(NR$^9$R$^{10}$)CO(NR$^{9'}$R$^{10'}$), —CH$_2$OR$^9$, (R$^9$)(R$^{10}$) N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and —CH$_2$OCOR$^9$;

$R^9$, $R^{9'}$, $R^{10}$ and $R^{10'}$ are independently selected from hydrogen, $C_{1-4}$alkyl (optionally substituted by 1 or 2 hydroxy groups), C$_{2-4}$alkenyl, and phenyl (optionally substituted by 1 or 2 groups selected from nitro, halo, hydroxy and cyano);

or a pharmaceutically acceptable salt or in vivo hydrolysable ester thereof.

A further preferred class of compound is of the formula (1) wherein;

Z is nitrogen;

$R^4$ and $R^5$ are together —S—C(R$^6$)=C(R$^7$)—;

$R^6$ is halo;

$R^7$ is hydrogen;

A is phenylene;

n is 0 r is 1;

Y is —NR$^2$R$^3$;

$R^2$ is hydrogen or $C_{1-4}$alkyl;

$R^3$ is selected from $C_{1-4}$alkyl [optionally substituted by 1 or 2 $R^8$ groups], —COR$^8$ and —SO$_b$R$^8$ (wherein b is 0, 1 or 2);

$R^8$ is independently selected from hydrogen, hydroxy, $C_{1-4}$alkoxy, $C_{1-4}$alkoxyC$_{1-4}$alkyl, $C_{1-4}$alkyl, amino(C$_{1-4}$) alkyl [optionally substituted on nitrogen by 1 or 2 groups selected from $C_{1-4}$alkyl, hydroxy(C$_{1-4}$)alkyl, dihydroxy (C$_{1-4}$)alkyl, —CO$_2$C$_{1-4}$alkyl, phenyl and aryl(C$_{1-4}$)alkyl], C$_{2-4}$alkenyl, C$_{3-7}$cycloalkyl (optionally substituted by —C(O)OC$_{1-4}$alkyl), 5- and 6-membered cyclic acetals and mono- and di-methyl derivatives thereof, halo(C$_{1-4}$)alkyl, trihalo(C$_{1-4}$)alkyl, hydroxy(C$_{1-4}$)alkyl, dihydroxy(C$_{1-4}$) alkyl, cyano(C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$) alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2-CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and —CH$_2$OCOR$^9$;

$R^9$, $R^{9'}$, $R^{10}$ and $R^{10'}$ are independently selected from hydrogen, $C_{1-4}$alkyl (optionally substituted by 1 or 2 hydroxy groups), $C_{2-4}$alkenyl, and phenyl (optionally substituted by 1 or 2 groups selected from nitro, halo, hydroxy and cyano);

or a pharmaceutically acceptable salt or in vivo hydrolysable ester thereof.

In a further preferred aspect of the invention is provided a compound of the formula (1A):

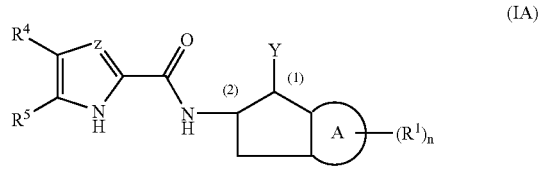

(IA)

wherein Z is CH;
$R^4$ and $R^5$ are together —S—C(R$^6$)=C(R$^7$)— or —C(R$^7$)=C(R$^6$)—S—;
$R^6$ is hydrogen or halo;
$R^7$ is hydrogen or halo;
A is phenylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
Y is —NR$^2$R$^3$ or OR$^3$;
$R^2$ is hydrogen or $C_{1-4}$alkyl;
$R^3$ is selected from $C_{1-4}$alkyl [optionally substituted by 1 or 2 $R^8$ groups], —COR$^8$ and —SO$_b$R$^8$ (wherein b is 0, 1 or 2);
$R^8$ is independently selected from hydrogen, hydroxy, $C_{1-4}$alkoxy, $C_{1-4}$alkoxyC$_{1-4}$alkyl, $C_{1-4}$alkyl, amino(C$_{1-4}$)alkyl [optionally substituted on nitrogen by 1 or 2 groups selected from $C_{1-4}$alkyl, hydroxy(C$_{1-4}$)alkyl, dihydroxy(C$_{1-4}$)alkyl, —CO$_2$C$_{1-4}$alkyl, phenyl and aryl(C$_{1-4}$)alkyl], $C_{2-4}$alkenyl, $C_{3-7}$cycloalkyl (optionally substituted by —C(O)OC$_{1-4}$alkyl), 5- and 6-membered cyclic acetals and mono- and di-methyl derivatives thereof, halo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$)alkyl, furyl (optionally substituted on carbon by 1 or 2 nitro groups), thienyl (optionally substituted on carbon by 1 or 2 nitro groups), morpholino, furyl(C$_{1-4}$)alkyl (wherein furyl is optionally substituted on carbon by 1 or 2 nitro groups), thienyl(C$_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxotetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkylS(O)$_b$— (wherein b is 0, 1 or 2), $C_{3-6}$cycloalkylS(O)$_b$— (wherein b is 0, 1 or 2), arylS(O)$_b$— wherein b is 0, 1 or 2), heterocyclylS(O)$_b$— (wherein b is 0, 1 or 2) —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and —CH$_2$OCOR$^9$;

$R^9$, $R^{9'}$, $R^{10}$ and $R^{10'}$ are independently selected from hydrogen, $C_{1-4}$alkyl (optionally substituted by 1 or 2 hydroxy groups), $C_{2-4}$alkenyl, and phenyl (optionally substituted by 1 or 2 groups selected from nitro, halo, hydroxy and cyano);

or a pharmaceutically acceptable salt or in vivo hydrolysable ester thereof.

A further preferred class of compound is of the formula (1) wherein;
Z is CH;
$R^4$ and $R^5$ are together —S—C(R$^6$)=C(R$^7$)— or —C(R$^7$)=C(R$^6$)—S—;
$R^6$ is halo or hydrogen;
$R^7$ is halo or hydrogen;
A is heteroarylene;
n is 0, 1 or 2;
$R^1$ is independently selected from halo, cyano, nitro, hydroxy, methyl, fluoromethyl, difluoromethyl, trifluoromethyl, methoxy, —SMe, —SOMe, —SO$_2$Me and, (when n is 2) methylenedioxy;
r is 1 or 2;
Y is —NR$^2$R$^3$ or —OR$^3$;
$R^2$ and $R^3$ are independently selected from hydrogen, $C_{1-4}$alkyl [optionally substituted by 1 or 2 $R^8$ groups], $C_{3-7}$cycloalkyl (optionally substituted with 1 or 2 hydroxy groups), phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl, —COR$^8$ and —SO$_b$R$^8$ (wherein b is 0, 1 or 2);
$R^8$ is independently selected from hydrogen, hydroxy, $C_{1-4}$alkoxy, $C_{1-4}$alkoxyC$_{1-4}$alkyl, $C_{1-4}$alkoxyC$_{1-4}$alkoxy, hydroxyC$_{1-4}$alkoxy, $C_{1-4}$alkyl, amino(C$_{1-4}$)alkyl [optionally substituted on nitrogen by 1 or 2 groups selected from $C_{1-4}$alkyl, hydroxy(C$_{1-4}$)alkyl, dihydroxy(C$_{1-4}$)alkyl, —CO$_2$C$_{1-4}$alkyl, aryl and aryl(C$_{1-4}$)alkyl], $C_{2-4}$alkenyl, $C_{3-7}$cycloalkyl (optionally substituted by —C(O)O C$_{1-4}$alkyl), 5- and 6-membered cyclic acetals and mono- and di-methyl derivatives thereof, halo(C$_{1-4}$)alkyl, dihalo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$)alkyl, heterocyclyl, heterocyclyl $C_{1-4}$alkyl, aryl, $C_{1-4}$alkylS(O)$_b$— (wherein b is 0, 1 or 2), $C_{3-6}$cycloalkylS(O)$_b$— (wherein b is 0, 1 or 2), arylS(O)$_b$— (wherein b is 0, 1 or 2), heterocyclylS(O)$_b$— (wherein b is 0, 1 or 2), benzylS(O)$_b$— (wherein b is 0, 1 or 2), $C_{1-4}$alkylS(O)$_c$(C$_{1-4}$)alkyl (wherein c is 0, 1 or 2), —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$ and —CH$_2$OCOR$^9$;

$R^9$, $R^{9'}$, $R^{10}$ and $R^{10'}$ are independently selected from hydrogen, $C_{1-4}$alkyl (optionally substituted by 1 or 2 $R^{13}$), $C_{3-7}$cycloalkyl (optionally substituted by 1 or 2 hydroxy groups), —C(=O)O$^t$Bu, $C_{2-4}$alkenyl, cyano(C$_{1-4}$)alkyl, phenyl (optionally substituted by 1 or 2 groups selected from nitro, halo, hydroxy and cyano); or $R^9$ and $R^{10}$ together with the nitrogen to which they are attached, and/or $R^{9'}$ and $R^{10'}$, together with the nitrogen to which they are attached, form a 4- to 6-membered ring where the ring is optionally substituted on carbon by 1 or 2 substituents independently selected from oxo, hydroxy, carboxy, halo, nitro, cyano, carbonyl and $C_{1-4}$alkoxy; or the ring may be optionally substituted on two adjacent carbons by —O—$CH_2$—O— to form a cyclic acetal wherein one or both of the hydrogens of the —O—$CH_2$—O— group may be replaced by a methyl;

$R^{13}$ is selected from halo, trihalomethyl, and $C_{1-4}$alkoxy;

or a pharmaceutically acceptable salt or in vivo hydrolysable ester thereof

A preferred class of compound is of the formula (1) wherein;

Z is CH;

$R^4$ and $R^5$ are together —S—$C(R^6)$=$C(R^7)$—;

$R^6$ is halo or hydrogen;

$R^7$ is halo or hydrogen;

A is phenylene;

n is 1 or 2;

$R^1$ is independently selected from hydrogen, halo, cyano, nitro, hydroxy, fluoromethyl, difluoromethyl, trifluoromethyl, $C_{1-4}$alkoxy and and $R^1$ is of the formula A' or A":

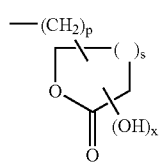

(A)

(A')

wherein x is 0 or 1, p is 0, 1, 2 or 3 and s is 1 or 2; provided that the hydroxy group is not a substituent on the ring carbon adjacent to the ring oxygen;

r is 1 or 2;

Y is —$NR^2R^3$ or —$OR^3$;

$R^2$ and $R^3$ are independently selected from hydrogen, hydroxy, $C_{1-4}$alkyl (optionally substituted by 1 or 2 hydroxy groups provided that when there are 2 hydroxy groups they are not substituents on the same carbon), $C_{5-7}$cycloalkyl (optionally substituted with 1 or 2 hydroxy groups provided that when there are 2 hydroxy groups they are not substituents on the same carbon), cyano($C_{1-4}$)alkyl, fluoromethylcarbonyl, difluoromethylcarbonyl, trifluoromethylcarbonyl, $C_{1-4}$alkyl [substituted by 1 or 2 $R^8$ groups (provided that when there are 2 $R^8$ groups they are not substituents on the same carbon)], —$COR^8$ and —$SO_bR^8$ (wherein b is 0, 1 or 2);

{wherein $R^8$ is independently selected from hydrogen, hydroxy, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, morpholino, pyridyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkyl, $C_{2-4}$alkenyl, cyclo($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_4$alkyl, hydroxy, hydroxy($C_{1-4}$)alkyl, dihydroxy($C_{1-4}$)alkyl, aryl and aryl($C_{1-4}$)alkyl), $C_{1-4}$alkylS(O)$_c$($C_{1-4}$)alkyl (wherein c is 0, 1 or 2), —$CH_2CH(CO_2R^9)N(R^9R^{10})$, —$CH_2OR^9$, $(R^9)(R^{10})N$—, —$COOR^9$, —$CH_2COOR^9$, —$CH_2CONR^9R^{10}$, and —$CH_2CH_2CH(NR^9R^{10})CO_2R^9$; [wherein $R^9$ and $R^{10}$ are independently selected from hydrogen, $C_{1-4}$alkyl (optionally substituted by 1 or 2 hydroxy groups provided that when there are 2 hydroxy groups they are not substituents on the same carbon), $C_{5-7}$cycloalkyl (optionally substituted by 1 or 2 hydroxy groups provided that when there are 2 hydroxy groups they are not substituents on the same carbon), $C_{2-4}$alkenyl, cyano($C_{1-4}$)alkyl, phenyl (optionally substituted by 1 or 2 groups selected from nitro, halo, hydroxy and cyano) and $C_{1-4}$alkyl substituted by $R^{13}$;

(wherein $R^{13}$ is selected from $C_{1-4}$alkoxy, furyl (optionally substituted on carbon by 1 or 2 nitro groups), thienyl (optionally substituted on carbon by 1 or 2 nitro groups), morpholino, furyl($C_4$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, $C_{1-4}$alkylS(O)$_d$($C_{1-4}$)alkyl (wherein d is 0, 1 or 2)); and $R^9$ and $R^{10}$ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N—$C_{1-4}$alkylamino, N,N—($C_{1-4}$)$_2$alkylamino, carbonyl, sulfo, $C_{1-4}$alkoxy, heterocyclyl, $C_{1-4}$alkanoyl, and $C_{1-4}$alkylS(O)$_f$($C_4$)alkyl (wherein f is 0, 1 or 2)]};

or a pharmaceutically acceptable salt or in vivo hydrolysable ester thereof;

with the proviso that the compound of formula (1) is not:

i) 2,3-dichloro-5-(N-{1-[N-(1,1-dimethylethoxy)carbonylamino]indan-2-yl}carbamoyl)4H-thieno[3,2-b]pyrrole;

ii) 5-[N-(1-aminoindan-2-yl)carbamoyl]-2,3-dichloro-4H-thieno[3,2-b]pyrrole;

iii) 5-[N-(1-acetamidoindan-2-yl)carbamoyl]-2,3-dichloro-4H-thieno[3,2-b]pyrrole;

iv) 2,3-dichloro-5-{N-[1-(methanesulphonamido)indan-2-yl]carbamoyl}-4H-thieno[3,2-b]pyrrole;

v) 2,3-dichloro-5-{N-[1-(methylamino)indan-2-yl]carbamoyl}4H-thieno[3,2-b]pyrrole;

vi) 2,3-dichloro-5-{N-[1-(methylacetamido)indan-2-yl]carbamoyl}-4H-thieno[3,2-b]pyrrole;

vii) 2,3-dichloro-5-[N-(1-hydroxyindan-2-yl)carbamoyl]-4H-thieno[3,2-b]pyrrole;

viii) 2,3-dichloro-5-[N-(6-fluoro-1-hydroxyindan-2-yl)carbamoyl]-4H-thieno[3,2-b]pyrrole;

ix) 2,3-dichloro-5-[N-(1-methoxyindan-2-yl)carbamoyl]-4H-thieno[3,2-b]pyrrole;

x) 2,3-dichloro-5-[N-(1-hydroxy-1,2,3,4-tetrahydronaphth-2-yl)carbamoyl]-4H-thieno[3,2-b]pyrrole.

Another preferred class of compounds is of formula (1) wherein:

Z is CH;

R⁴ and R⁵ are together —C(R⁷)=C(R⁶)—S—;

R⁶ is chloro;

R⁷ is hydrogen;

A is phenylene;

n is 1 or 2;

R¹ is independently selected from hydrogen, halo, nitro, hydroxy, $C_{1-4}$alkyl, $C_{1-4}$alkoxy and and R¹ is of the formula A' or A":

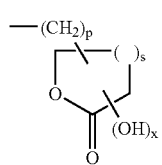
(A)

—CH₂CH(OH)(CH₂)$_u$CO₂H         (A')

wherein x is 0 or 1, p is 0, 1, 2 or 3 and s is 1 or 2; provided that the hydroxy group is not a substituent on the ring carbon adjacent to the ring oxygen;

r is 1 or 2;

Y is —NR²R³ or —OR³;

R² and R³ are independently selected from hydrogen, $C_{1-4}$alkyl (optionally substituted by 1 or 2 hydroxy groups provided that when there are 2 hydroxy groups they are not substituents on the same carbon), $C_{5-7}$cycloalkyl (optionally substituted with 1 or 2 hydroxy groups provided that when there are 2 hydroxy groups they are not substituents on the same carbon), cyano($C_{1-4}$)alkyl, fluoromethylcarbonyl, difluoromethylcarbonyl, trifluoromethylcarbonyl, $C_{1-4}$alkyl [substituted by 1 or 2 R⁸ groups (provided that when there are 2 R⁸ groups they are not substituents on the same carbon)], —COR⁸ and —SO$_b$R⁸ (wherein b is 0, 1 or 2);

{wherein R⁸ is independently selected from hydrogen, hydroxy, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, $C_{1-4}$alkyl, $C_{2-4}$alkenyl, cyclo($C_{3-8}$) alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), $C_{1-4}$alkylS(O)C($C_{1-4}$)alkyl (wherein c is 0, 1 or 2), —CH₂CH(CO₂R⁹)N(R⁹R¹⁰), —CH₂OR⁹, (R⁹)(R¹⁰)N—, —COOR⁹ and —CH₂COOR⁹, —CH₂CONR⁹R¹⁰, —CH₂CH₂CH(NR⁹R¹⁰)CO₂R⁹;

[wherein R⁹ and R¹⁰ are independently selected from hydrogen, $C_{1-4}$alkyl (optionally substituted by 1 or 2 hydroxy groups provided that when there are 2 hydroxy groups they are not substituents on the same carbon), $C_{5-7}$cycloalkyl (optionally substituted by 1 or 2 hydroxy groups provided that when there are 2 hydroxy groups they are not substituents on the same carbon), $C_{2-4}$alkenyl, cyano ($C_{1-4}$) alkyl, phenyl (optionally substituted by 1 or 2 groups selected from nitro, halo, hydroxy and cyano) and $C_{1-4}$alkyl substituted by R¹³;

(wherein R¹³ is selected from $C_{1-4}$alkoxy, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$) alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, $C_{1-4}$alkylS(O)$_d$($C_{1-4}$)alkyl (wherein d is 0, 1 or 2)); and R⁹ and R¹⁰ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N—$C_{1-4}$alkylamino, N,N—($C_{1-4}$)₂alkylamino, carbonyl, sulfo, $C_{1-4}$alkoxy, heterocyclyl, $C_{1-4}$alkanoyl, and $C_{1-4}$alkylS(O)$_f$($C_{1-4}$)alkyl (wherein f is 0, 1 or 2)]};

or a pharmaceutically acceptable salt or in vivo hydrolysable ester thereof;

with the proviso that the compound of formula (1) is not:
2-chloro-5-[N-(1-hydroxyindan-2-yl)carbamoyl]-6H-thieno[2,3-b]pyrrole.

In another aspect of the invention, preferred compounds of the invention are any one of:

2,3-dichloro-N-[(1R,2R)-1-(formylamino)-2,3-dihydro-1H-inden-2-yl]-4H-thieno[3,2-b]pyrrole-5-carboxamide;

2,3-dichloro-N-((1R,2R)-1-{[(methyloxy)acetyl]amino}-2,3-dihydro-1H-inden-2-yl)-4H-thieno[3,2-b]pyrrole-5-carboxamide;

N-((1S,2S)-1-{[(3R)-3-(tert-butoxycarbonylamino)-3-carbamoylpropanoyl]amino}-2,3-dihydro-1H-inden-2-yl)-2,3-dichloro-4H-thieno[3,2-b]pyrrole-5-carboxamide;

2,3-dichloro-N-[(1R,2R)-1-({[(4R)-2,2-dimethyl-5-oxo-1,3-dioxolan-4-yl]acetyl}amino)-2,3-dihydro-1H-inden-2-yl]-4H-thieno[3,2-b]pyrrole-5-carboxamide;

2,3-dichloro-N-{(1R,2R)-1-[(3-methoxypropanoyl)amino]-2,3-dihydro-1H-inden-2-yl}-4H-thieno[3,2-b]pyrrole-5-carboxamide;

N-{(1R,2R)-1-[(2-acetoxyacetyl)amino]-2,3-dihydro-1H-inden-2-yl}-2,3-dichloro-4H-thieno[3,2-b]pyrrole-5-carboxamide;

N-{(1R,2R)-1-[(2-carbamoylacetyl)amino]-2,3-dihydro-1H-inden-2-yl}-2,3-dichloro-4H-thieno[3,2-b]pyrrol-5-carboxamide;

2,3-dichloro-N-{(1R,2R)-1-[(trifluoroacetyl)amino]-2,3-dihydro-1H-inden-2-yl}-4H-thieno[3,2-b]pyrrole-5-carboxamide;

2,3-dichloro-N-{(1S,2S)-1-[(furan-2-ylcarbonyl)amino]-2,3-dihydro-1H-inden-2-yl}-4H-thieno[3,2-b]pyrrole-5-carboxamide;

2,3-dichloro-N-{(1S,2S)-1-[(furan-3-ylcarbonyl)amino]-2,3-dihydro-1H-inden-2-yl}-4H-thieno[3,2-b]pyrrole-5-carboxamide;

2,3-dichloro-N-{(1S,2S)-1-[(3-thienylcarbonyl)amino]-2,3-dihydro-1H-inden-2-yl}-4H-thieno[3,2-b]pyrrole-5-carboxamide;

2,3-dichloro-N-((1S,2S)-1-{[(5-nitrofuran-2-yl)carbonyl]amino}-2,3-dihydro-1H-inden-2-yl)-4H-thieno[3,2-b]pyrrole-5-carboxamide;

2,3-dichloro-N-{(1S,2S)-1-[(pyridin-3-ylcarbonyl)amino]-2,3-dihydro-1H-inden-2-yl}-4H-thieno[3,2-b]pyrrole-5-carboxamide;

N-[(1S,2S)-1-(acryloylamino)-2,3-dihydro-1H-inden-2-yl]-2,3-dichloro-4H-thieno[3,2-b]pyrrole-5-carboxamide;

2,3-dichloro-N-((1S,2S)-1-{[(3-hydroxyphenyl)carbonyl]amino}-2,3-dihydro-1H-inden-2-yl)-4H-thieno[3,2-b]pyrrole-5-carboxamide;

N-[(1S,2S)-1-(acetylamino)-2,3-dihydro-1H-inden-2-yl]-2,3-dichloro-4H-thieno[3,2-b]pyrrole-5-carboxamide;

N-[(1S,2S)-1-[(2-carboxyacetyl)amino]-2,3-dihydro-1H-inden-2-yl]-2,3-dichloro-4H-thieno[3,2-b]pyrrole-5-carboxamide;

2,3-dichloro-N-((1S,2S)-1-{[(dimethylamino)carbonyl]amino}-2,3-dihydro-1H-inden-2-yl)-4H-thieno[3,2-b]pyrrole-5-carboxamide;

2,3-dichloro-N-((1S,2S)-1-{[(4-methylpiperazin-1-yl)carbonyl]amino}-2,3-dihydro-1H-inden-2-yl)-4H-thieno[3,2-b]pyrrole-5-carboxamide;

2,3-dichloro-N-((1S,2S)-1-{[(ethylamino)carbonyl]amino}-2,3-dihydro-1H-inden-2-yl)-4H-thieno[3,2-b]pyrrole-5-carboxamide;

2,3-dichloro-N-((1S,2S)-1-{[(prop-2-en-1-ylamino)carbonyl]amino}-2,3-dihydro-1H-inden-2-yl)-4H-thieno[3,2-b]pyrrole-5-carboxamide;

2,3-dichloro-N-[(1S,2S)-1-({[(3,5-dinitrophenyl)amino]carbonyl}amino)-2,3-dihydro-1H-inden-2-yl]-4H-thieno[3,2-b]pyrrole-5-carboxamide;

2,3-dichloro-N-[(1S,2S)-1-(formylamino)-2,3-dihydro-1H-inden-2-yl]-4H-thieno[3,2-b]pyrrole-5-carboxamide;

N-{(1R,2R)-1-[((3R)-3-amino-3-carbamoylpropanoyl)amino]-2,3-dihydro-1H-inden-2-yl}-2,3-dichloro-4H-thieno[3,2-b]pyrrole-5-carboxamide;

N-{(1R,2R)-1-[((3R)-3-carboxy-3-hydroxypropanoyl)amino]-2,3-dihydro-1H-inden-2-yl}-2,3-dichloro-4H-thieno[3,2-b]pyrrole-5-carboxamide;

2,3-dichloro-N-{(1R,2R)-1-[(hydroxyacetyl)amino]-2,3-dihydro-1H-inden-2-yl}-4H-thieno[3,2-b]pyrrole-5-carboxamide;

2,3-dichloro-N-{(1S,2S)-1-[(methylsulfonyl)amino]-2,3-dihydro-1H-inden-2-yl}-4H-thieno[3,2-b]pyrrole-5-carboxamide;

2,3-dichloro-N-{(1S,2S)-1-[methyl(morpholin-4-ylacetyl)amino]-2,3-dihydro-1H-inden-2-yl}-4H-thieno[3,2-b]pyrrole-5-carboxamide;

N-{(1R,2R)-1-[(2-amino-2-oxoethyl)amino]-2,3-dihydro-1H-inden-2-yl}-2,3-dichloro-4H-thieno[3,2-b]pyrrole-5-carboxamide;

N-{(1R,2R)-1-[(tert-butoxycarbonylmethyl)amino]-2,3-dihydro-1H-inden-2-yl}-2,3-dichloro-4H-thieno[3,2-b]pyrrole-5-carboxamide;

N-[(1R,2R)-1-(carboxymethylamino)-2,3-dihydro-1H-inden-2-yl]-2,3-dichloro-4H-thieno[3,2-b]pyrrole-5-carboxamide;

N-{(1R,2R)-1-[N-acetyl-N-(carboxymethyl)amino]-2,3-dihydro-1H-inden-2-yl}-2,3-dichloro-4H-thieno[3,2-b]pyrrole-5-carboxamide;

N-{(1R,2R)-1-[acetyl(2-amino-2-oxoethyl)amino]-2,3-dihydro-1H-inden-2-yl}-2,3-dichloro-4H-thieno[3,2-b]pyrrole-5-carboxamide;

N-{(1R,2R)-1-[N-(carboxymethyl)-N-(hydroxyacetyl)amino]-2,3-dihydro-1H-inden-2-yl}-2,3-dichloro-4H-thieno[3,2-b]pyrrole-5-carboxamide;

2-chloro-N-[(1R,2R)-1-({[(2S)-5-oxotetrahydrofuran-2-yl]carbonyl}amino)-2,3-dihydro-1H-inden-2-yl]-6H-thieno[2,3-b]pyrrole-5-carboxamide;

2-chloro-N-[(1R,2R)-1-(formylamino)-2,3-dihydro-1H-inden-2-yl]-6H-thieno[2,3-b]pyrrole-5-carboxamide;

2-chloro-N-{(1R,2R)-1-[(methoxyacetyl)amino]-2,3-dihydro-1H-inden-2-yl}-6H-thieno[2,3-b]pyrrole-5-carboxamide;

N-[(1R,2R)-1-(acetylamino)-2,3-dihydro-1H-inden-2-yl]-2-chloro-6H-thieno[2,3-b]pyrrole-5-carboxamide;

2-chloro-N-{(1R,2R)-1-[(3-methoxypropanoyl)amino]-2,3-dihydro-1H-inden-2-yl}-6H-thieno[2,3-b]pyrrole-5-carboxamide;

N-{(1R,2R)-1-[(2-acetoxyacetyl)amino]-2,3-dihydro-1H-inden-2-yl}-2-chloro-6H-thieno[2,3-b]pyrrole-5-carboxamide;

N-((1R,2R)-1-{[(3R)-3-(tert-butoxycarbonylamino)-3-carbamoylpropanoyl]amino}-2,3-dihydro-1H-inden-2-yl)-2-chloro-6H-thieno[2,3-b]pyrrole-5-carboxamide;

N-{(1R,2R)-1-[2-(tert-butoxycarbonylamino)acetylamino]-2,3-dihydra-1H-inden-2-yl}-2-chloro-6H-thieno[2,3-b]pyrrole-5-carboxamide;

N-{(1R,2R)-1-[(2-carbamoylacetyl)amino]-2,3-dihydro-1H-inden-2-yl}-2-chloro-6H-thieno[2,3-b]pyrrole-5-carboxamide;

N-{(1R,2R)-1-[2-(tert-butoxycarbonyl)acetylamino]-2,3-dihydro-1H-inden-2-yl}-2-chloro-6H-thieno[2,3-b]pyrrole-5-carboxamide;

2-chloro-N-((1R,2R)-1-{[3-hydroxy-2-(hydroxymethyl)propanoyl]amino}-2,3-dihydro-1H-inden-2-yl)-6H-thieno[2,3-b]pyrrole-5-carboxamide;

N-{(1R,2R)-1-[((3R)-3-amino-3-carbamoylpropanoyl)amino]-2,3-dihydro-1H-inden-2-yl}-2-chloro-6H-thieno[2,3-b]pyrrole-5-carboxamide;

N-{(1R,2R)-1-[(aminoacetyl)amino]-2,3-dihydro-1H-inden-2-yl}-2-chloro-6H-thieno[2,3-b]pyrrole-5-carboxamide;

2-chloro-N-[(1R,2R)-1-({[(2-hydroxyethyl)(phenylmethyl)amino]acetyl}amino)-2,3-dihydro-1H-inden-2-yl]-6H-thieno[2,3-b]pyrrole-5-carboxamide;

2-chloro-N-{(1R,2R)-1-[(morpholin-4-ylacetyl)amino]-2,3-dihydro-1H-inden-2-yl}-6H-thieno[2,3-b]pyrrole-5-carboxamide;

2-chloro-N-((1R,2R)-1-({[(2-hydroxyethyl)(methyl)amino]acetyl}amino)-2,3-dihydro-1H-inden-2-yl)-6H-thieno[2,3-b]pyrrole-5-carboxamide;

N-((1R,2R)-1-({[bis(2-hydroxyethyl)amino]acetyl}amino)-2,3-dihydro-1H-inden-2-yl)-2-chloro-6H-thieno[2,3-b]pyrrole-5-carboxamide;

2-chloro-N-((1R,2R)-1-({[ethyl(2-hydroxyethyl)amino]acetyl}amino)-2,3-dihydro-1H-inden-2-yl)-6H-thieno[2,3-b]pyrrole-5-carboxamide;

2-chloro-N-((1R,2R)-1-({[(2,3-dihydroxypropyl)(methyl)amino]acetyl}amino)-2,3-dihydro-1H-inden-2-yl)-6H-thieno[2,3-b]pyrrole-5-carboxamide;

N-((1R,2R)-1-({[bis(2-hydroxypropyl)amino]acetyl}amino)-2,3-dihydro-1H-inden-2-yl)-2-chloro-6H-thieno[2,3-b]pyrrole-5-carboxamide;

N-{(1R,2R)-1-[(2-amino-2-oxoethyl)amino]-2,3-dihydro-1H-inden-2-yl}-2-chloro-6H-thieno[2,3-b]pyrrole-5-carboxamide;

N-{(1R,2R)-1-[(tert-butoxycarbonylmethyl)amino]-2,3-dihydro-1H-inden-2-yl}-2-chloro-6H-thieno[2,3-b]pyrrole-5-carboxamide;

N-{(1R,2R)-1-(carboxymethylamino)-2,3-dihydro-1H-inden-2-yl}-2-chloro-6H-thieno[3,2-b]pyrrole-5-carboxamide;

2-chloro-N-{(1R,2R)-1-[(hydroxyacetyl)amino]-2,3-dihydro-1H-inden-2-yl}-6H-thieno[2,3-b]pyrrole-5-carboxamide;

2,3-dichloro-N-{(1R,2R)-1-[(chloroacetyl)amino]-2,3-dihydro-1H-inden-2-yl}-4H-thieno[3,2-b]pyrrole-5-carboxamide;
N-{(1R,2R)-1-[((3S)-3-amino-3-carboxypropanoyl)amino]-2,3-dihydro-1H-inden -2-yl}-2,3-dichloro-4H-thieno[3,2b]pyrrole-5-carboxamide;
N-{(1R,2R)-1-[(2-carboxyacetyl)amino]-2,3-dihydro-1H-inden-2-yl}-2,3-dichloro -4H-thieno[3,2-b]pyrrole-5-carboxamide;
N-{(1R,2R)-1-[(2-carboxyacetyl)amino]-2,3-dihydro-1H-inden-2-yl}-2-chloro-6H-thieno[3,2-b]pyrrole-5-carboxamide;
N-{(1R,2R)-1-[((3S)-3-amino-3-carboxypropanoyl)amino]-2,3-dihydro-1H-inden -2-yl}-2-chloro-6H-thieno[3,2-b]pyrrole-5-carboxaminde;
2,3-dichloro-N-{(1R,2R)-1-[(methylsulfonyl)amino]-2,3-dihydro-1H-inden-2-yl}4H-thieno[3,2-b]pyrrole-5-carboxamide;

or a pharmaceutically acceptable salt or an in vivo hydrolysable ester thereof.

In another aspect of the invention, further preferred compounds of the invention are any one of:
2-chloro-N-{(1R,2R)-1-[(hydroxyacetyl)amino]-2,3-dihydro-1H-inden-2-yl}-6H-thieno[2,3-b]pyrrole-5-carboxamide;
N-{(1R,2R)-1-[(2-amino-2-oxoethyl)amino]-2,3-dihydro-1H-inden-2-yl}-2,3-dichloro-4H-thieno[3,2-b]pyrrole-5-carboxamide;
2,3-dichloro-N-{(1R,2R)-1-[(hydroxyacetyl)amino]-2,3-dihydro-1H-inden-2-yl}-4H-thieno[3,2-b]pyrrole-5-carboxamide;
2,3-dichloro-N-[(1R,2R)-1-(formylamino)-2,3-dihydro-1H-inden-2-yl]4H-thieno[3,2-b]pyrrole-5-carboxamide;

or a pharmaceutically acceptable salt or an in vivo hydrolysable ester thereof.

Another aspect of the present invention provides a process for preparing a compound of formula (1) or a pharmaceutically acceptable salt or an in vivo hydrolysable ester thereof which process (wherein A, Y, $R^1$, $R^4$, $R^5$, r and n are, unless otherwise specified, as defined in formula (1)) comprises of:
a) reacting an acid of the formula (2):

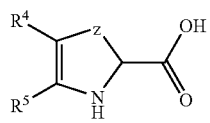

(2)

or an activated derivative thereof; with an amine of formula (3):

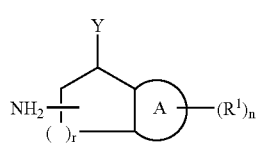

(3)

and thereafter if necessary:
i) converting a compound of the formula (1) into another compound of the formula (1);

ii) removing any protecting groups;
iii) forming a pharmaceutically acceptable salt or in vivo hydrolysable ester.

Specific reaction conditions for the above reaction are as follows.

Process a) Acids of formula (2) and amines of formula (3) may be coupled together in the presence of a suitable coupling reagent. Standard peptide coupling reagents known in the art can be employed as suitable coupling reagents, or for example carbonyldiimidazole, 1-ethyl-3-(3-dimethylaminopropyl)carbodi-imide hydrochloride (EDCI) and dicyclohexyl-carbodiimide (DCCI), optionally in the presence of a catalyst such as 1-hydroxybenzotriazole, dimethylaminopyridine or 4-pyrrolidinopyridine, optionally in the presence of a base for example triethylamine, di-isopropylethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C. Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

A compounds of formula (2) where Z is CH may be prepared according to Scheme 1:

Scheme 1

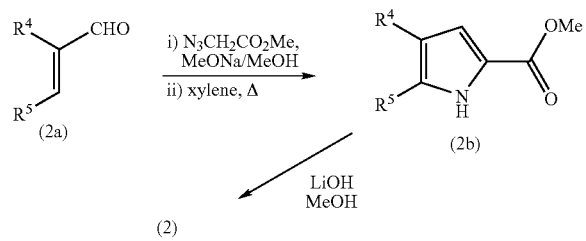

Compounds of formula (2a) are commercially available or they are known compounds or they are prepared by processes known in the art.

A compound of the formula (2) wherein X is nitrogen, can be prepared from a compound of the formula (4):

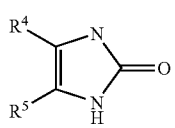

(4)

by firstly converting the oxo group to chlorine or bromine with a halogenating agent such as $POCl_3$ or $POBr_3$, in an inert organic solvent such as dichloromethane in a temperature range of ambient temperature to reflux (for example see *Nucleic Acid Chem.* 1991, 4, 24–6), then displacing the chlorine or bromine group with cyanide using a cyanide salt such as potassium cyanide, in an inert organic solvent such as toluene, benzene or xylene, optionally in the presence of a catalyst such as 18-crown-6 (for example see *J. Heterocycl. Chem* 2000, 37(1), 119–126) and finally hydrolysing the cyano group to a carboxy group, with for example, an aqueous acid such as aqueous hydrogen chloride (for example see *Chem. Pharm. Bull.* 1986, 34(9), 3635–43).

Alternatively, a compound of the formula (2) wherein X is nitrogen may be formed by reacting the compound of the formula (4) with $(Cl_3CCO)_2O$ and $Cl_3CCO_2H$ in the presence of magnesium chloride using $Cl_3CCO_2H$ as solvent, to form a compound of the formula (5):

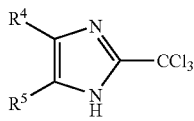
(5)

and then hydrolysing the compound of the formula (5), using, for example, aqueous sodium hydroxide, at a temperature range of ambient temperature to reflux (for example see *J Heterocycl. Chem.* 1980, 17(2), 381–2).

The compound of formula (4) may be prepared from a compound of formula (6) and (7) using conditions known for the Curtius rearrangement (*Tetrahedron* 1999, 55, 6167):

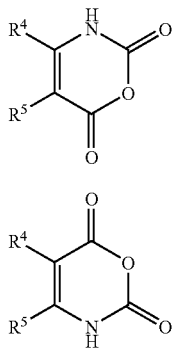
(6)

(7)

The compounds of the formula (8) and (9):

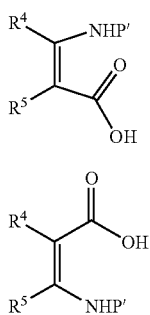
(8)

(9)

transform into compounds of the formula (6) and (7) respectively. This transformation either occurs spontaneously or may be induced with acid or base.

Compounds of the formula (8) and (9) may be prepared by introducing a carboxy group into a compound of the formula (10) or (11):

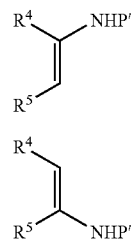
(10)

(11)

wherein P' is an amino protecting group such as butoxycarbonyl.

A carboxy group is introduced into the compound of the formula (10) or (11) by reacting an alkyl lithium reagent such as n-butyl lithium, in an inert organic solvent such as THF, at low temperature, for example in the range —10° C. to −78° C. and then forming the compound of the formula (8) or (9) as appropriate by either a) reacting the resulting compound with carbon dioxide; or b) by reacting with DMF in the temperature range of −10° C. to ambient temperature to form the corresponding aldehyde and oxidizing the aldehyde to carboxy with standard reagents to give the compound of the formula (8) or (9).

Compounds of the formula (10) and (11) may be prepared from a compound of the formula (12) and (13):

(12)

(13)

using conditions known for the Curtius reaction.

Compounds of the formula (12) and (13) may be prepared by oxidizing the corresponding aldehyde using standard oxidizing reagents such as potassium manganate or sodium periodate.

The aldehyde precursor of a compound of the formula (12) or (13) can be prepared using standard techniques known in the art. For example, many compounds of the formula (12) or (13) may be prepared by introducing the appropriate $R^6$ and $R^7$ into a compound of the formula (14) or (15) as appropriate:

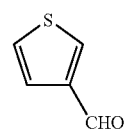
(14)

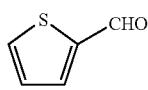
(15)

For example, when $R^6$ and $R^7$ are both chloro a compound of the formula (14) or (15) may be chlorinated with a chlorinating agent such as chlorine in the presence of aluminium chloride or iron (III) chloride, in an inert organic chlorinated solvent such as dichloromethane or 1,2-dichloroethane, followed by treatment with an aqueous base, such as, aqueous sodium hydroxide. The mono chlorinated compound can be formed in the same way.

Compounds of formula (2b) may also be prepared as illustrated in Scheme 2:

Scheme 2

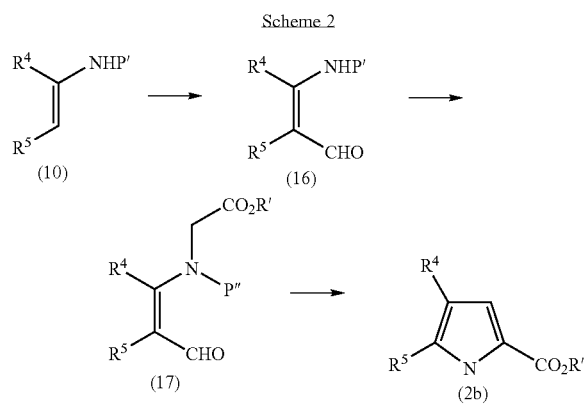

The conversion of compounds of formula (10) into compounds of formula (16) may be carried out by directed ortho lithiation reactions (J. Org. Chem, 2001, volume 66, 3662–3670), for example with n-butyl lithium and (CHO)N(alkyl)$_2$. The protecting group P' in compounds of formula (10) must be suitable directing group for this reaction and may be for example —CO$_2$tBu. Reaction of compounds of formula (16) with LCH$_2$CO$_2$R where L is a leaving group, and replacement of the protecting group P' with an alternative P'" (for example —COalkyl) according to standard processes, gives a compound of formula (17). This may be cyclised using a base, for example potassium carbonate or sodium methoxide.

Compounds of formula (3) where Y is OR$^3$ are commercially available or they are known compounds or they are prepared by processes known in the art. When Y is NR$^2$R$^3$, the amines of formula (3) may be prepared according to Scheme 3:

Scheme 3

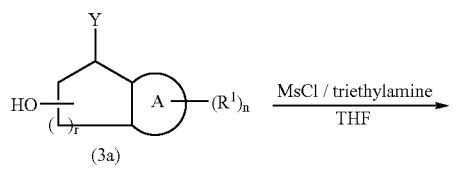

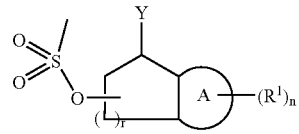

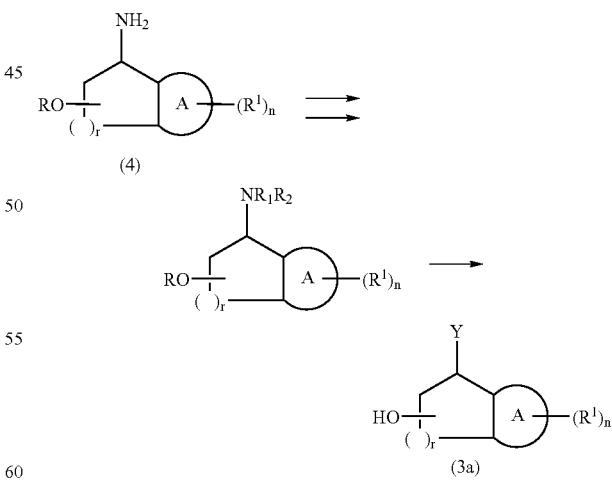

Compounds of formula (3a) are commercially available or they are known compounds or they are prepared by processes known in the art. For example, starting from primary amines of formula (4), in which R is H or a suitable protecting group, one or both of $R^1$ and/or $R^2$ may be introduced by acylation, (for example reacting with acetoxyacetic acid and 1-(3-dimethylaminopropyl)-3-ethyl-carbodiimide hydrochloride-EDAC), alkylation, reductive alkylation, sulphonation or related processes, followed by O-deprotection when appropriate. Alternatively, one or both of $R^1$ and/or $R^2$ may be obtained by modification of functionality in groups previously thus introduced, by reduction, oxidation, hydrolysis (for example the conversion of an acetoxy group to a hydroxy group), nucleophilic displacement, amidation, or a related process, or a combination of these processes, followed by O-deprotection when appropriate. It will be appreciated that such modifications may include modifications which convert one compound of the formula (1) into another compound of the formula (1).

Amines of formula (3) may alternatively be obtained by applying the processes described for the preparation of compounds of formula (3a) to compounds of formula (20) in which W is NH$_2$ or a nitrogen atom with one or two suitable protecting groups.

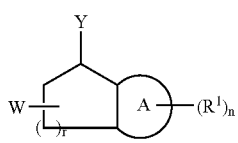 (20)

Compounds of the formula (3) where r=1 and wherein A is heteroarylene can be prepared from suitably functionalised cycloalkyl fused heterocycles. For example, when A is pyridine,

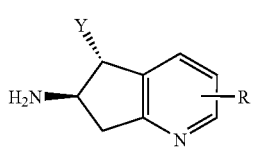 (3b)

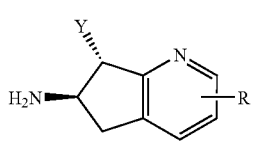 (3c)

compounds of formula (3b) and (3c) may be prepared from the corresponding pyrindinone regioisomer according to Scheme 4:—

Step 1 is performed on a compound known in the literature (*Jpn. Kokai Tokkyo Koho,* 1995, 14. JP 07070136). Steps 2, 3, 4, 5, 6, 7 and 8 are performed using standard techniques known in the art.

It will be appreciated that the bromopyrindinone isomers (21a, 21b and 21c) could

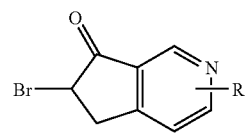 (21a)

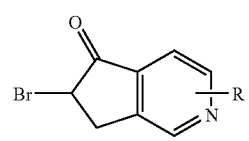 (21b)

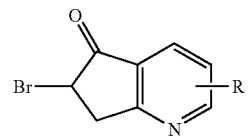 (21c)

be converted to the corresponding heterocylic version of (3) by the means described in Scheme 4. The bromopyridinones can be prepared from the corresponding pyrindinone by standard techniques known in the art. The pyrindinones (22a, 22b, 22c) are known in the literature or they are prepared by processes known in the art.

Scheme 4

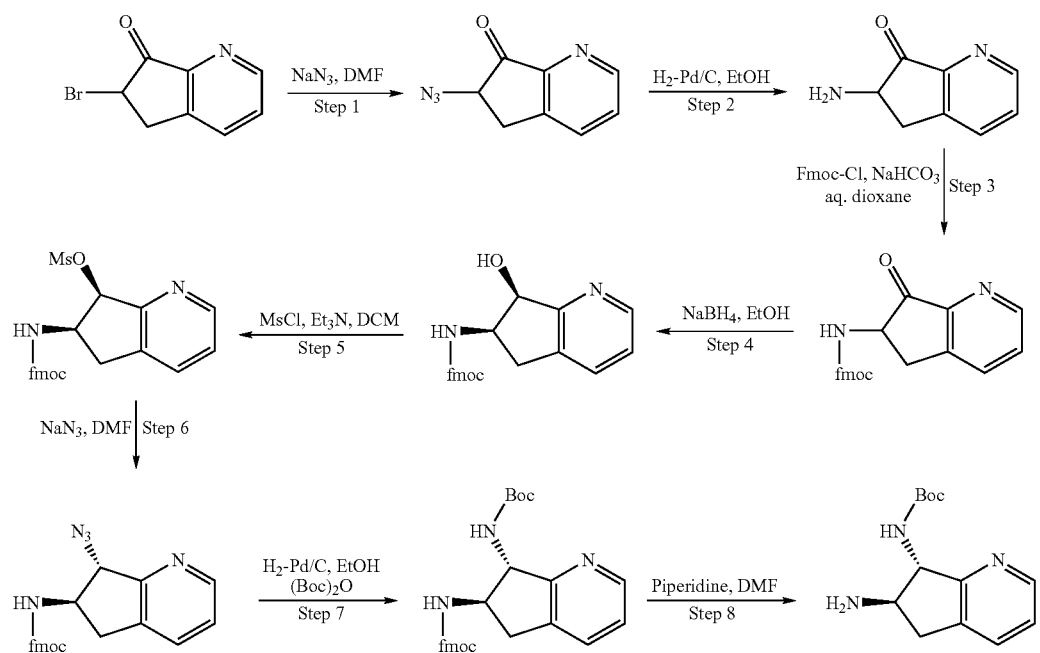

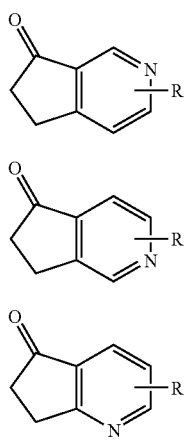

(22a)

(22b)

(22c)

The process described above and shown in Scheme 4 may also be applied to other six membered heterocycles containing more than one nitrogen.

It will be appreciated that, in a similar manner, compounds of the formula (3) wherein A is heteroarylene containing a bridgehead nitrogen can be prepared from the appropriate suitably functionalised cycloalkyl fused heterocycles.

It will be appreciated that the processes described above for formation and modification of Y as $NR^1R^2$ may be applied similarly whether to make the compound of formula (3) before coupling to the acid of formula (2) or whether to the product of such a coupling.

It will be appreciated that certain of the various ring substituents in the compounds of the present invention, for example $R^1$ may be introduced by standard aromatic substitution reactions or generated by conventional functional group modifications either prior to or immediately following the processes mentioned above, and as such are included in the process aspect of the invention. Such reactions may convert one compound of the formula (1) into another compound of the formula (1). Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain intermediates in the preparation of a compound of the formula (1) are novel and form another aspect of the invention.

As stated hereinbefore the compounds defined in the present invention possesses glycogen phosphorylase inhibitory activity. This property may be assessed, for example, using the procedure set out below.

Assay

The activity of the compounds is determined by measuring the inhibitory effect of the compounds in the direction of glycogen synthesis, the conversion of glucose-1-phosphate into glycogen with the release of inorganic phosphate, as described in EP 0 846 464 A2. The reactions were in 96 well microplate format in a volume of 100 µl. The change in optical density due to inorganic phosphate formation was measured at 620 nM in a Labsystems IEMS Reader MF by the general method of (Nordlie R. C and Arion W. J, Methods of Enzymology, 1966, 619–625). The reaction is in 50 mM HEPES (N-(2-Hydroxyethyl)piperazine-N'-(2-ethanesulfonic acid); 4-(2-Hydroxyethyl)piperazine-1-ethanesulfonic acid), 2.5 mM $MgCl_2$, 2.25 mM ethylene glycol-bis(b-aminoethyl ether) N,N,N',N'-tetraacetic acid, 100 mM KCl, 2 mM D-(+)-glucose pH7.2, containing 0.5 mM dithiothreitol, the assay buffer solution, with 0.1 mg type III glycogen, 0.15 ug glycogen phosphorylase a (GPa) from rabbit muscle and 0.5 mM glucose-1-phosphate. GPa is pre-incubated in the assay buffer solution with the type III glycogen at 2.5 mg $ml^{-1}$ for 30 minutes. 40 µl of the enzyme solution is added to 25 µl assay buffer solution and the reaction started with the addition of 25 µl 2 mM glucose-1-phosphate. Compounds to be tested are prepared in 10 µl 10% DMSO in assay buffer solution, with final concentration of 1% DMSO in the assay. The non-inhibited activity of GPa is measured in the presence of 10 µl 10% DMSO in assay buffer solution and maximum inhibition measured in the presence of 30 µM CP320626 (Hoover et al (1998) J Med Chem 41, 2934–8; Martin et al (1998) PNAS 95, 1776–81). The reaction is stopped after 30 min with the addition of 50 µl acidic ammonium molybdate solution, 12 ug $ml^{-1}$ in 3.48% $H_2SO_4$ with 1% sodium lauryl sulphate and 10 ug $ml^{-1}$ ascorbic acid. After 30 minutes at room temperature the absorbency at 620 nm is measured.

The assay is performed at a test concentration of inhibitor of 10 µM or 100 µM. Compounds demonstrating significant inhibition at one or both of these concentrations may be further evaluated using a range of test concentrations of inhibitor to determine an $IC_{50}$, a concentration predicted to inhibit the enzyme reaction by 50%.

Activity is calculated as follows:—

% inhibition=(1−(compound OD620−fully inhibited OD620)/(non-inhibited rate OD620−fully inhibited OD620))*100.

OD620=optical density at 620 nM.

Typical $IC_{50}$ values for compounds of the invention when tested in the above assay are in the range 100 µM to 1 nM.

The activity of the compounds is alternatively determined by measuring the inhibitory effect of the compounds on glycogen degradation, the production of glucose-1-phosphate from glycogen is monitored by the multienzyme coupled assay, as described in EP 0 846 464 A2, general method of Pesce et al (Pesce, M A, Bodourian, S H, Harris, R C, and Nicholson, J F (1977) Clinical Chemistry 23, 1171–1717). The reactions were in 384 well microplate format in a volume of 50 µl. The change in fluorescence due to the conversion of the co-factor NAD to NADH is measured at 340 nM excitation, 465 nm emission in a Tecan Ultra Multifunctional Microplate Reader. The reaction is in 50 mM HEPES, 3.5 mM $KH_2PO_4$, 2.5 mM $MgCl_2$, 2.5 mM ethylene glycol-bis(b-aminoethyl ether) N,N,N',N'-tetraacetic acid, 100 mM KCl, 8 mM D-(+)-glucose pH7.2, containing 0.5 mM dithiothreitol, the assay buffer solution. Human recombinant liver glycogen phosphorylase a (hrl GPa) 20 nM is pre-incubated in assay buffer solution with 6.25 mM NAD, 1.25 mg type III glycogen at 1.25 mg $ml^{-1}$ the reagent buffer, for 30 minutes. The coupling enzymes, phosphoglucomutase and glucose-6-phosphate dehydrogenase (Sigma) are prepared in reagent buffer, final concentration 0.25 Units per well. 20 µl of the hrl GPa solution is added to 10 µl compound solution and the reaction started with the addition of 20 ul coupling enzyme solution. Compounds to be tested are prepared in 10 µl 5% DMSO in assay buffer solution, with final concentration of 1% DMSO in the assay. The non-inhibited activity of GPa is measured in the presence of 10 µl 5% DMSO in assay buffer solution and maximum inhibition measured in the presence of 5 mgs $ml^{-1}$ N-ethylmaleimide. After 6 hours at 30° C. Relative Fluoresence Units (RFUs) are measured at 340 nM excitation, 465 nm emission.

The assay is performed at a test concentration of inhibitor of 10 µM or 100 µM. Compounds demonstrating significant inhibition at one or both of these concentrations may be further evaluated using a range of test concentrations of inhibitor to determine an $IC_{50}$, a concentration predicted to inhibit the enzyme reaction by 50%.

Activity is calculated as follows:—

% inhibition=(1−(compound RFUs−fully inhibited RFUs)/(non-inhibited rate RFUs−fully inhibited RFUs))*100.

Typical $IC_{50}$ values for compounds of the invention when tested in the above assay are in the range 100 µM to 1 nM. For example, Example 10 was found to have an $IC_{50}$ of 4.5 µm.

The inhibitory activity of compounds was further tested in rat primary hepatocytes.

Rat hepatocytes were isolated by the collagenase perfusion technique, general method of Seglen (P. O. Seglen, Methods Cell Biology (1976) 13 29–83). Cells were cultured on Nunclon six well culture plates in DMEM (Dulbeco's Modified Eagle's Medium) with high level of glucose containing 10% foetal calf serum, NEAA (non essential amino acids), Glutamine, penicillin/streptomycin ((100 units/100 ug)/ml) for 4 to 6 hours. The hepatocytes were then cultured in the DMEM solution without foetal calf serum and with 10 nM insulin and 1 nM dexamethasone. Experiments were initiated after 18–20 hours culture by washing the cells and adding Krebs-Henseleit bicarbonate buffer containing 2.5 mM $CaCl_2$ and 1% gelatin. The test compound was added and 5 minutes later the cells were challenged with 25 nM glucagon. The Krebs-Henseleit solution was removed after 60 min incubation at 37° C., 95% $O_2$/5% $CO_2$ and the glucose concentration of the Krebs-Henseleit solution measured.

According to a further aspect of the invention there is provided a pharmaceutical composition which comprises a compound of the formula (1), or a pharmaceutically acceptable salt or in vivo hydrolysable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compound of formula (1) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The inhibition of glycogen phosphorylase activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:
1) Insulin and insulin analogues;
2) Insulin secretagogues including sulphonylureas (for example glibenclamide, glipizide) and prandial glucose regulators (for example repaglinide, nateglinide);
3) Insulin sensitising agents including PPARg agonists (for example pioglitazone and rosiglitazone);
4) Agents that suppress hepatic glucose output (for example metformin).
5) Agents designed to reduce the absorption of glucose from the intestine (for example acarbose);
6) Agents designed to treat the complications of prolonged hyperglycaemia;
7) Anti-obesity agents (for example sibutramine and orlistat);
8) Anti-dyslipidaemia agents such as, HMG-CoA reductase inhibitors (statins, eg pravastatin); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
9) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
11) Anti-inflammatory agents, such as non-steroidal anti-inflammatory drugs (eg. aspirin) and steroidal anti-inflammatory agents (eg. cortisone).

According to a further aspect of the present invention there is provided a compound of the formula (1), or a pharmaceutically acceptable salt or in vivo hydrolysable ester thereof, as defined hereinbefore, for use in a method of treatment of a warm-blooded animal such as man by therapy.

According to an additional aspect of the invention there is provided a compound of the formula (1), or a pharmaceutically acceptable salt or in vivo hydrolysable ester thereof, as defined hereinbefore, for use as a medicament.

According to an additional aspect of the invention there is provided a compound of the formula (1), or a pharmaceutically acceptable salt or in vivo hydrolysable ester thereof, as defined hereinbefore, for use as a medicament in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes in a warm-blooded animal such as man.

According to a further feature of this aspect of the invention there is provided a method of producing a glycogen phosphorylase inhibitory effect in a warm-blooded animal, such as man, in need of such treatment which comprises administering to said animal an effective amount of a compound of formula (1).

According to this further feature of this aspect of the invention there is provided a method of treating type 2 diabetes, insulin resistance, syndrome X, hyperinsulinaemia, hyperglucagonaemia, cardiac ischaemia or obesity in a warm-blooded animal, such as man, in need of such treatment which comprises administering to said animal an effective amount of a compound of formula (1).

According to this further feature of this aspect of the invention there is provided a method of treating type 2 diabetes in a warm-blooded animal, such as man, in need of such treatment which comprises administering to said animal an effective amount of a compound of formula (1).

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

In addition to their use in therapeutic medicine, the compounds of formula (1) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non-limiting examples in which, unless stated otherwise:
(i) temperatures are given in degrees Celsius (° C.); operations were carried out at room or ambient temperature, that is, at a temperature in the range of 18–25° C. and under an atmosphere of an inert gas such as argon;
(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;
(iii) chromatography means flash chromatography on silica gel; thin layer chromatography (TLC) was carried out on silica gel plates; where a Bond Elut column is referred to, this means a column containing 10 g or 20 g or 50 g of silica of 40 micron particle size, the silica being contained in a 60 ml disposable syringe and supported by a porous disc, obtained from Varian, Harbor City, Calif., USA under the name "Mega Bond Elut SI"; "Mega Bond Elut" is a trademark; where a Biotage cartridge is referred to this means a cartridge containing KP-SIL™ silica, 60μ, particle size 32–63 mM, supplied by Biotage, a division of Dyax Corp., 1500 Avon Street Extended, Charlottesville, Va. 22902, USA;

(iv) in general, the course of reactions was followed by TLC and reaction times are given for illustration only;
(v) yields are given for illustration only and are not necessarily those which can be obtained by diligent process development; preparations were repeated if more material was required;
(vi) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$\delta_6$) as solvent unless otherwise indicated, other solvents (where indicated in the text) include deuterated chloroform $CDCl_3$;
(vii) chemical symbols have their usual meanings; SI units and symbols are used;
(viii) reduced pressures are given as absolute pressures in Pascals (Pa); elevated pressures are given as gauge pressures in bars;
(ix) solvent ratios are given in volume:volume (v/v) terms;
(x) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported and unless otherwise stated the value quoted is (M−H)$^-$;
(xi) The following abbreviations are used:
SM starting material;
EtOAc ethyl acetate;
MeOH methanol;
EtOH ethanol;
DCM dichloromethane;
HOBT 1-hydroxybenzotriazole;
DIPEA di-isopropylethylamine;
EDCI 1-ethyl-3-(3-dimethylaminopropyl)carbodiimide hydrochloride;
$Et_2O$ diethyl ether;
THF tetrahydrofuran;
DMF N,N-dimethylformamide;
HATU O-(7-Azabenzotriazol-1-yl)-N,N,N',N'-tetramethyluroniumhexafluorophosphate
EDAC 1-(3-dimethylaminopropyl)-3-ethyl-carbodiimide hydrochloride
TFA Trifluoroacetic acid
DMTMM 4-(4,6-Dimethoxy-1,3,5-triazin-2-yl)-4-methylmorpholinium chloride
DMA N,N-dimethylacetamide Example 1

2,3-Dichloro-N-[(1R,2R)-1-(formylamino)-2,3-dihydro-1H-inden-2-yl]4H-thieno[3,2-b]pyrrole-5-carboxamide

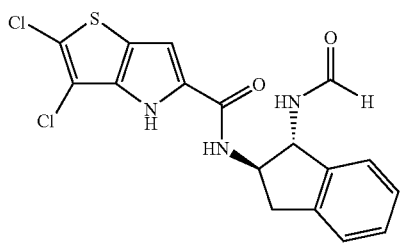

N-[(1R,2R)-1-Amino-2,3-dihydro-1H-inden-2-yl]-2,3-dichloro-4H-thieno[3,2-b]pyrrole-5-carboxamide trifluoroacetic acid salt (Method 8, 240 mg, 0.5 mmol), formic acid (50 μL, 1.4 mmol), DIPEA (174 μL, 1.0 mmol) and HOBT (67 mg, 0.5 mmol) were dissolved in DCM (5 ml), stirred for 5 mins, EDCI (120 mg, 0.625 mmol) added and the reaction stirred for 1 hr. Formic acid (50 μL, 1.4 mmol) and EDCI (240 mg, 1.25 mmol) were added, the reaction stirred for 2 hours and the volatiles removed by evaporation under reduced pressure. The residue was dissolved in EtOAc (20 mL), washed with water (2×10 mL), brine (10 mL), dried ($MgSO_4$) and the volatiles removed by evaporation under reduced pressure. The residue was purified by column chromatography (2:1 EtOAc:Hexane) to afford the title compound (175 mg, 89%) as a white foam.

$^1$H NMR 2.86 (dd, 1H), 3.23 (dd, 1H), 4.6 (m, 1H), 5.53 (m, 1H), 7.12 (m, 2H), 7.25 (m, 1H), 8.2 (s, 1H), 8.55 (d, 1H), 8.63 (d, 1H), 12.36 (s, 1H); MS m/z 394.

Example 2

2,3-Dichloro-N-((1R,2R)-1-{[(methyloxy)acetyl]amino}-2,3-dihydro-1H-inden-2-yl)-4H-thieno[3,2-b]pyrrole-5-carboxamide

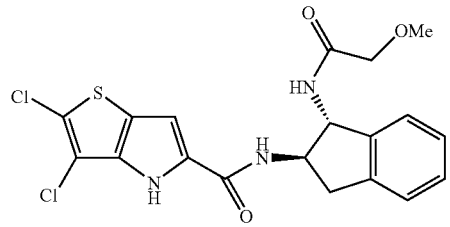

DIPEA (180 μL, 1.05 mmol), HOBT (68 mg, 0.5 mmol), methoxyacetic acid (0.5 mmol, 38 μL) and EDAC (120 mg, 0.63 mmol) were added to a suspension of N-[(1R,2R)-1-amino-2,3-dihydro-1H-inden-2-yl]-2,3-dichloro-4H-thieno[3,2-b]pyrrole-5-carboxamide (Method 8, 240 mg, 0.5 mmol) in anhydrous DCM (7 mL). The reaction was stirred at ambient temperature for approximately 16 h. The volatiles were removed by evaporation under reduced pressure, the residue dissolved in EtOAc (10 mL), washed with water (2×10 mL), brine (10 mL) and dried ($MgSO_4$). The volatiles were removed by evaporation under reduced pressure and the residue was purified by flash column chromatography on $SiO_2$ (1:1 EtOAc:isohexane); the solvent removed by evaporation under reduced presssure and dried to give the title compound (44 mg, 20%) as a white solid.

$^1$H NMR 2.88 (dd, 1H), 3.26 (dd, 1H), 3.87 (dd, 2H), 4.73 (m 1H), 5.51 (t, 1H), 7.17 (m, 5H), 8.26 (d, 1H), 8.59 (d, 1H), 12.36 (s, 1H); MS m/z 439.

The following examples were made by the process similar to Example 2 using N-[(1R,2R)-1-amino-2,3-dihydro-1H- inden-2-yl]-2,3-dichloro-4H-thieno[3,2-b]pyrrole-5-carboxamide (Method 8) and the appropriate commercially available carboxylic acid:

The following examples were made by the process similar to Example 2 using N-[(1R,2R)-1-amino-2,3-dihydro-1H-inden-2-yl]-2,3-dichloro-4H-thieno[3,2-b]pyrrole-5-carboxamide (Method 8) and the appropriate commercially available carboxylic acid:

Example 3

N-((1S,2S)-1-{[(3R)-3-(tert-Butoxycarbonylamino)-3-carbamoylpropanoyl]amino}-2,3-dihydro-1H-inden-2-yl)-2,3-dichloro-4H-thieno[3,2-b]pyrrole-5-carboxamide

Example 4

2,3-Dichloro-N-[(1R,2R)-1-({[(4R)-2,2-dimethyl-5-oxo-1,3-dioxolan-4-yl]acetyl}amino)-2,3-dihydro-1H-inden-2-yl]-4H-thieno[3,2-b]pyrrole-5-carboxamide

Example 5

2,3-Dichloro-N-{(1R,2R)-1-[(3-methoxypropanoyl)amino]-2,3-dihydro-1H-inden-2-yl}-4H-thieno[3,2-b]pyrrole-5-carboxamide

Example 6

N-{(1R,2R)-1-[(2-Acetoxyacetyl)amino]-2,3-dihydro-1H-inden-2-yl}-2,3-dichloro-4H-thieno[3,2-b]pyrrole-5-carboxamide

Example 7

N-{(1R,2R)-1-[(2-Carbamoylacetyl)amino]-2,3-dihydro-1H-inden-2-yl}-2,3-dichloro-4H-thieno[3,2-b]pyrrol-5-carboxamide

Example 55

2,3-Dichloro-N-{(1R,2R)-1-[(trifluoroacetyl)amino]-2,3-dihydro-1H-inden-2-yl}-4H-thieno[3,2-b]pyrrole-5-carboxamide

| Ex | R | NMR | M/z |
|---|---|---|---|
| 3 | ,,,NHBoc / NH₂ / O (structure) | (DMSO-d$_6$) 1.37 (s, 9H), 2.89 (dd, 1H), 3.23 (dd, 1H), 4.25 (m, 1H), 4.55 (m, 1H), 5.46 (t, 1H), 6.68 (d, 1H), 6.97 (s, 1H), 7.17 (m, 6H), 8.31 (d, 1H), | 578 |
| 4 | Me, Me dioxolanone (structure) | | 523 |
| 5 | CH$_2$CH$_2$OMe | (DMSO-d$_6$) 2.33 (m, 2H), 2.84 (dd, 1H), 3.28 (s, 3H) 3.24 (m, 1H), 3.56 (m, 2H), 4.57 (m, 1H), 5.47 (t, 1H), 7.17 (m, 5H), 8.35 (d, 1H), 8.59 (d, 1H), 12.36 (s, 1H) | 452 |
| 6 | CH$_2$OAc | — | 466 |
| 7 | CH$_2$C(O)NH$_2$ | (DMSO-d$_6$) 2.86 (dd, 1H), 3.07 (m, 2H), 3.25 (m, 1H), 4.57 (m, 1H), 5.47 (m, 1H), 6.98 (s, 1H), 7.11 (s, 1H), 7.22 (m, 4H), 7.37 (s, 1H), 8.51 (d, 1H), 8.62 (d, 1H), 12.35 (s, 1H); | 451 |
| 55 | CF$_3$ | — | 462 |

The following examples were made by the process of Example 2 using N-[(1S,2S)-1-amino-2,3-dihydro-1H-inden-2-yl]-2,3-dichloro-4H-thieno[3,2-b]pyrrole-5-carboxamide (Method 9) and the appropriate commercially available carboxylic acid.

Example 8

2,3-Dichloro-N-{(1S,2S)-1-[(furan-2-ylcarbonyl)amino]-2,3-dihydro-1H-inden-2-yl}-4H-thieno[3,2-b]pyrrole-5-carboxamide

Example 9

2,3-Dichloro-N-{(1S,2S)-1-[(furan-3-ylcarbonyl)amino]-2,3-dihydro-1H-inden-2-yl}-4H-thieno[3,2-b]pyrrole-5-carboxamide

Example 10

2,3-Dichloro-N-{(1S,2S)-1-[(3-thienylcarbonyl)amino]-2,3-dihydro-1H-inden-2-yl}-4H-thieno[3,2-b]pyrrole-5-carboxamide

Example 11

2,3-Dichloro-N-((1S,2S)-1-{[(5-nitrofuran-2-yl)carbonyl]amino}-2,3-dihydro-1H-inden-2-yl)-4H-thieno[3,2-b]pyrrole-5-carboxamide

Example 12

2,3-Dichloro-N-{(1S,2S)-1-[(pyridin-3-ylcarbonyl)amino]-2,3-dihydro-1H-inden-2-yl}-4H-thieno[3,2-b]pyrrole-5-carboxamide

Example 13

N-[(1S,2S)-1-(Acryloylamino)-2,3-dihydro-1H-inden-2-yl]-2,3-dichloro-4H-thieno[3,2-b]pyrrole-5-carboxamide

Example 14

2,3-Dichloro-N-((1S,2S)-1-{[(3-hydroxyphenyl)carbonyl]amino}-2,3-dihydro-1H-inden-2-yl)-4H-thieno[3,2-b]pyrrole-5-carboxamide

Example 15

N-[(1S,2S)-1-(Acetylamino)-2,3-dihydro-1H-inden-2-yl]-2,3-dichloro-4H-thieno[3,2-b]pyrrole-5-carboxamide

Example 16

N-[(1S,2S)-1-[(2-Carboxyacetyl)amino]-2,3-dihydro-1H-inden-2-yl]-2,3-dichloro-4H-thieno[3,2-b]pyrrole-5-carboxamide

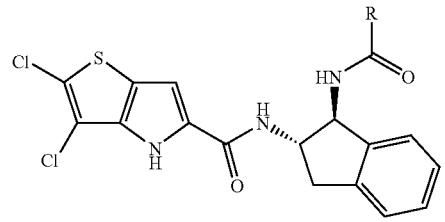

| Ex | R | NMR | M/z |
|---|---|---|---|
| 8 | 2-furyl | — | 458 (M − H)⁻ |
| 9 | 3-furyl | — | 458 (M − H)⁻ |
| 10 | 2-thienyl | — | 476 (M − H)⁻ |
| 11 | 5-nitro-2-furyl | — | 503 (M − H)⁻ |

| Ex | R | NMR | M/z |
|----|---|-----|-----|
| 12 | 3-pyridyl | — | 471 |
| 13 | vinyl | — | 417 (M − H)⁻ |
| 14 | 3-hydroxyphenyl | — | 484 |
| 15 | CH₃ | 1.87 (s, 3H), 2.83 (m, 1H), 3.23 (m, 1H), 4.55 (m, 1H), 5.45 (m, 1H), 7.1 (s, 1H), 7.13 (m, 1H), 7.22 (m, 3H), 8.34 (d, 1H), 8.59 (d, 1H), 12.36 (s, 1H) | — |
| 16 | CH₂CO₂H | — | 452 |

Example 17

2,3-Dichloro-N-((1S,2S)-1-{[(dimethylamino)carbonyl]amino}-2,3-dihydro-1H-inden-2-yl)-4H-thieno[3,2-b]pyrrole-5-carboxamide

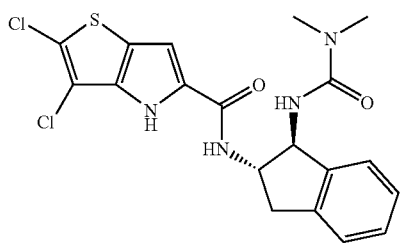

To a solution of N-[(1S,2S)-1-amino-2,3-dihydro-1H-inden-2-yl]-2,3-dichloro-4H-thieno[3,2-b]pyrrole-5-carboxamide (Method 9, 240 mg, 0.5 mmol) and Et₃N (101 mg, 1.0 mmol) in DCM (4 mL) was added a solution of dimethylcarbamoyl chloride (54 mg, 0.5 mmol) in DCM (1 mL). The reaction was stirred at ambient temperature for 2 hours, washed with saturated NaHCO₃ (1 mL), water (1 mL), brine (1 mL) and dried (MgSO₄). The volatiles were removed by evaporation under reduced pressure to give the title compound (50 mg, 23%) as a foam.

¹H NMR 2.81 (s, 6H), 2.83 (m, 1H), 3.25 (m, 1H), 4.61 (m, 1H), 5.33 (m, 1H), 7.16 (m, 5H), 8.6 (d, 1H), 12.37 (s, 1H); MS m/z 437.

Example 18

2,3-Dichloro-N-((1S,2S)-1-{[(4-methylpiperazin-1-yl)carbonyl]amino}-2,3-dihydro-1H-inden-2-yl)-4H-thieno[3,2-b]pyrrole-5-carboxamide

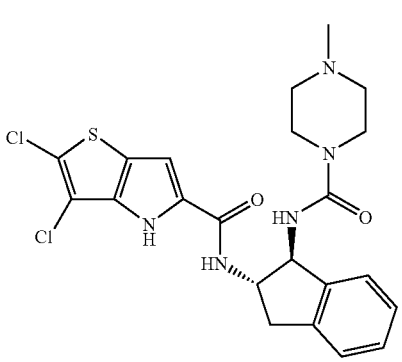

To a solution of N-[(1S,2S)-1-amino-2,3-dihydro-1H-inden-2-yl]-2,3-dichloro-4H-thieno[3,2-b]pyrrole-5-carboxamide (Method 9, 240 mg, 0.5 mmol) and Et₃N (101 mg, 1.0 mmol) in DCM (4 mL) was added a solution of 4-methyl-1-piperazine carbonyl chloride (100 mg, 0.5 mmol) in DCM (1 mL). The reaction was stirred at ambient temperature for 2 hours, washed with saturated NaHCO$_3$ (1 mL), water (1 mL), brine (1 mL) and dried (MgSO$_4$). The volatiles were removed by evaporation under reduced pressure to give the title compound (110 mg, 45%) as a foam. MS m/z (M−H)$^-$ 491.

The following examples were made by the method below using N-[(1S,2S)-1-amino-2,3-dihydro-1H-inden-2-yl]-2,3-dichloro-4H-thieno[3,2-b]pyrrole-5-carboxamide trifluoroacetic acid salt (Method 9) and the appropriate commercially available isocyanate:

N-[(1S,2S)-1-amino-2,3-dihydro-1H-inden-2-yl]-2,3-dichloro-4H-thieno[3,2-b]pyrrole-5-carboxamide trifluoroacetic acid salt (0.5 mmol) and Et$_3$N (1.0 mmol) were dissolved in dry THF (5 mL), the appropriate isocyanate (1.0 mmol) was added and the reaction stirred at ambient temperature for 20 hours. EtOAc (15 mL) was added and the mixture washed with water (2×5 mL) brine (5 mL), dried (MgSO$_4$) and the volatiles removed by evaporation under reduced pressure to give the title compound as a foam.

Example 19

2,3-Dichloro-N-((1S,2S)-1-{[(ethylamino)carbonyl]amino}-2,3-dihydro-1H-inden-2-yl)-4H-thieno[3,2-b]pyrrole-5-carboxamide

Example 20

2,3-Dichloro-N-((1S,2S)-1-{[(prop-2-en-1-ylamino)carbonyl]amino}-2,3-dihydro-1H-inden-2-yl)-4H-thieno[3,2-b]pyrrole-5-carboxamide

Example 21

2,3-Dichloro-N-[(1S,2S)-1-({[(3,5-dinitrophenyl)amino]carbonyl}amino)-2,3-dihydro-1H-inden-2-yl]-4H-thieno[3,2-b]pyrrole-5-carboxamide

| Ex | R | M/z |
|---|---|---|
| 19 | CH$_2$CH$_3$ | 437/439 |
| 20 | 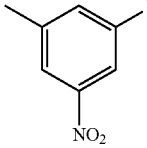 | 449/451 |
| 21 | 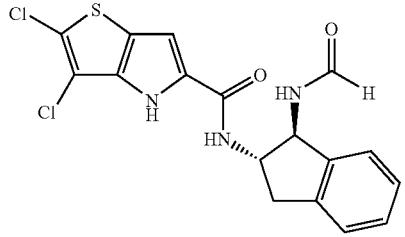 | 364/366 (—C$_7$H$_3$N$_3$O$_5$) |

Example 22

2,3-Dichloro-N-[(1S,2S)-1-(formylamino)-2,3-dihydro-1H-inden-2-yl]-4H-thieno[3,2-b]pyrrole-5-carboxamide

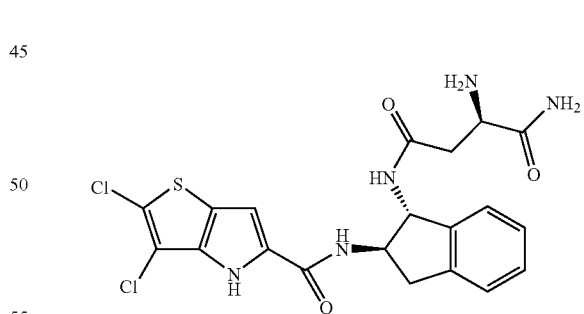

N-[(1S,2S)-1-Amino-2,3-dihydro-1H-inden-2-yl]-2,3-dichloro-4H-thieno[3,2-b]pyrrole-5-carboxamide trifluoroacetic acid salt (Method 9, 240 mg, 05 mmol), formic acid (50 μL, 1.4 mmol), DIPEA (174 μL, 1.0 mmol) and HOBT (67 mg, 0.5 mmol) were dissolved in DCM (5 ml), stirred for 5 mins, EDCI (120 mg, 0.625 mmol) added and the reaction stirred for 1 hr. Formic acid (50 μL, 1.4 mmol) and EDCI (240 mg, 1.25 mmol) were added, the reaction stirred for 2 hours and the volatiles removed by evaporation under reduced pressure. The residue was dissolved in EtOAc (20 mL), washed with water (2×10 mL), brine (10 mL), dried (MgSO$_4$) and the volatiles removed by evaporation under reduced pressure. The residue was purified by column chromatography (2:1 EtOAc:Hexane) to afford the title compound (180 mg, 97%) as a white foam.

$^1$H NMR 2.86 (dd, 1H), 3.23 (dd, 1H), 4.6 (m, 1H), 5.53 (m, 1H), 7.12 (m, 2H), 7.25 (m, 1H), 8.2 (s, 1H), 8.55 (d, 1H), 8.63 (d, 1H), 12.36 (s, 1H); MS m/z 394.

Example 23

N-{(1R,2R)-1-[((3R)-3-Amino-3-carbamoylpropanoyl)amino]-2,3-dihydro-1H-inden-2-yl}-2,3-dichloro-4H-thieno[3,2-b]pyrrole-5-carboxamide N-((1S,2S)-1-{[(3R)-3-(tert-Butoxycarbonylamino)-3-carbamoylpropanoyl]amino}-2,3-dihydro-1H-inden-2-yl)-2,3-dichloro-4H-thieno[3,2-b]pyrrole-5-carboxamide (Example 3; 290 mg, 0.5 mmol) was dissolved in TFA (3 mL) and the reaction stirred at ambient temperature for 1 hour. The volatiles were evaporated under reduced pressure and the crude material was azeotroped with chloroform (3×5 mL) to afford a gum. The gum was triturated with ether (5 mL), the solid collected by filtration, washed with ether (2×5 mL) and dried to give the trifluoroacetate salt of the title compound (270 mg, 91%) as a yellow solid.

¹H NMR 1.24 (m, 1H), 2.72 (m, 1H), 2.90 (dd, 1H), 3.26 (dd, 1H), 4.04 (m, 1H), 4.61 (m, 1H), 5.50 (t, 1H), 7.12 (s, 1H), 7.24 (m, 4H), 7.55 (s, 1H), 7.74 (s, 1H), 8.06 (br, 3H), 8.66 (d, 1H), 8.72 (d, 1H), 12.36 (s, 1H); MS m/z 502 (M+Na)$^+$.

Example 24

N-{(1R,2R)-1-[((3R)-3-Carboxy-3-hydroxypropanoyl)amino[-2,3-1H-inden-2-yl}-2,3-dichloro-4H-thieno[3,2-b]pyrrole-5-carboxamide

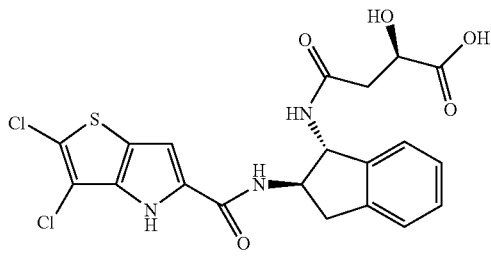

2,3-Dichloro-N-[(1R,2R)-1-({[(4R)-2,2-dimethyl-5-oxo-1,3-dioxolan-4-yl]acetyl}amino)-2,3-dihydro-1H-inden-2-yl]4H-thieno[3,2-b]pyrrole-5-carboxamide (Example 4; 200 mg, 0.4 mmole) was dissolved in THF (2 mL) and water (2 mL) and NaOH (100 mg) were added and the suspension stirred at ambient temperature for 48 hours. 2N HCl was added until pH 1 and the aqueous phase was extracted with EtOAc (3×5 mL). The combined organic phases were washed with water (10 mL), brine (10 mL) and dried (MgSO$_4$). The solvent was evaporated under reduced pressure and the reisdue was triturated with Et$_2$O, filtered and dried to give the title compound (133 mg, 69%) as a brown solid.

¹H NMR 2.45 (obs m, 2H), 2.87 (dd, 1H), 3.26 (obs dd, 1H), 4.39 (m, 1H), 4.57 (m, 1H), 5.52 (t, 1H), 7.18 (m, 5H), 8.43 (d, 1H), 6.63 (d, 1H), 12.39 (s, 1H); MS m/z 483.

Example 25

2,3-Dichloro-N-{(1R,2R)-1-[(hydroxyacetyl)amino]-2,3-dihydro-1H-inden-2-yl}-4H-thieno[3,2-b]pyrrole-5-carboxamide

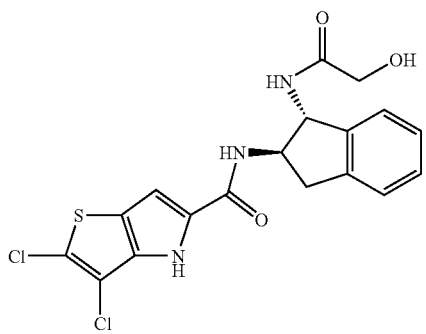

N-{(1R,2R)-1-[(2-Acetoxyacetyl)amino]-2,3-dihydro-1H-inden-2-yl}-2,3-dichloro-4H-thieno[3,2-b]pyrrole-5-carboxamide (Example 6; 632 mg, 1.36 mmol) was dissolved in THF (10 mL), MeOH (10 mL) and K$_2$CO$_3$ (100 mg) were then added and the suspension stirred at ambient temperature for 16 hours. Water (50 mL) was added and the aqueous phase was extracted with EtOAc (3×30 mL). The combined organic phases were washed with water (2×50 mL), brine (50 mL) and dried (MgSO$_4$). The solvent was removed by evaporation under reduced pressure, the crude product was triturated (EtOAc:isohexane, 1:10), filtered, washed with isohexane (5 mL) and dried to give the title compound (428 mg, 74%) as a white solid.

¹H NMR 2.86 (dd, 1H), 3.25 (obs dd, 1H), 3.89 (m, 2H), 4.72 (m, 1H), 5.39 (t, 1H), 5.51 (t, 1H), 7.17 (m, 5H), 8.13 (d, 1H), 8.59 (d, 1H), 12.35 (s, 1H); MS m/z 424.

Example 26

2,3-Dichloro-N-{(1S,2S)-1-[(methylsulfonyl)amino]-2,3-dihydro-1H-inden-2-yl}-4H-thieno[3,2-b]pyrrole-5-carboxamide

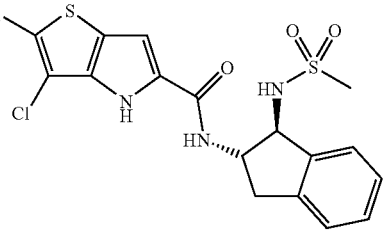

5-Carboxy-2,3-dichloro-4H-thieno[3,2-b]pyrrole (Method 4, 236 mg, 1.0 mmol), N-[(1S,2S)-2-amino-2,3-dihydro-1H-inden-1-yl]methanesulfonamide (226 mg, 1.0 mmol), DIPEA (174 µL, 1.0 mmol) and HOBT (135 mg, 1.0 mmol) were dissolved in DCM (10 mL) and stirred for approximately 5 mins. EDCI (240 mg, 1.25 mmol) was added and the reaction stirred for 20 hours. The volatiles were removed by evaporation, EtOAc (25 mL) added, the mixture washed with water (2×10 mL) and brine (10 mL) and dried (MgSO$_4$). The volatiles were removed by evaporation under reduced pressure to give the title compound (430 mg, 97%) as a foam.

¹H NMR 2.83 (m, 1H), 2.99 (s, 3H), 3.23 (m, 1H), 4.57 (m, 1H), 4.95 (m, 1H), 7.13 (s, 1H), 7.21–7.34 (m, 4H), 7.87 (d, 1H), 8.66 (d, 1H), 12.41 (s, 1H); MS m/z (M–H)$^-$442.

Example 27

2,3-Dichloro-N-{(1S,2S)-1-[methyl(morpholin-4-ylacetyl)amino]-2,3-dihydro-1H-inden-2-yl}-4H-thieno[3,2-b]pyrrole-5-carboxamide

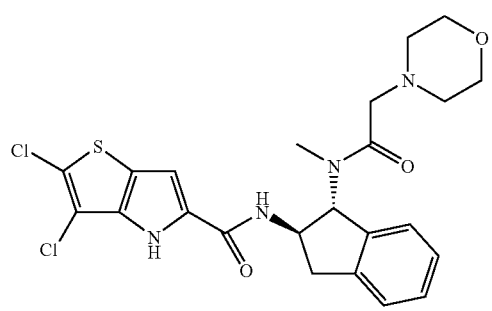

2,3-Dichloro-N-{(1R,2R)-1-[(chloroacetyl)(methyl)amino]-2,3-dihydro-1H-inden-2-yl}4H-thieno[3,2-b]pyrrole-5-carboxamide (Method 10, 100 mg, 0.22 mol) and morpholine (100 mg, 12.6 mmol) were dissolved in DCM, stirred at ambient temperature for 20 hours and the volatiles removed by evaporation under reduced pressure. EtOAc (10 mL) was added and the mixture washed with water (2×5 mL), brine (5 mL), dried (MgSO$_4$) and the volatiles removed by evaporation under reduced pressure to give the title compound (60 mg, 54%) as a buff coloured powder.

$^1$H NMR 2.36 (m, 4H), 2.74 (d, 3H), 2.9–3.55 (m, 7H), 4.8 (m, 1H), 5.96 (dd, 1H), 7.0 (m, 1H), 7.09 (d, 1H), 7.26 (m, 3H), 8.62 (dd, 1H); MS m/z 507.

Example 28

N-{(1R,2R)-1-[(2-Amino-2-oxoethyl)amino]-2,3-dihydro-1H-inden-2-yl}-2,3-dichloro-4H-thieno[3,2-b]pyrrole-5-carboxamide

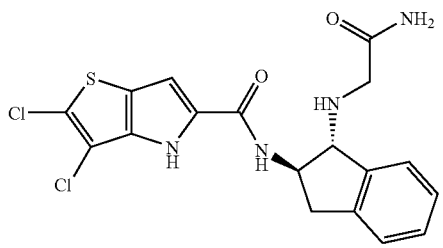

Prepared in a similar manner to Example 29 using N-{(1R,2R)-1-amino-2,3-dihydro-1H-inden-2-yl}-2,3-dichloro-4H-thieno[3,2-b]pyrrol-5-yl-2-carboxamide (Method 8) and bromoacetamide.

$^1$H NMR 2.69 (s, 1H), 2.8 (dd, 1H), 3.16 (m, 2H), 3.24 (m, 1H), 4.21 (m, 1H), 4.44 (m, 1H), 7.03 (s, 1H), 7.12 (s, 1H), 7.23 (m, 3H), 7.28 (s, 1H), 7.37 (s, 1H), 8.49 (d, 1H), 12.36 (s, 1H); MS m/z (M−H)$^-$422.

Example 29

N-{(1R,2R)-1-[(tert-Butoxycarbonylmethyl)amino]-2,3-dihydro-1H-inden-2-yl}-2,3-dichloro-4H-thieno[3,2-b]pyrrole-5-carboxamide

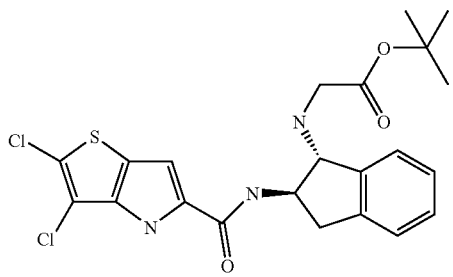

DIPEA (520 μL, 3.0 mmol) and t-butyl bromoacetate (150 μL, 1.0 mmol) were added to a solution of N-{(1R,2R)-1-amino-2,3-dihydro-1H-inden-2-yl}-2,3-dichloro-4H-thieno[3,2-b]pyrrol-5-yl-2-carboxamide (Method 8, 479 mg, 1.0 mmol) in CH$_3$CN (15 mL). The resulting suspension was stirred at 60° C. for approximately 2 h. Upon cooling the volatiles were removed by evaporation under reduced pressure, the residue dissolved in EtOAc (20 mL), washed with water (2×20 mL), brine (20 mL) and dried (MgSO$_4$). The volatiles were removed by evaporation under reduced pressure and the residue purified by column chromatography (EtOAc:isohexane 1:1) to afford the title compound (100 mg, 21%) as a white solid.

$^1$H NMR 1.49 (s, 9H), 1.87 (brs, 1H), 2.75 (dd, 1H), 3.62 (d, 2H), 3.65 (dd, 1H), 4.15 (d, 1H), 4.40 (m, 1H), 6.82 (s, 1H), 7.10 (d, 1H), 7.25 (s, 2H), 7.40 (d, 1H), 9.80 (s, 1H); MS m/z 480.

Example 30

N-[(1R,2R)-1-(Carboxymethylamino)-2,3-dihydro-1H-inden-2-yl]-2,3-dichloro-4H-thieno[3,2-b]pyrrole-5-carboxamide

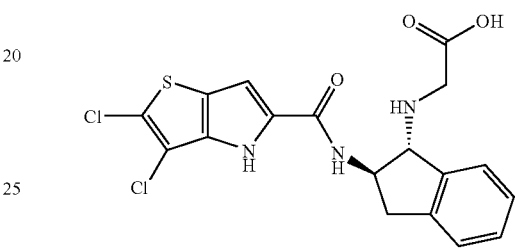

N-{(1R,2R)-1-[(tert-Butoxycarbonylmethyl) amino]-2,3-dihydro-1H-inden-2-yl}-2,3-dichloro-4H-thieno[3,2-b]pyrrole-5-carboxamide (Example 29; 100 mg, 0.21 mmol) dissolved in DCM (10 mL). TFA (1 mL) added and the reaction stirred at ambient temperature for 6 hours. Evaporation under reduced pressure, co-evaporation with CHCl$_3$ (2×10 mL) and drying gave the title compound (85 mg, 36%) as a white powder.

$^1$H NMR 2.71 (dd, 1H), 3.16 (dd, 1H), 3.29 (m, 2H), 4.25 (m, 1H), 4.39 (m, 1H), 6.97 (m, 2H), 7.08 (m, 3H), 7.24 (m, 2H), 7.48 (d, 1H), 8.63 (d, 1H), 11.62 (s, 1H); MS m/z (M−H)$^-$422.

Example 31

N-{(1R,2R)-1-[N-Acetyl-N-(carboxymethyl)amino]-2,3-dihydro-1H-inden-2-yl}-2,3-dichloro-4H-thieno[3,2-b]pyrrole-5-carboxamide

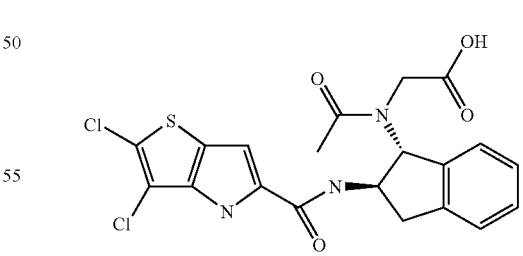

TFA (1 mL) was added to a solution of 1,1-dimethylethyl [acetyl((1R,2R)-2-{[(2,3-dichloro-4H-thieno[3,2-b]pyrrol-5-yl)carbonyl]amino}-2,3-dihydro-1H-inden-1-yl)amino] acetate (Method 18, 40 mg, 0.08 mmol) in DCM (5 mL) and the reaction was stirred at ambient temperature for 1 h. The volatiles were removed by evaporation under reduced pressure to afford the title compound (35 mg, 94%) as a white solid.

¹H NMR 2.49 (s, 3H), 2.97 (dd, 1H), 3.20 (dd, 1H), 3.90 (m, 2H), 4.70 (m, 1H), 5.50 (d, 1H), 7.25 (m, 5H), 8.60 (d, 1H), 12.43, (s, 1H); MS m/z 466, 349.

Example 32

N-{(1R,2R)-1-[Acetyl(2-amino-2-oxoethyl)amino]-2,3-dihydro-1H-inden-2-yl}-2,3-dichloro-4H-thieno[3,2-b]pyrrole-5-carboxamide

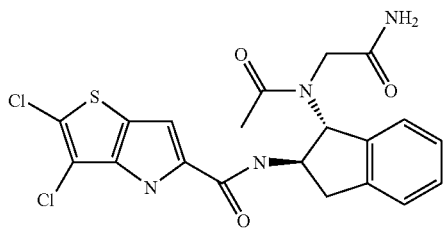

Acetyl chloride (17 μL, 0.24 mmol) was added to a solution of N-{(1R,2R)-1-[(2-amino-2-oxoethyl)amino]-2,3-dihydro-1H-inden-2-yl}-2,3-dichloro-4H-thieno[3,2-b]pyrrole-5-carboxamide (Example 28, 100 mg, 0.24 mmol) in THF (10 mL). The reaction was stirred at ambient temperature for 1 h. The volatiles were removed by evaporation under reduced pressure, the residue dissolved in EtOAc (50 mL), washed with water (2×10 mL), brine (10 mL) and dried (MgSO₄). The volatiles were removed by evaporation under reduced pressure and the residue purified by column chromatography (EtOAc:isohexane 1:2) to afford the title compound (50 mg, 45%) as a white solid.

¹H NMR 2.49 (s, 3H), 2.98 (dd, 1H), 3.20 (dd, 1H), 3.29 (brs, 2H), 4.0 (m, 2H), 4.65 (m, 1H), 5.70 (d, 1H), 7.25 (m, 5H), 8.30 (d, 1H), 12.10, (s, 1H); MS m/z 487.

Example 33

N-{(1R,2R)-1-[N-(Carboxymethyl)-N-(hydroxyacetyl)amino]-2,3-dihydro-1H-inden-2-yl}-2,3-dichloro-4H-thieno[3,2-b]pyrrole-5-carboxamide

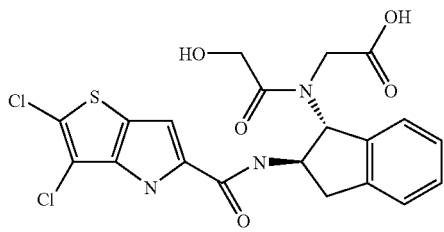

Potassium carbonate (20 mg) and MeOH (1 mL) were added to a solution of [[(acetyloxy)acetyl]((1R,2R)-2-{[(2,3-dichloro-4H-thieno[3,2-b]pyrrol-5-yl)carbonyl]amino}-2,3-dihydro-1H-inden-1-yl)amino]acetic acid (Method 19, 120 mg, 0.23 mmol) in THF (5 mL) and the reaction was stirred at ambient temperature for 24 h. The volatiles were removed by evaporation under reduced pressure, the residue dissolved in water and acidified to pH 2.0 and then extracted into EtOAc (3×10 mL). The volatiles were removed by evaporation under reduced pressure to afford the title compound (110 mg, 100%) as a white solid.

¹H NMR 3.07 (dd, 1H), 3.18 (dd, 1H), 3.92 (d, 1H), 4.35 (d, 1H), 4.82 (m, 3H), 5.96 (d, 1H), 7.25 (m, 5H), 8.67 (d, 1H), 12.40 (s, 1H); MS m/z 482.

Example 34

2-Chloro-N-[(1R,2R)-1-({[(2S)-5-oxotetrahydrofuran-2-yl]carbonyl}amino)-2,3-dihydro-1H-inden-2-yl]-6H-thieno[2,3-b]pyrrole-5-carboxamide

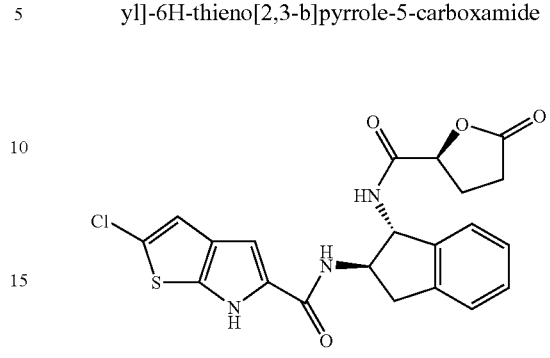

DIPEA (180 μL, 1.05 mmol), HOBT (68 mg, 0.5 mmol), (2S)-5-oxotetrahydrofuran-2-carboxylic acid (CAS Reg. No: [21461–84–7], 0.5 mmol, 65 mg) and EDAC (120 mg, 0.63 mmol) were added to a suspension of N-[(1R,2R)-1-amino-2,3-dihydro-1H-inden-2-yl]-2-chloro-6H-thieno[2,3-b]pyrrole-5-carboxamide (Method 21, 223 mg, 0.5 mmol) in anhydrous DCM (7 mL). The reaction was stirred at ambient temperature for approximately 16 h. The volatiles were removed by evaporation under reduced pressure, the residue dissolved in EtOAc (5 mL), washed with water (2×5 mL), brine (10 mL) and dried (MgSO₄). The volatiles were removed by evaporation under reduced pressure and the residue triturated (EtOAc:hexane, 1:10), collected by filtration, washed with hexane (2×5 mL) and dried to give the title compound (112 mg, 56%) as a brown solid.

¹H NMR 2.15 (m, 1H), 2.43 (m, 3H), 2.91 (dd, 1H), 3.25 (dd, 1H), 4.70 (m, 1H), 4.92 (m, 1H), 5.46 (t, 1H), 7.03 (s, 1H), 7.13 (m, 1H), 7.18 (s, 1H), 7.25 (m, 3H), 8.55 (d, 1H), 8.75 (s, 1H), 11.85 (s, 1H); MS m/z 444, 446

The following examples were made by a similar process to Example 34 using N-[(1R,2R)-1-amino-2,3-dihydro-1H-inden-2-yl]-2-chloro-6H-thieno[2,3-b]pyrrole-5-carboxamide (Method 21) and the appropriate commercially available carboxylic acid:

Example 35

2-Chloro-N-[(1R,2R)-1-(formylamino)-2,3-dihydro-1H-inden-2-yl]-6H-thieno[2,3-b]pyrrole-5-carboxamide

Example 36

2-Chloro-N-{(1R,2R)-1-[(methoxyacetyl)amino]-2,3-dihydro-1H-inden-2-yl}-6H-thieno[2,3-b]pyrrole-5-carboxamide

Example 37

N-[(1R,2R)-1-(Acetylamino)-2,3-dihydro-1H-inden-2-yl]-2-chloro-6H-thieno[2,3-b]pyrrole-5-carboxamide

Example 38

2-Chloro-N-{(1R,2R)-1-[(3-methoxypropanoyl)amino]-2,3-dihydro-1H-inden-2yl}-6H-thieno[2,3-b]pyrrole-5-carboxamide

Example 39

N-{(1R,2R)-1-[(2-Acetoxyacetyl)amino]-2,3-dihydro-1H-inden-2-yl}-2-chloro-6H-thieno[2,3-b]pyrrole-5-carboxamide

Example 40

N-((1R,2R)-1-{[(3R)-3-(tert-Butoxycarbonylamino)-3-carbamoylpropanoyl]amino}-2,3-dihydro-1H-inden-2-yl)-2-chloro-6H-thieno[2,3-b]pyrrole-5-carboxamide

Example 41

N-{(1R,2R)-1-[2-(tert-Butoxycarbonylamino)acetylamino]-2,3-dihydro-1H-inden-2-yl}-2-chloro-6H-thieno[2,3-b]pyrrole-5-carboxamide

Example 42

N-{(1R,2R)-1-[(2-Carbamoylacetyl)amino]-2,3-dihydro-1H-inden-2-yl}-2-chloro-6H-thieno[2,3-b]pyrrole-5-carboxamide

Example 56

N-{(1R,2R)-1-[2-(tert-Butoxycarbonyl)acetylamino]-2,3-dihydro-1H-inden-2-yl}-2-chloro-6H-thieno[2,3-b]pyrrole-5-carboxamide

Example 57

2-Chloro-N-((1R,2R)-1-{[3-hydroxy-2-(hydroxymethyl)propanoyl]amino}-2,3-dihydro-1H-iden-2-yl)-6H-thieno[2,3-b]pyrrole-5-carboxamide

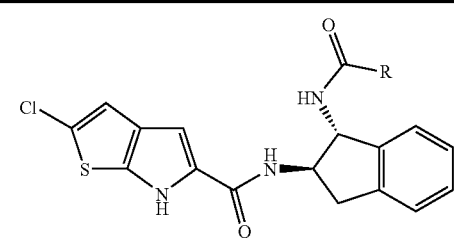

| Ex | R | NMR | M/z |
|---|---|---|---|
| 35 | H | (DMSO-$d_6$) 2.88 (dd, 1H), 3.21 (dd, 1H), 4.58 (m, 1H), 5.51 (t, 1H), 7.00 (s, 1H), 7.18 (m, 5H), 8.19 (s, 1H), 8.53 (d, 2H), 11.82 (s, 1H) | 358, 360 |
| 36 | $CH_2OMe$ | (DMSO-$d_6$) 2.88 (dd, 1H), 3.21 (dd, 1H), 3.30 (s, 3H), 3.86 (m, 2H), 4.71 (m, 1H), 5.51 (t, 1H), 6.99 (s, 1H), 7.15 (m, 5H), 8.23 (d, 1H), 8.50 (d, 1H), 11.82 (brs, 1H) | 404, 406 |
| 37 | Me | (DMSO-$d_6$) 1.88 (s, 3H), 2.84 (dd, 1H), 3.22 (dd, 1H), 4.53 (m, 1H), 5.44 (t, 1H), 6.99 (d, 1H), 7.17 (m, 5H), 8.32 (d, 1H), 8.51 (d, 1H), 11.82 (s, 1H); | 374, 376 |
| 38 | $CH_2CH_2OMe$ | (DMSO-$d_6$) 2.38 (m, 2H), 2.84 (dd, 1H), 3.20 (m, 4H), 3.55 (m, 2H), 4.55 (m, 1H), 5.47 (t, 1H), 6.99 (d, 1H), 7.15 (m, 5H), 8.33 (d, 1H), 8.50 (d, 1H), 11.81 (s, 1H) | 418, 420 |
| 39 | $CH_2OAc$ | (DMSO-$d_6$) 2.07 (s, 3H), 2.88 (dd, 1H), 3.23 (dd, 1H), 4.51 (q, 2H), 4.62 (m, 1H), 5.50 (t, 1H), 7.0 (d, 1H), 7.18 (m, 5H), 8.50 (t, 2H), 11.81 (s, 1H) | 432, 434 |
| 40 | ![NHBoc, NH2, structure] | (DMSO-$d_6$) 1.37 (s, 9H), 2.89 (dd, 1H), 3.05 (m, 2H), 3.57 (m, 1H), 4.24 (m, 1H), 5.53 (m, 1H), 5.46 (t, 1H), 6.70 (d, 1H), 6.98 (m, 2H), 7.18 (m, 5H), 8.28 (d, 1H), 8.52 (d, 1H), 11.82 (s, 1H) | 568, 570 |
| 41 | $CH_2NHBoc$ | — | 511, 513 |
| 42 | $CH_2C(O)NH_2$ | (DMSO-$d_6$) 2.86 (dd, 1H), 3.07 (m, 2H), 3.23 (dd, 1H), 4.55 (m, 1H), 5.47 (m, 1H), 6.98 (s, 1H), 7.0 (d, 1H), 7.19 (m, 5H), 7.38 (s, 1H), 8.49 (d, 1H), 8.53 (d, 1H), 11.82 (s, 1H). | 417, 419 |
| 56 | $CH_2CO_2tBu$ | (DMSO-$d_6$) 1.36 (s, 9H), 2.83 (m, 1H), 3.19 (m, 3H), 4.57 (m, 1H), 5.45 (t, 1H), 7.00 (s, 1H), 7.15 (s, 1H), 7.20 (m, 4H), 8.53 (t, 2H), 11.82 (s, 1H) | 474, 476 |
| 57 | OH, OH (structure) | (DMSO-$d_6$) 2.85 (dd, 1H), 3.22 (dd, 1H), 3.45 (m, 1H), 3.57 (m, 4H), 4.51 (m, 3H), 5.48 (m, 1H), 7.0 (s, 1H), 7.18 (m, 5H), 8.25 (d, 1H), 8.5 (d, 1H), 11.80 (s, 1H) | 433, 435 (M − H)⁻ |

Example 43

N-{(1R,2R)-1-[((3R)-3-Amino-3-carbamoylpropanoyl)amino]-2,3-dihydro-1H-inden-2-yl}-2-chloro-6H-thieno [2,3-b]pyrrole-5-carboxamide

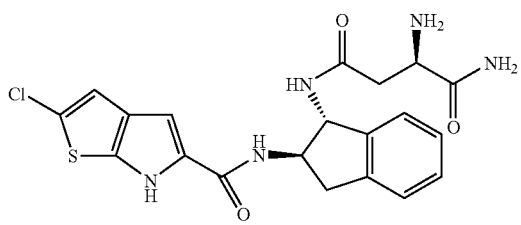

N-((1R,2R)-1-{[(3R)-3-(tert-Butoxycarbonylamino)-3-carbamoylpropanoyl]amino}-2,3-dihydro-1H-inden-2-yl)-2-chloro-6H-thieno[2,3-b]pyrrole-5-carboxamide (Example 40, 251 mg, 0.46 mmol) was dissolved in trifluoroacetic acid (4 mL) and stirred at ambient temperature for 24 hours. The volatiles were evaporated under reduced pressure and the crude material was azeotroped with chloroform (3×5 mL) to afford a gum. The gum was triturated with ether (5 mL), the solid collected by filtration, washed with ether (2×5 mL) and dried to give the trifluoroacetate salt of the title compound (239 mg, 93%) as a brown solid.

$^1$H NMR 2.75 (m, 2H), 2.90 (dd, 1H), 3.23 (dd, 1H), 4.04 (m, 1H), 4.59 (m, 1H), 5.50 (t, 1H), 7.00 (s, 1H), 7.19 (m, 5H), 7.54 (s, 1H), 7.74 (s, 1H), 8.05 (br s, 3H), 8.56 (d, 1H), 8.70 (d, 1H), 11.83 (s, 1H); MS m/z 468, 469.

Example 44

N-{(1R,2R)-1-[(Aminoacetyl)amino]-2,3-dihydro-1H-inden-2-yl}-2-chloro-6H-thieno[2,3-b]pyrrole-5-carboxamide

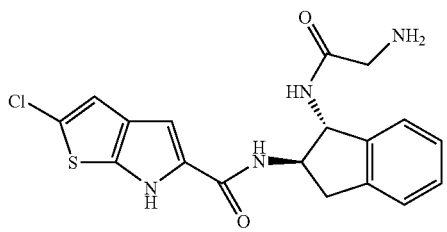

N-{(1R,2R)-1-[2-(tert-Butoxycarbonylamino) acetylamino]-2,3-dihydro-1H-inden-2-yl}-2-chloro-6H-thieno[2,3-b]pyrrole-5-carboxamide (Example 41; 366 mg, 0.75 mmol) was dissolved in dichloromethane (10 mL) and trifluoroacetic acid (0.5 mL) was added and the reaction stirred at ambient temperature for 7 hours. The volatiles were evaporated under reduced pressure and the crude solid was azeotroped with chloroform (3×5 mL), triturated with ether (5 mL), collected by filtration, washed with ether (2×5 mL) and dried to give the trifluoroacetate salt of the title compound (200 mg, 53%) as a brown solid.

$^1$H NMR 2.90 (dd, 1H), 3.21 (m, 1H), 3.65 (m, 2H), 4.59 (m, 1H), 5.51 (t, 1H), 6.99 (s, 1H), 7.19 (m, 5H), 8.08 (br, 3H), 8.58 (d, 1H), 8.84 (d, 1H); MS m/z 389, 391.

Example 45

2-Chloro-N-[(1R,2R)-1-({[(2-hydroxyethyl)(phenylmethyl)amino]acetyl}amino)-2,3-dihydro-1H-inden-2-yl]-6H-thieno[2,3-b]pyrrole-5-carboxamide

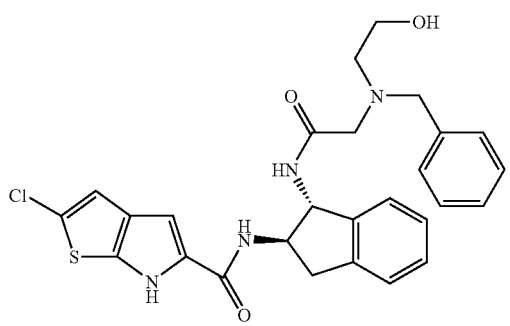

2-(Benzylamino)ethanol (160 mg, 1.06 mmol) was added to a solution of 2-chloro-N-{(1R,2R)-1-[(chloroacetyl)amino]-2,3-dihydro-1H-inden-2-yl}-6H-thieno[2,3-b]pyrrole-5-carboxamide (Method 23; 216 mg, 0.53 mmol) and Et$_3$N (500 μL, 3.60 mmol) in anhydrous THF (5 mL) and the reaction stirred for approximately 16 hours at room temperature then for a further 16 h at 50° C. The volatiles were removed under reduced pressure, the residue dissolved in EtOAc (10 mL), washed with H$_2$O (2×10 mL) and dried (MgSO$_4$). The solvent was removed under reduced pressure, the residue triturated (EtOAc:isohexane, 1:5), collected by filtration, washed with isohexane (10 mL) and dried to give the title compound (100 mg, 36%) as a brown solid.

$^1$H NMR 2.58 (t, 2H), 2.90 (dd, 1H), 3.09 (dd, 2H), 3.18 (dd, 1H), 3.50 (dd, 2H), 3.68 (dd, 2H), 4.55 (t, 1H), 4.65 (m, 1H), 5.46 (t, 1H), 6.99 (s, 1H), 7.04 (d, 1H), 7.23 (m, 9H), 8.38 (d, 1H), 8.53 (d, 1H), 11.81 (s, 1H); MS m/z 523, 525

The following examples were made by the process of Example 45 using 2-chloro-N-{(1R,2R)-1-[(chloroacetyl)amino]-2,3-dihydro-1H-inden-2-yl}-6H-thieno[2,3-b]pyrrole-5-carboxamide and the appropriate commercially available amine:

Example 46

2-Chloro-N-{(1R,2R)-1-[(morpholin-4-ylacetyl)amino]-2,3-dihydro-1H-inden-2-yl}-6H-thieno[2,3-b]pyrrole-5-carboxamide

Example 47

2-Chloro-N-((1R,2R)-1-({[(2-hydroxyethyl)(methyl)amino]acetyl}amino)-2,3-dihydro-1H-inden-2-yl)-6H-thieno[2,3-b]pyrrole-5-carboxamide

Example 48

N-((1R,2R)-1-({[Bis(2-hydroxyethyl)amino]acetyl}amino)-2,3-dihydro-1H-inden-2-yl)-2-chloro-6H-thieno[2,3-b]pyrrole-5-carboxamide

Example 49

2-Chloro-N-((1R,2R)-1-({[ethyl(2-hydroxyethyl)amino]acetyl}amino)-2,3-dihydro-1H-inden-2-yl)-6H-thieno[2,3-b]pyrrole-5-carboxamide

Example 50

2-Chloro-N-((1R,2R)-1-({[(2,3-dihydroxypropyl)(methyl)amino]acetyl}amino)-2,3-dihydro-1H-inden-2-yl)-6H-thieno[2,3-b]pyrrole-5-carboxamide

Example 51

N-((1R,2R)-1-({[Bis(2-hydroxypropyl)amino]acetyl}amino)-2,3-dihydro-1H-inden-2-yl)-2-chloro-6H-thieno[2,3-b]pyrrole-5-carboxamide

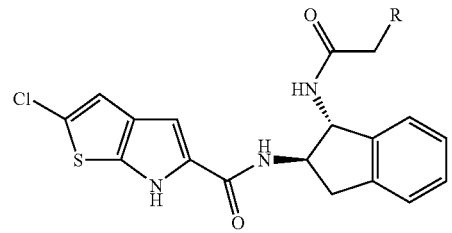

| Ex | R | NMR | M/z |
|---|---|---|---|
| 46 | morpholine-N-yl | (DMSO-$d_6$) 2.42 (m, 4H), 2.97 (m, 3H), 3.19 (dd, 1H), 3.55 (m, 4H), 4.69 (m, 1H), 5.44 (t, 1H), 6.98 (s, 1H), 7.09 (d, 1H), 7.14 (m, 4H), 8.13 (d, 1H), 8.50 (d, 1H), 11.80 (br s, 1H) | 459, 461 |
| 47 | N(CH₃)CH₂CH₂OH | (DMSO-$d_6$) 2.21 (s, 3H), 2.47 (m, 2H), 2.90 (dd, 1H), 3.03 (dd, 2H), 3.21 (dd, 1H), 3.44 (m, 2H), 4.43 (t, 1H), 4.66 (m, 1H), 5.49 (t, 1H), 6.99 (s, 1H), 7.19 (m, 5H), 8.25 (d, 1H), 8.52 (d, 1H), 11.81 (s, 1H) | 447, 449 |
| 48 | N(CH₂CH₂OH)₂ | (DMSO-$d_6$) 2.59 (m, 4H), 2.91 (dd, 1H), 3.17 (m, 3H), 3.43 (m, 4H), 4.23 (t, 2H), 4.62 (m, 1H), 5.47 (t, 1H), 6.99 (s, 1H), 7.18 (m, 5H), 8.34 (d, 1H), 8.53 (d, 1H), 11.81 (br s, 1H) | 447, 479 |
| 49 | N(CH₂CH₃)CH₂CH₂OH | (DMSO-$d_6$) 0.92 (t, 3H), 2.54 (m, 4H), 2.90 (dd, 1H), 3.07 (dd, 2H), 3.21 (m, 1H), 3.37 (m, 2H), 4.45 (t, 1H), 4.63 (m, 1H), 5.46 (t, 1H), 6.98 (s, 1H), 7.16 (m, 5H), 8.25 (d, 1H), 8.51 (d, 1H), 11.80 (s, 1H) | 461, 463 |
| 50 | N(CH₃)CH₂CH(OH)CH₂OH | (DMSO-$d_6$) 2.22 (s, 3H), 2.42 (m, 2H), 2.99 (m, 3H), 3.25 (obs m, 3H), 3.56 (m, 1H), 4.43 (m, 1H), 4.54 (m, 1H), 4.66 (m, 1H), 5.50 (t, 1H), 6.99 (s, 1H), 7.17 (m, 5H), 8.34 (d, 1H), 8.51 (m, 1H), 11.80 (s, 1H) | 477, 479 |
| 51 | N(CH₂CH(OH)CH₃)₂ | (DMSO-$d_6$) 0.96 (m, 6H), 2.35 (m, 4H), 2.88 (dd, 1H), 3.11 (dd, 1H), 3.67 (m, 2H), 4.49 (m, 2H), 4.60 (m, 1H), 5.47 (t, 1H), 6.99 (s, 1H), 7.17 (m, 5H), 8.69 8.49 (m, 2H), 11.77 (s, 1H) | 505, 507 |

Example 52

N-{(1R,2R)-1-[(2-Amino-2-oxoethyl)amino]-2,3-dihydro-1H-inden-2-yl}-2-chloro-6H-thieno[2,3-b]pyrrole-5-carboxamide

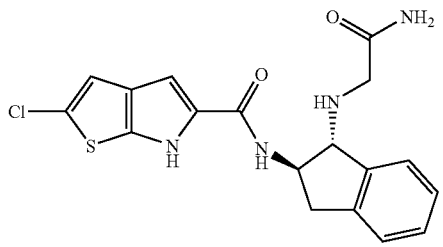

N-{(1R,2R)-1-Amino-2,3-dihydro-1H-inden-2-yl}-2-chloro-6H-thieno[2,3-b]pyrrol-5-yl)-2-carboxamide trifluoroacetic acid salt (Method 21, 225 mg, 0.5 mmol), DIPEA (216 μL, 1.5 mmol) and bromoacetamide (70 mg, 0.5 mmol) heated in a microwave at 180° C. for 3 mins. EtOAc (30 mL) was added and the mixture washed with water (2×10 mL), brine (10 mL), dried (MgSO₄) and evaporated. The residue was purified by column chromatography (EtOAc:MeOH 19:1) to afford the title compound (52 mg, 27%) as a white foam.

$^1$H NMR 2.68 (s, 1H), 2.79 (dd, 1H), 3.24 (m, 3H), 4.21 (m, 1H), 4.41 (m, 1H), 7.02 (m2H), 7.14 (s, 1H), 7.21 (m, 3H), 7.28 (m, 1H), 7.36 (m, 1H), 8.42 (d, 1H), 11.83 (s, 1H); MS m/z 389, 391.

Example 53

N-{(1R,2R)-1-[(tert-Butoxycarbonylmethyl)amino]-2,3-dihydro-1H-inden-2-yl}-2-chloro -6H-thieno[2,3-b]pyrrole-5-carboxamide

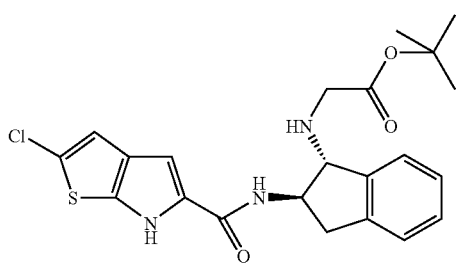

DIPEA (350 μL, 2.0 mmol) and t-butyl bromoacetate (90 μL, 0.7 mmol) were added to a solution of N-{(1R,2R)-1-amino-2,3-dihydro-1H-inden-2-yl}-2-chloro-6H-thieno[2,3-b]pyrrol-5-yl)-2-carboxamide (Method 21, 300 mg, 0.7 mmol) in CH₃CN (10 mL). The resulting suspension was stirred at 60° C. for approximately 2 h. Upon cooling the volatiles were removed by evaporation under reduced pressure, the residue dissolved in EtOAc (10 mL), washed with water (2×10 mL), brine (10 mL) and dried (MgSO₄). The volatiles were removed by evaporation under reduced pressure and the residue purified by column chromatography (EtOAc:isohexane 1:1) to afford the title compound (30 mg, 10%) as a white solid.

$^1$H NMR 1.45 (s, 9H), 2.11 (br s, 1H), 2.80 (dd, 1H), 3.60 (m, 3H), 4.27 (d, 1H), 4.46 (m, 1H), 6.8 (d, 2H), 7.10 (d, 1H), 7.30 (m, 4H), 11.35 (s, 1H); MS m/z 446, 448.

Example 54

N-{(1R,2R)-1-(Carboxymethylamino)-2,3-dihydro-1H-inden-2-yl}-2-chloro-6H-thieno[3,2-b]pyrrole-5-carboxamide

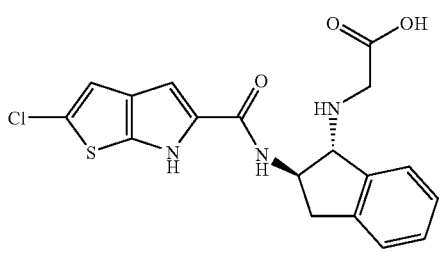

N-{(1R,2R)-1-[(tert-Butoxycarbonylmethyl)amino]-2,3-dihydro-1H-inden-2-yl}-2-chloro-6H-thieno[2,3-b]pyrrole-5-carboxamide (Example 53, 100 mg, 0.22 mmol), dissolved in DCM (5 mL). TFA (1 mL) added and the reaction stirred at ambient temperature for 20 hours. Evaporation under reduced pressure, co-evaporation with CHCl₃ (2×10 mL) and drying gave the trifluoroacetic acid salt of the title compound (110 mg, 99%) as a grey powder.

$^1$H NMR 3.1 (dd, 1H), 3.52 (dd, 1H), 4.2 (m, 2H), 4.9 (m, 2H), 7.05 (s, 1H), 7.2 (s, 1H), 7.4 (m, 3H), 7.7 (d, 1H), 8.76 (d, 1H), 9.73 (s, 2H), 12.02 (s, 1H), 13.9 (s, 1H); MS m/z (M–H)⁻ 388, 390.

Example 58

2-Chloro-N-{(1R,2R)-1-[(hydroxyacetyl)amino]-2,3-dihydro-1H-inden-2-yl}-6H-thieno[2,3-b]pyrrole-5-carboxamide

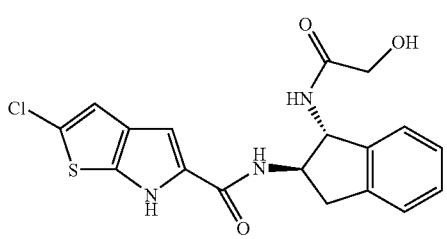

N-{(1R,2R)-1-[(2-Acetoxyacetyl)amino]-2,3-dihydro-1H-inden-2-yl}-2-chloro-6H-thieno[2,3-b]pyrrole-5-carboxamide (Example 39; 393 mg, 0.92 mmol) was dissolved in THF (5 mL), MeOH (5 mL) and K₂CO₃ (50 mg) were then added and the suspension stirred at ambient temperature for 4 hours. Water (10 mL) was added and the aqueous phase was extracted with EtOAc (3×10 mL). The combined organic phases were washed with water (50 mL), brine (50 mL) and dried (MgSO₄). The solvent was removed by evaporation under reduced pressure, the crude product was triturated (EtOAc:isohexane, 1:5), filtered, washed with isohexane (5 mL) and dried to give the title compound (257 mg, 72%) as a white solid.

¹H NMR 2.86 (dd, 1H), 3.23 (dd, 1H), 3.88 (dd, 2H), 4.70 (m, 1H), 5.39 (t, 1H), 5.50 (t, 1H), 7.00 (s, 1H), 7.18 (m, 5H), 8.10 (d, 1H), 8.51 (d, 1H), 11.81 (s, 1H); MS m/z 391, 393.

Example 59

2,3-Dichloro-N-{(1R,2R)-1-[(chloroacetyl)amino]-2,3-dihydro-1H-inden-2-yl}-4H-thieno [3,2-b]pyrrole-5-carboxamide

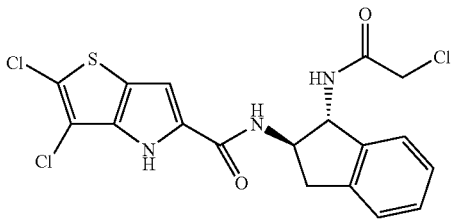

N-[(1R,2R)-1-Amino-2,3-dihydro-1H-inden-2-yl]-2,3-dichloro-4H-thieno[3,2-b]pyrrole-5-carboxamide (Method 8, 602 mg, 1.6 mmol) was dissolved in dichloromethane (30 mL), to this was added triethylamine (0.25 mL, 1.8 mmol) and chloroacetyl chloride (0.14 mL, 1.8 mmol). The solution was stirred at ambient temperature for 16 hours, after which triethylamine (0.25 ml, 1.8 mmol) and chloroacetyl chloride (0.14 ml, 1.8 mmol) were added before stirring for 1 hour. To the resulting slurry, water (15 mL) was added before filtering to give the title product (532 mg, 73%) as a cream solid.

¹H NMR 2.88 (m, 1H), 3.25 (m, 1H), 4.11 (s, 2H), 4.63 (m, 1H), 5.47 (t, 1H), 7.13 (m, 2H), 7.23 (m, 3H), 8.63 (d, 1H), 8.73 (d, 1H), 12.38 (s, 1H); MS m/z 442.

Example 60

N-{(1R,2R)-1-[((3S)-3-Amino-3-carboxypropanoyl)amino]-2,3-dihydro-1H-inden-2-yl}-2,3-dichloro-4H-thieno[3,2-b]pyrrole-5-carboxamide

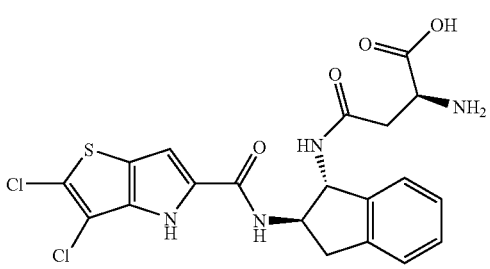

N-[(1R,2R)-1-Amino-2,3-dihydro-1H-inden-2-yl]-2,3-dichloro-4H-thieno[3,2-b]pyrrole-5-carboxamide (Method 8, 350 mg, 0.73 mmol) was added to a solution of N-alpha-t-Boc-L-aspartic acid alpha-t-butyl ester (232 mg, 0.80 mmol), 1-hydroxybenzotriazole monohydrate (123 mg, 0.80 mmol), 1-ethyl-3-(3-dimethylaminopropyl)carbodiimide hydrochloride (154 mg, 0.80 mmol), 4-methylmorpholine (0.18 mL, 1.6 mmol) in N,N-dimethylformamide (20 mL). The mixture was stirred at ambient temperature for 16 hours. The volatiles were removed by evaporation and the residue was dissolved in ethyl acetate (20 mL) and water (10 mL), the layers were separated before washing with 2M HCl then saturated NaHCO₃. Evaporation afforded a white solid which was redissolved in dichloromethane (5 mL) and trifluoroacetic acid (5 mL), the solution was allowed to stir at ambient temperature for 2 hours. The volatiles were removed by evaporation and the residue triturated with ether, collected by filtration, washed with ether (2×10 ml) and dried to give the title compound (210 mg, 48%) as a white solid.

¹H NMR 2.85 (m, 2H), 3.25 (m, 2H), 3.94 (t, 1H), 4.56 (m, 1H), 5.45 (t, 1H), 7.11 (s, 1H), 7.23 (m, 4H), 8.64 (d, 1H), 8.73 (d, 1H); MS m/z 481.

The following examples were prepared in a similar manner to Example 60 using N-[(1R,2R)-1-amino-2,3-dihydro-1H-inden-2-yl]-2,3-dichloro-4H-thieno3,2-b]pyrrole-5-carboxamide (Method 8) or N-{(1R,2R)-1-amino-2,3-dihydro-1H-inden-2-yl}-2-chloro-6H-thieno [2,3-b]pyrrol-5-yl)-2-carboxamide (Method 21) as the amine component and the appropriately protected carboxylic acid as starting material, prior to deprotection.

Example 61

N-{(1R,2R)-1-[(2-Carboxyacetyl)amino]-2,3-dihydro-1H-inden-2-yl}-2,3-dichloro-4H-thieno[3,2-b]pyrrole-5-carboxamide

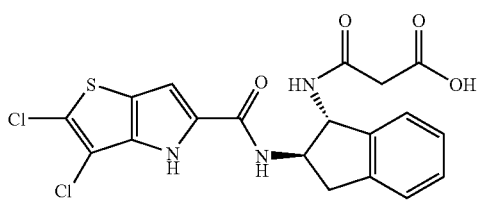

¹H NMR 2.84 (m, 1H), 3.25 (m, 3H), 4.56 (m, 1H), 5.47 (t, 1H), 7.11 (s, 1H), 7.20 (m, 4H), 8.59 (m, 1H), 12.36 (s, 1H); MS m/z 452.

Example 62

N-{(1R,2R)-1-[(2-Carboxyacetyl)amino]-2,3-dihydro-1H-inden-2-yl}-2-chloro-6H-thieno[3,2-b]pyrrole-5-carboxamide

Example 63

N-{(1R,2R)-1-[((3S)-3-Amino-3-carboxypropanoyl)amino]-2,3-dihydro-1H-inden-2-yl}-2-chloro-6H-thieno[3,2-b]pyrrole-5-carboxamide

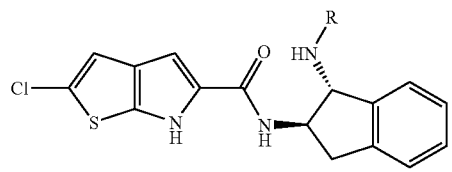

| Ex. | R | ¹H NMR | m/z |
|---|---|---|---|
| 62 | 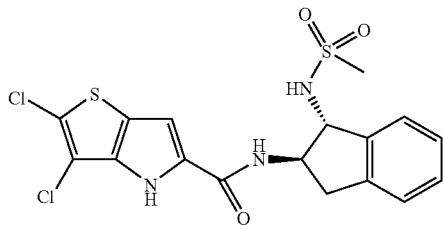 | 2.84 (m, 1H), 3.17 (m, 3H), 4.55 (m, 1H), 5.47 (t, 1H), 7.00 (s, 1H), 7.15 (s, 1H), 7.20 (m, 4H), 8.53 (t, 2H), 11.82 (s, 1H), 12.42 (s, 1H) | 419, 421 |
| 63 | | 2.64 (m, 1H), 2.85 (m, 2H), 3.23 (m, 1H), 4.00 (t, 1H), 4.56 (m, 1H), 5.45 (t, 1H), 7.00 (s, 1H), 7.15 (s, 1H), 7.23 (m, 4H), 8.53 (d, 1H), 8.71 (d, 1H) | 447, 449 |

Example 64

2,3-Dichloro-N-{(1R,2R)-1-[(methylsulfonyl)amino]-2,3-dihydro-1H-inden-2-yl}-4H-thieno[3,2-b]pyrrole-5-carboxamide N-[(1R,2R)-1-Amino-2,3-dihydro-1H-inden-2-yl]-2,3-dichloro-4H-thieno[3,2-b]pyrrole-5-carboxamide trifluoroacetate salt (Method 8, 223 mg, 0.5 mmol) was dissolved in THF (4 mL) and the solution cooled to 0° C. Et₃N (223 µL, 1.6 mmol) then methanesulfonyl chloride (43 µL, 0.55 mmol) were added and the reaction was stirred 0° C. for 5 mins. Saturated aqueous NaHCO₃ (5 mL) was added, the phases separated and the aqueous phase extracted with EtOAc (3×10 mL). The combined organic fractions were washed with H₂O (20 mL), dried (MgSO₄) and the solvent removed under reduced pressure. The residue was subjected to purification by reverse phase preparative HPLC to afford the title compound (30 mg, 15%) as a white solid.

¹H NMR 2.83 (dd, 1H), 2.98 (s, 3H), 3.22 (dd, 1H), 4.55 (m, 1H), 4.96 (t, 1H), 7.01 (s, 1H), 7.23 (m, 5H), 7.87 (d, 1H), 8.57 (d, 1H), 11.90 (s, 1H); MS m/z 410, 412.

Method 1

3-Chloro-5-methoxycarbonyl-4H-thieno[3,2-b]pyrrole

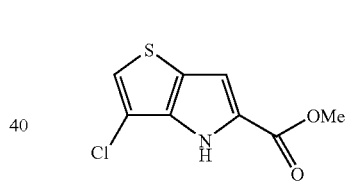

Methanolic sodium methoxide solution (28%) (5 ml, 25.9 mmol) was diluted with MeOH (5 ml) and was cooled to −25° C. under nitrogen. A solution of 4-chloro-2-thiophenecarboxaldehyde (J Heterocyclic Chem, 1976, 13, 393; 1.1 g, 7.5 mmol) and methyl azidoacetate (3.0 g, 26.1 mmol) in MeOH (20 ml) was added dropwise, maintaining the temperature at −25° C. On completion of addition the solution was allowed to warm to 5° C. over a period of approximately 16 hours. The solution was added to saturated aqueous ammonium chloride (250 ml) and the mixture was extracted using DCM. The combined organic layers were concentrated at 0° C. The residue was taken up in xylene (30 ml) and this solution was added dropwise to xylene (120 ml) under reflux. The solution was heated under reflux for 30 minutes before being cooled and concentrated. The title compound was purified by a mixture of crystallisation (EtOAc/isohexane) and chromatography on a Bond Elut column eluting with a graduated solvent of 5–50% EtOAc in isohexane (640 mg, 40%). NMR (CDCl₃) 9.1 (1H, br), 7.1 (2H, s), 3.9 (3H, s); m/z 214.3.

Method 2 and 2a

The following compounds were made by the process of Method 1 using the appropriate starting materials.

Method 2: 2,3-Dichloro-5-methoxycarbonyl-4H-thieno[3,2-b]pyrrole

Method 2a: 2-Chloro-5-methoxycarbonyl-6H-thieno[2,3-b]pyrrole

| Method | Compound | NMR (CDCl$_3$) | M/z |
|---|---|---|---|
| 2[1] | (Cl, S, Cl, N-H, C(=O)OMe structure) | 9.2 (1H, br), 7.0 (1H, s), 3.9 (3H, s) | 248.2 |
| 2a[2] | (Cl, S, N-H, C(=O)OMe structure) | 9.4–9.2 (1H, br), 7.0 (1H, s), 6.9 (1H, s), 3.9 (3H, s) | 214 |

[1] Aldehyde: DE 2814798
[2] Aldehyde: Gronowitz et al. Tetrahedron Vol.32 1976 p.1403

Method 3

5-Carboxy-3-chloro-4H-thieno[3,2-b]pyrrole

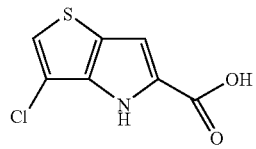

3-Chloro-5-methoxycarbonyl-4H-thieno[3,2-b]pyrrole (Method 1; 0.61 g, 2.83 mmol) was taken up in MeOH (10 ml) and was heated under reflux. Aqueous lithium hydroxide (2.0 M, 3.0 ml, 6.0 mmol) was added portionwise over 45 minutes. The mixture was heated under reflux for 30 minutes before being cooled and concentrated. Water (20 ml) was added and the solution was neutralised using aqueous hydrochloric acid (2.0 M, 3.0 ml). The solution was extracted using EtOAc, and the combined organic layers were concentrated to afford the title compound as a yellow solid (0.57 g, 100%). NMR: 12.4 (1H, br), 7.4 (1H, s), 7.0 (1H, s); m/z 200.3.

Method 4 and 4a

The following compounds were made by the process of Method 3 using Methods 2 and 2a as starting materials.

Method 4: 5-Carboxy-2,3-dichloro-4H-thieno[3,2-b]pyrrole
Method 4a: 5-Carboxy-2-chloro-6H-thieno[2,3-b]pyrrole

| Method | Compound | NMR | M/z | SM |
|---|---|---|---|---|
| 4 | (Cl, S, Cl, N-H, C(=O)OH structure) | 7.0 (1H, s) | 234.2 | Method 2 |
| 4a | (Cl, S, N-H, C(=O)OH structure) | 12.6–12.7 (1H, b), 12.0–12.1 (1H, b), 7.15 (1H, s), 6.9 (1H, s) | 183 | Method 2a |

Method 5

Cis-1-[(1,1-Dimethylethoxy)carbonylamino]-2 hydroxyindan

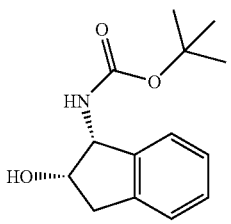

Cis-1-Amino-2-hydroxyindan (12.0 g, 80.5 mmol) was dissolved in DCM (500 ml) and triethylamine (22.4 ml, 161 mmol). Di-tert-butyl dicarbonate (22.0 g, 100 mmol) in DCM (50 ml) was added and the mixture stirred at room temperature for 20 hours then evaporated. EtOAc (200 ml) was added, the solution washed with water, dried over magnesium sulphate and evaporated. The crude product was purified by chromatography on silica with 4:1 iso-hexane: EtOAc as eluent to give the title compound (17.9 g, 90%) as a white solid.

$^1$H NMR 1.42 (s, 9H), 2.78 (dd, 1H), 3.00 (dd, 1H), 4.40 (m, 1H), 4.85 (m, 1H), 4.95 (m, 1H), 6.30 (d, 1H), 7.10 (m, 4H).

Method 6

Trans-2-Amino-1-[(1,1-dimethylethoxy)carbonylamino]indan

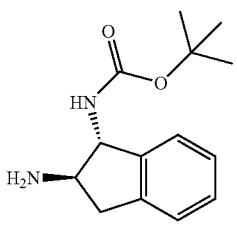

Cis-1-[(1,1-Dimethylethoxy)carbonylamino]-2-hydroxyindan (Method 5; 14.0 g, 56.2 mmol) was dissolved in DCM (200 ml) and triethylamine (11.8 ml, 84.3 mmol). Methanesulfonyl chloride (7.1 g, 61.9 mmol) dissolved in DCM (20 ml) was added and the mixture stirred at room temperature for 3 hours. The mixture was evaporated and EtOAc (250 ml) added. After washing with water and drying over magnesium sulphate the organic solution was evaporated to yield Cis-1-[(1,1-dimethylethoxy)carbonylamino]-2-methanesulphonyloxyindan (9.7 g, 98%) as a white solid.

$^1$H NMR 1.45 (s, 9H), 3.15 (m, 2H), 3.18 (s, 3H), 5.20 (m, 1H), 5.35 (m, 1H), 7.15 (m, 4H), 7.45 (d, 1H).

Cis-1-[(1,1-dimethylethoxy)carbonylamino]-2-methanesulphonyloxyindan (18.1 g, 55.3 mmol) was dissolved in dry dimethyl acetamide (100 ml). Sodium azide (5.4 g, 83.0 mmol) was added and the mixture heated to 90° C. for 6 hours. The reaction was cooled, diluted with ethyl acetate (150 ml), washed with water (6×200 ml) and dried over magnesium sulphate. 10% Palladium on activated carbon was added and the mixture stirred under a hydrogen atmosphere for 24 hours. Filtration through celite followed by evaporation gave the title compound (2.6 g, 98%) as a white solid.

$^1$H NMR: 1.45 (s, 9H), 2.50 (dd, 1H), 3.05 (dd, 1H), 3.30 (m, 3H), 4.55 (m, 1H), 7.1 (m, 5H).

Method 7

2,3-Dichloro-5-(N-{(1R,2R)-1-[N-(1,1-dimethylethoxy)carbonylamino]indan-2-yl}carbamoyl)-4H-thieno[3,2-b]pyrrole

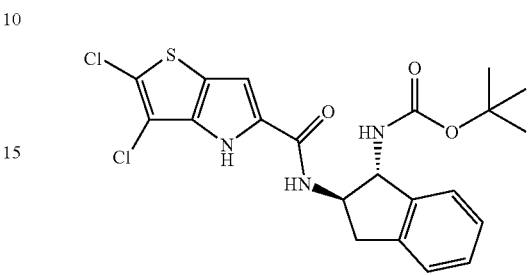

5-Carboxy-2,3-dichloro-4H-thieno[3,2-b]pyrrole (Method 4; 2.36 g, 10.0 mmol), trans-2-amino-1-{N-[(1,1-dimethylethoxy)]carbonylamino}indan (Method 6; 2.5 g, 10.0 mmol), DIPEA (1.7 ml, 10.0 mmol) and HOBT (1.35 g, 10.0 mmol) was stirred in DCM (75 ml) at room temperature for 2 minutes. EDCI (2.4 g, 12.5 mmol) was added and the mixture stirred at room temperature for 20 hours during which time the product precipitated. The reaction was filtered, washed with DCM (2×25 ml) and dried to give the title compound (3.7 g, 80%) as a pale green powder.

$^1$H NMR 1.40 (s, 9H), 2.81 (dd, 1H), 3.20 (dd, 1H), 4.55 (m, 1H), 5.15 (m, 1H), 7.15 (m, 5H), 7.35 (d, 1H), 8.55 (d, 1H), 12.36 (broad s, 1H); m/z 463.7/465.7.

Method 8

N-[(1R,2R)-1-Amino-2,3-dihydro-1H-inden-2-yl]-2,3-dichloro-4H-thieno[3,2-b]pyrrole-5-carboxamide

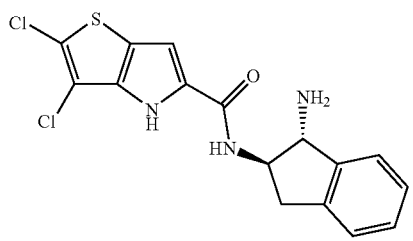

2,3-Dichloro-5-(N-{1-[(1,1-dimethylethoxy)carbonylamino]indan-2-yl}carbamoyl)-4H-thieno[3,2-b]pyrrole (Method 7; 3.7 g, 7.9 mmol) was dissolved in DCM (75 ml). Trifluoroacetic acid (10 ml) was added and the mixture stirred at room temperature for 24 hours. The reaction was filtered and the isolated solid washed with DCM to give the trifluoroacetic acid salt of the title compound (3.1 g, 82%) as a pale green powder.

$^1$H NMR 3.05 (dd, 1H), 3.42 (d, 1H), 4.7 (m, 2H), 7.20(d, 1H), 7.35 (m, 3H), 7.55 (d, 1H), 8.60 (broad s, 3H), 8.80 (d, 1H), 12.5 (broad s, 1H).

Method 9

N-[(1S,2S)-1-Amino-2,3-dihydro-1H-inden-2-yl]-2,3-dichloro-4H-thieno[3,2-b]pyrrole-5-carboxamide

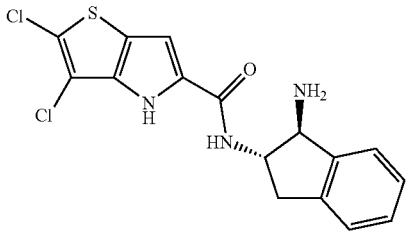

The title compound was prepared in an analogous fashion to Method 8.

¹H NMR 3.05 (dd, 1H), 3.42 (d, 1H), 4.7 (m, 2H), 7.20(d, 1H), 7.35 (m, 3H), 7.55 (d, 1H), 8.60 (broad s, 3H), 8.80 (d, 1H), 12.5 (broad s, 1H).

Method 10

2,3-Dichloro-N-{(1R,2R)-1-[(chloroacetyl)(methyl)amino]-2,3-dihydro-1H-inden-2-yl}-4H-thieno[3,2-b]pyrrole-5-carboxamide

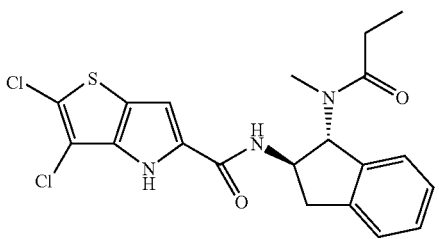

2,3-Dichloro-N-[(1R,2R)-1-(methylamino)-2,3-dihydro-1H-inden-2-yl]-4H-thieno[3,2-b]pyrrole-5-carboxamide (Method 11; 300 mg, 0.79 mmol) and triethylamine (167 μL, 1.2 mmol) was dissolved in DCM (5 mL), chloroacetyl chloride (73 μL, 0.9 mmol) added and the reaction stirred at ambient temperature for 2 hours. The volatiles were removed by evaporation under reduced pressure and EtOAc (15 mL) added. The mixture was washed with water (10 mL), brine (10 ml), dried (MgSO₄) and the volatiles were removed by evaporation under reduced pressure to give the title compound (310 mg, 86%) as a pale brown foam.

¹H NMR 2.73 (d, 3H), 2.98 (m, 1H), 3.24 (m, 1H), 4.45 (m, 2H), 4.82 (m, 1H), 5.77 (dd, 1H), 7.05 (m, 2H), 7.28 (m, 3H), 8.65 (m, 1H); MS m/z 456.

Method 11

2,3-Dichloro-N-[(1R,2R)-1-(methylamino)-2,3-dihydro-1H-inden-2-yl]-4H-thieno[3,2-b]pyrrole-5-carboxamide

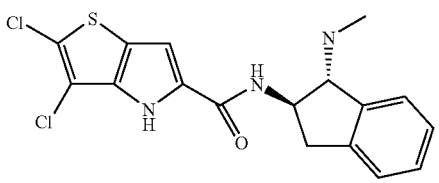

tert-Butyl((1R,2R)-2-{[(2,3-dichloro-4H-thieno[3,2-b]pyrrol-5-yl)carbonyl]amino}-2,3-dihydro-1H-inden-1-yl)methylcarbamate (Method 12; 900 mg, 1.87 mmol) was dissolved in DCM (20 mL), TFA (2 mL) added and the reaction stirred at ambient temperature for 1 hour. The volatiles were removed by evaporation under reduced pressure and the residue purified by ion exchange chromatography (MeOH:Water 1:1 then MeOH:Water:NH₄OH 1:1:0.05) to afford, after evaporation, the title compound (300 mg, 32%) as an off white powder.

¹H NMR 2.75 (s, 3H), 3.01 (dd, 1H), 3.49 (dd, 1H), 4.75 (m, 1H), 4.86 (m, 1H), 7.11 (d, 1H), 7.35 (m, 3H), 7.58 (d, 1H), 8.74 (d, 1H), 9.04 (m, 1H), 12.37 (s, 1H); MS m/z 380.

Method 12 tert-Butyl((1R,2R)-2-{[(2,3-dichloro-4H-thieno[3,2-b]pyrrol-5-yl)carbonyl]amino}-2,3-dihydro-1H-inden-1-yl)methylcarbamate

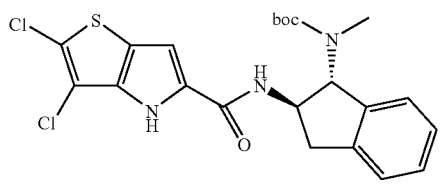

5-Carboxy-2,3-dichloro-4H-thieno[3,2-b]pyrrole (Method 4, 472 mg, 2.0 mmol), tert-butyl[(1R,2R)-2-amino-2,3-dihydro-1H-inden-1-yl]methylcarbamate (Method 13; 524 mg, 2.0 mmol), DIPEA (348 μL, 2.0 mmol), HOBT (270 mg, 2.0 mmol) and EDCI (480 mg, 2.5 mmol) were dissolved in DCM (10 mL) and stirred at ambient temperature for 20 hours. The volatiles were removed by evaporation under reduced pressure, the residue dissolved in EtOAc (50 mL), washed with water (3×25 mL), brine (25 mL) and dried (MgSO₄). The volatiles were removed by evaporation under reduced pressure to give the title compound (900 mg, 93%) as a pale brown foam.

¹H NMR 1.29 (m, 9H), 2.66 (s, 3H), 2.9–3.25 (m, 2H), 4.8 (m, 1H), 5.64 (m, 1H), 6.23–7.34 (m, 4H), 8.65 (m, 1H); MS m/z 480.

Method 13 tert-Butyl[(1R,2R)-2-amino-2,3-dihydro-1H-inden-1-yl]methylcarbamate

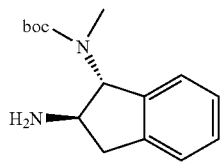

(1R,2S)-1-[(tert-Butoxycarbonyl)(methyl)amino]-2,3-dihydro-1H-inden-2-yl methanesulfonate (Method 14; 3.0 g, 8.8 mmol) and sodium azide (2.3 g, 35.2 mmol) in dry DMA (30 mL) was heated to 90° C. for 7 hours. The reaction was cooled and ethyl acetate (100 mL) added. The mixture was washed with water (6×25 mL), brine (50 mL) and dried (MgSO₄). 10% Palladium on carbon (400 mg) was added to the organic solution which was stirred under a hydrogen atmosphere for 4 h, filtered through Celite and evaporated. The residue was purified by column chromatography (EtOAc and then DCM:MeOH 9:1) to afford the title compound (1.2 g, 55%) as a pale brown oil.

¹H NMR 1.45 (m, 9H), 2.6 (s, 3H), 2.8 (m, 1H), 3.3 (m, 1H), 4.45 (m, 1H), 5.55 (dd, 1H), 7.26 (m, 4H); MS m/z 264.

Method 14

(1R,2S)-1-[(tert-Butoxycarbonyl)(methyl)amino]-2,3-dihydro-1H-inden-2-yl methanesulfonate

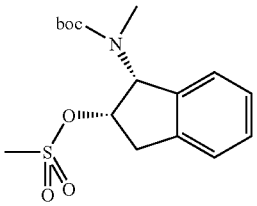

tert-Butyl [(1R,2S)-2-hydroxy-2,3-dihydro-1H-inden-1-yl]methylcarbamate (Method 15; 3.0 g, 11.4 mmol) was dissolved in dry THF (40 mL) at 10° C. A solution of methane sulphonyl chloride (1.44 g, 12.55 mmol) in dry THF (10 mL) was added, the reaction allowed to warm to ambient temperature and stirred for 30 mins. The volatiles were removed by evaporation under reduced pressure and ethyl acetate (100 mL) added. The mixture was washed with water (2×50 mL), brine (50 mL) and the organic phase was dried (MgSO$_4$), filtered and evaporated. The residue was purified by column chromatography (EtOAc:Hexane) to afford the title compound (3.1 g, 80%) as a colourless syrup.

$^1$HNMR 1.46 (s, 9H), 2.61 (s, 3H), 3.12 (m, 1H), 3.18 (s, 3H), 3.32 (m, 1H), 5.45 (m, 1H), 5.68 (m, 1H), 7.28 (m, 4H); MS m/z 342.

Method 15 tert-Butyl[(1R,2S)-2-hydroxy-2,3-dihydro-1H-inden-1-yl]methylcarbamate

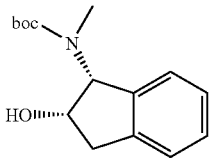

tert-Butyl methyl[(1R,2S)-2-(tetrahydro-2H-pyran-2-yloxy)-2,3-dihydro-1H-inden-1-yl]carbamate (Method 16; 4.0 g, 11.5 mmol) was dissolved in methanol (50 mL), 4-toluene sulphonic acid added and the reaction stirred at ambient temperature for 2 hours. Saturated NaHCO$_3$ (50 mL), water (100 mL) was added and ethyl acetate (100 mL) was added and the mixture stirred for 30 mins. The organic phase was separated, washed with water (50 mL), brine (50 mL) and dried (MgSO$_4$). The volatiles were removed by evaporation under reduced pressure to give the title compound (3.0 g, 99%) as an oil.

$^1$H NMR 1.45 (s, 9H), 2.6 (s, 3H), 2.75 (m, 1H), 3.05 (m, 1H), 4.5 (m, 1H), 5.05 (m, 1H), 5.34 (m, 1H), 7.03–7.3 (m, 4H).

Method 16 tert-Butyl methyl[(1R,2S)-2-(tetrahydro-2H-pyran-2-yloxy)-2,3-dihydro-1H-inden-1-yl]carbamate

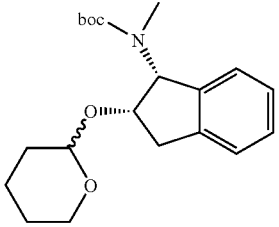

tert-Butyl [(1R,2S)-2-(tetrahydro-2H-pyran-2-yloxy)-2,3-dihydro-1H-inden-1-yl]carbamate (Method 17; 4.0 g, 12.0 mmol) was dissolved in dry DMA (25 mL) at 5° C. 60% Sodium hydride (575 mg, 14.4 mmol) was added, the reaction stirred at 5° C. for 30 mins, allowed to warm to ambient temperature and stirred for a further 30 mins. Methyl iodide (896 µL, 14.4 mmol) was added and the reaction stirred at ambient temperature for 3 hours. The reaction was poured into water (100 mL) and extracted with ethyl acetate (2×50 ml). The organic extracts were washed with water (6×25 mL), brine (50 mL) and dried (MgSO$_4$). The volatiles were removed by evaporation under reduced pressure to give the title compound (4.1 g, 97%) as an oil.

$^1$H NMR 1.4–1.9 (m, 6H), 1.5 (s, 9H), 2.7 (dd, 3H), 2.85–3.3 (m, 2H), 3.5 (m, 1H), 3.7–4.0 (m, 1H), 4.6–4.9 (m, 2H), 5.5–5.85 (m, 1H), 7.2 (s, 4H).

Method 17 tert-Butyl [(1R,2S)-2-(tetrahydro-2H-pyran-2-yloxy)-2,3-dihydro-1H-inden-1-yl]carbamate

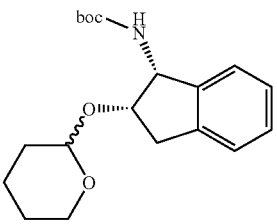

tert-Butyl [(1R,2S)-2-hydroxy-2,3-dihydro-1H-inden-1-yl]carbamate (Method 15, 7.0 g, 28.1 mmol) and 3,4-dihydro-2H-pyran (4.7 g, 56.2 mmol) dissolved in DCM (50 mL). 4-Toluene sulphonic acid pyridinium salt (100 mg) was added and the reaction stirred for 4 hours at ambient temperature. The reaction was diluted with ethyl acetate (100 mL), washed with water (2×50 mL), brine (50 mL) and dried (MgSO$_4$). The volatiles were removed by evaporation under reduced pressure to give the title compound (8.9 g, 95%) as an oil.

$^1$H NMR 1.25–1.85 (m, 6H), 1.45 (s, 9H), 2.85–3.1 (m, 2H), 3.4 (m, 1H), 3.8 (m, 1H), 4.35–5.1 (m, 3H), 6.8 (dd, 1H), 7.2(s, 1H).

Method 18

1,1-Dimethylethyl[acetyl((1R,2R)-2-{[(2,3-dichloro-4H-thieno[3,2-b]pyrrol-5-yl)carbonyl]amino}-2,3-dihydro-1H-inden-1-yl)amino]acetate

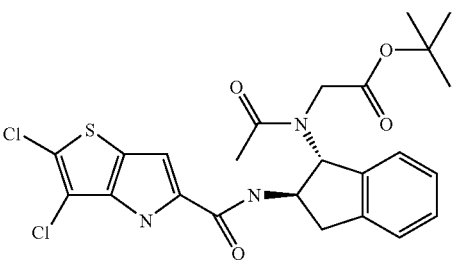

Acetyl chloride (7 µL, 0.1 mmol) was added to a solution of N-{(1R,2R)-1-[(tert-butoxycarbonylmethyl)amino]-2,3-dihydro-1H-inden-2-yl}-2,3-dichloro-4H-thieno[3,2-b]pyrrole-5-carboxamide (Example 29, 50 mg, 0.1 mmol) in THF (5 mL). The reaction was stirred at ambient temperature for 1 h. The volatiles were removed by evaporation under reduced pressure, the residue dissolved in EtOAc (5 mL), washed with water (2×5 mL), brine (10 mL) and dried (MgSO₄). The volatiles were removed by evaporation under reduced pressure and the residue purified by column chromatography (EtOAc:isohexane 1:1) to afford the title compound (168 mg, 76%) as a white solid.

¹H NMR 1.40 (s, 9H), 2.75 (dd, 1H), 3.42 (m, 2H), 3.60 (dd, 1H), 3.90 (s, 3H), 4.15 (d, 1H), 4.45 (m, 1H), 6.83 (d, 1H), 7.20 (m, 4H), 7.70 (d, 1H), 9.70 (s, 1H); MS m/z 522.

Method 19

[[(Acetyloxy)acetyl]((1R,2R)-2-{[(2,3-dichloro-4H-thieno[3,2-b]pyrrol-5-yl)carbonyl]amino}-2,3-dihydro-1H-inden-1-yl)amino]acetic acid

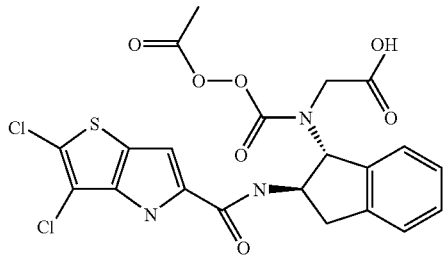

TFA (3 mL) was added to a solution of 1,1-dimethylethyl [[(acetyloxy)acetyl]((1R,2R)-2-{[(2,3-dichloro-4H-thieno[3,2-b]pyrrol-5-yl)carbonyl]amino}-2,3-dihydro-1H-inden-1-yl)amino]acetate (Method 20, 130 mg, 0.25 mmol) in DCM (10 mL) and the reaction was stirred at ambient temperature for 2 h. The volatiles were removed by evaporation under reduced pressure to afford the title compound (130 mg, 99%) as a white solid.

¹H NMR 2.20 (s, 3H), 2.78 (dd, 1H), 3.32 (dd, 1H), 3.97 (m, 2H), 4.35 (d, 1H), 4.68 (m, 2H), 4.90 (d, 1H), 6.42 (d, 1H), 6.83 (s, 1H), 7.25 (m, 4H), 11.14, (s, 1H); MS m/z 524.

Method 20

1,1-Dimethylethyl[[(acetyloxy)acetyl]((1R,2R)-2-{[(2,3-dichloro-4H-thieno[3,2-b]pyrrol-5-yl)carbonyl]amino}-2,3-dihydro-1H-inden-1-yl)amino]acetate

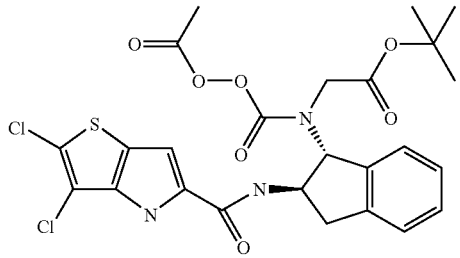

Acetoxyacetic acid (34 mg, 0.3 mmol) and DMTMM (81 mg, 0.3 mmol) were added to a solution of N-{(1R,2R)-1-[(tert-butoxycarbonylmethyl)amino]-2,3-dihydro-1H-inden-2-yl}-2,3-dichloro-4H-thieno[3,2-b]pyrrole-5-carboxamide (Example 29, 140 mg, 0.3 mmol) in THF (10 mL). The reaction was stirred at ambient temperature for 7 h. The volatiles were removed by evaporation under reduced pressure, the residue dissolved in EtOAc (10 mL), washed with water (2×5 mL), brine (10 mL) and dried (MgSO₄). The volatiles were removed by evaporation under reduced pressure to afford the title compound (145 mg, 83%) as a white solid.

¹H NMR 1.45 (s, 9H), 2.10 (s, 3H), 2.75 (dd, 1H), 3.50 (m, 3H), 3.90 (m, 2H), 4.15 (d, 1H), 4.50 (m, 1H), 6.83 (s, 1H), 7.20 (m, 4H), 7.70 (d, 1H), 9.70 (s, 1H); MS m/z 580.

Method 21

N-[(1R,2R)-1-Amino-2,3-dihydro-1H-inden-2-yl]-2-chloro-6H-thieno[2,3-b]pyrrole-5-carboxamide

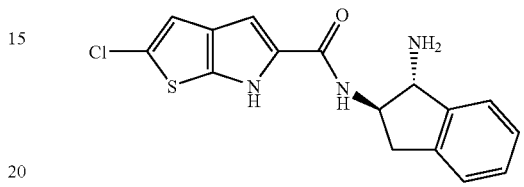

tert-Butyl((1R,2R)-2-{[(2-Chloro-6H-thieno[2,3-b]pyrrol-5-yl)carbonyl]amino}-2,3-dihydro-1H-inden-1-yl)carbamate (Method 22, 10.6 g, 24.5 mmol) was suspended in DCM (200 mL), TFA (20 mL) added and the reaction stirred at ambient temperature for 20 hours. The volatiles were removed by evaporation under reduced pressure and the residue triturated with DCM (50 mL) then filtered and dried to give the title compound (10.9 g, 100%) as the trifluoroacetic acid salt.

¹H NMR 3.03 (dd, 1H), 3.38 (dd, 1H), 4.7 (m, 2H), 7.06 (d, 1H), 7.17 (s, 1H), 7.35 (m, 3H), 7.55 (m, 1H), 8.55 (s, 3H), 8.68 (d, 1H), 11.9 (s, 1H); MS m/z (M−NH₃) ⁺315, 317.

Method 22 tert-Butyl((1R,2R)-2-{[(2-chloro-6H-thieno[2,3-b]pyrrol-5-yl)carbonyl]amino}-2,3-dihydro-1H-inden-1-yl)carbamate

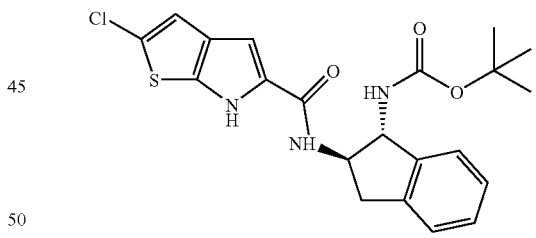

2-Chloro-5-carboxy-6H-thieno[3,2-b]pyrrole (Method 4a, 5.0 g, 25.0 mmol), trans-2-amino-1-[(1,1-dimethylethoxy)carbonylamino]indan (Method 6, 6.25 g, 25.0 mmol), DIPEA (4.35 mL, 25.0 mmol) and HOBT (3.4 g, 25.0 mmol) were dissolved in DCM (200 mL) and stirred for 5 mins. EDCI (6.0 g, 31.0 mmol) was added, the reaction stirred for 24 hours and evaporated under reduced pressure. EtOAc (150 mL) was added and the mixture filtered, washed with water (2×200 mL), brine (200 mL), dried (MgSO₄) and the volatiles removed by evaporation under reduced pressure to give the title compound (10.6 g, 98%) as a brown solid.

¹H NMR 1.38 (s, 9H), 2.81 (dd, 1H), 3.17 (dd, 1H), 4.56 (m, 1H), 5.14 (m, 1H), 7.01 (s, 1H), 7.16 (m, 5H), 7.32 (d, 1H), 8.47 (d, 1H), 11.82 (s, 1H).

Method 23

2-Chloro-N-{(1R,2R)-1-[(chloroacetyl)amino]-2,3-dihydro-1H-inden-2-yl}-6H-thieno[2,3-b]pyrrole-5-carboxamide

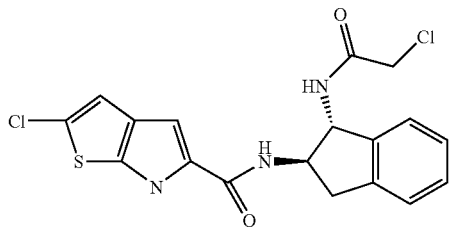

Et$_3$N (3 mL, 21.6 mmol) was added to a suspension of N-[(1R,2R)-1-amino-2,3-dihydro-1H-inden-2-yl]-2-chloro-6H-thieno[2,3-b]pyrrole-5-carboxamide (Method 21, 3.11 g, 6.98 mmol) in anhydrous dichloromethane (55 mL) and stirred at ambient temperature for 5 miuntes. The suspension was cooled to −78° C. and chloroacetylchloride (611 μL, 7.68 mmol) was added and the reaction was warmed to 0° C. and stirred at this temperature for 3 hours. NaHCO$_3$ (50 mL) was added, the phases were separated and the aqueous phase was extracted with THF (2×50 mL). The combined organic fractions were washed with water (100 mL), dried (MgSO$_4$) and the solvent removed under reduced pressure. The residue was triturated (THF:isohexane, 1:5), collected by filtration, washed with hexane (20 mL) and dried to give the title compound (1.92 mg, 68%) as a brown solid.

$^1$H NMR 2.88 (dd, 1H), 3.24 (dd, 1H), 4.11 (dd, 2H), 4.61 (m, 1H), 5.46 (t, 1H), 6.99 (s, 1H), 7.20 (m, 5H), 8.55 (d, 2H), 8.73 (d, 1H), 11.84 (s, 1H); MS m/z 408, 410.

The invention claimed is:

1. A compound of formula (1):

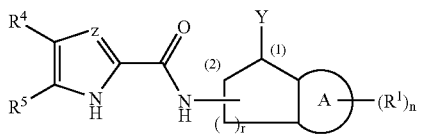

wherein

Z is CH;

R$^4$ and R$^5$ together are —S—C(R$^6$)═C(R$^7$)— or —C(R$^7$)═C(R$^6$)—S— wherein one of R$^6$ and R$^7$ is chloro and the other is hydrogen or both R$^6$ and R$^7$ are chloro;

A is phenylene or heteroarylene;

n is 0, 1, or 2;

R$^1$ is independently selected from halo, nitro, cyano, hydroxy, carboxy, carbamoyl, N-C$_{1-4}$alkylcarbamoyl, N,N-(C$_{1-4}$alkyl)$_2$carbamoyl, sulphamoyl, N-C$_{1-4}$alkylsulphamoyl, N,N-(C$_{1-4}$alkyl)$_2$sulphamoyl, —S(O)$_b$C$_{1-4}$alkyl (wherein b is 0, 1, or 2), C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, hydroxyC$_{1-4}$alkyl, fluoromethyl, difluoromethyl, trifluoromethyl, and trifluoromethoxy; or when n is 2, the two R$^1$ groups, together with the carbon atoms of A to which they are attached, may form a 4- to 7-membered ring, optionally containing 1 or 2 heteroatoms independently selected from O, S, and N, and optionally substituted with one or two methyl groups;

r is 1 or 2;

when r is 1 the group

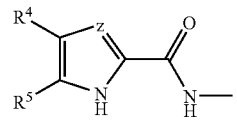

is a substituent on carbon (2);

when r is 2 (thereby forming a six-membered ring) the same group is a substituent on carbon (2) or on carbon (3);

Y is —NR$^2$R$^3$ or —OR$^3$;

R$^2$ and R$^3$ are independently selected from hydrogen, hydroxy, C$_{1-4}$alkoxy, C$_{1-4}$alkanoyl, carbamoyl, C$_{3-7}$cycloalkyl (optionally substituted with 1 or 2 hydroxy groups), cyano(C$_{1-4}$)alkyl, heterocyclyl, aryl, C$_{1-4}$alkyl [optionally substituted with 1 or 2 R$^8$ groups], —COR$^8$, —SO$_b$R$^8$ (wherein b is 0, 1, or 2), and groups of the formulae B and B':

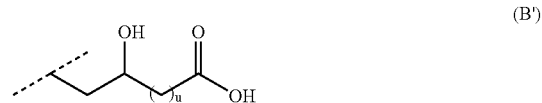

wherein y is 0 or 1, t is 0, 1, 2, or 3 and u is 1 or 2;

provided that the hydroxy group is not a substituent on the ring carbon adjacent to the ring oxygen; or NR$^2$R$^3$ may form a 4- to 7-membered saturated, partially saturated, or unsaturated ring, optionally containing 1, 2, or 3 additional heteroatoms independently selected from N, O and S, wherein any —CH$_2$— may optionally be replaced by —C(═O)—, and any N or S atom may optionally be oxidised to form an N-oxide, SO, or SO$_2$ group respectively, and the ring is optionally substituted with 1 or 2 substituents independently selected from halo, cyano, C$_{1-4}$alkyl, hydroxy, C$_{1-4}$alkoxy, and C$_{1-4}$alkylS(O)$_b$— (wherein b is 0, 1, or 2);

R$^8$ is independently selected from hydrogen, hydroxy, C$_{1-4}$alkyl, C$_{2-4}$alkenyl, C$_{1-4}$alkoxy, cyano(C$_{1-4}$)alkyl, amino(C$_{1-4}$)alkyl [optionally substituted on nitrogen with 1 or 2 groups selected from C$_{1-4}$alkyl, hydroxy, hydroxy(C$_{1-4}$)alkyl, dihydroxy(C$_{1-4}$)alkyl, —CO$_2$C$_{1-4}$alkyl, aryl, and aryl(C$_{1-4}$alkyl], halo(C$_{1-4}$alkyl, dihalo(C$_{1-4}$)alkyl, trihalo(C$_{1-4}$)alkyl, hydroxy(C$_{1-4}$)alkyl, dihydroxy(C$_{1-4}$)alkyl, C$_{1-4}$alkoxyC$_{1-4}$alkoxy, C$_{1-4}$alkoxyC$_{1-4}$alkyl, hydroxyC$_{1-4}$alkoxy, 5- and 6-membered cyclic acetals and mono- and di-methyl derivatives thereof, aryl, heterocyclyl, (heterocyclyl) C$_{1-4}$alkyl, C$_{3-7}$cycloalkyl (optionally substituted with 1 or 2 hydroxy groups, C$_{1-4}$alkyl, or —C(O)OC$_{1-4}$alkyl), C$_{1-4}$alkanoyl, C$_{1-4}$alkylS(O)$_b$— (wherein b is 0, 1, or 2), C$_{3-6}$cycloalkylS(O)$_b$— (wherein b is 0, 1, or 2), arylS(O)$_b$— (wherein b is 0, 1, or 2), heterocyclylS (O)$_b$— (wherein b is 0, 1, or 2), benzylS(O)$_b$— (wherein b is 0, 1, or 2), C$_{1-4}$alkylS(O)$_c$(C$_{1-4}$)alkyl (wherein c is 0, 1, or 2), —N(OH)CHO, —C(═N—

OH)NH$_2$, —C(=N—OH)NHC$_{1-4}$alkyl, —C(=N—OH)N(C$_{1-4}$alkyl)$_2$, —C(=N—OH)NHC$_{3-6}$cycloalkyl, —C(=N—OH)N(C$_{3-6}$cycloalkyl)$_2$, —COCOOR$^9$, —C(O)N(R$^9$)(R$^{10}$), —NHC(O)R$^9$, —C(O)NHSO$_2$(C$_{1-4}$alkyl), —NHSO$_2$R$^9$, (R$^9$)(R$^{10}$)NSO$_2$—, —COCH$_2$OR$^{11}$, (R$^9$)(R$^{10}$)N—, —COOR$^9$, —CH$_2$OR$^9$, —CH$_2$COOR$^9$, —CH$_2$OCOR$^9$, —CH$_2$CH(CO$_2$R$^9$)OH, —CH$_2$C(O)NR$^9$R$^{10}$, —(CH$_2$)$_w$CH(NR$^9$R$^{10}$)CO$_2$R$^{9'}$ (wherein w is 1, 2, or 3), and —(CH$_2$)$_w$CH(NR$^9$R$^{10}$)CO(NR$^{9'}$R$^{10'}$) (wherein w is 1, 2, or 3);

R$^9$, R$^{9'}$, R$^{10}$, and R$^{10'}$ are independently selected from hydrogen, hydroxy, C$_{1-4}$alkyl (optionally substituted with 1 or 2 R$^{13}$), C$_{2-4}$alkenyl, C$_{3-7}$cycloalkyl (optionally substituted with 1 or 2 hydroxy groups), cyano(C$_{1-4}$)alkyl, trihaloalkyl, aryl, heterocyclyl, heterocyclyl(C$_{1-4}$alkyl), and —C(=O)O(C$_{1-4}$alkyl; or R$^9$ and R$^{10}$ together with the nitrogen to which they are attached, or R$^{9'}$ and R$^{10'}$ together with the nitrogen to which they are attached, form a 4- to 6-membered ring where the ring is optionally substituted on carbon with 1 or 2 substituents independently selected from oxo, hydroxy, carboxy, halo, nitro, cyano, carbonyl, C$_{1-4}$alkoxy, and heterocyclyl; or the ring may be optionally substituted on two adjacent carbons with —O—CH$_2$—O— to form a cyclic acetal wherein one or both of the hydrogens of the —O—CH$_2$—O— group may be replaced by a methyl;

R$^{13}$ is selected from halo, trihalomethyl, and C$_{1-4}$alkoxy; and

R$^{11}$ is independently selected from hydrogen, C$_{1-4}$alkyl, and hydroxyC$_{1-4}$alkyl;

or a pharmaceutically acceptable salt or pro-drug thereof; with the proviso that the compound of formula (1) is not i) 2,3-dichloro-5-(N-{1-[N-(1,1-dimethylethoxy)carbonylamino]indan-2-yl}carbamoyl) -4H-thieno[3,2-b]pyrrole;

ii) 5-[N-(1-aminoindan-2-yl)carbamoyl]-2,3-dichloro-4H-thieno[3,2-b]pyrrole;

iii) 5-[N-(1-acetamidoindan-2-yl)carbamoyl]-2,3-dichloro-4H-thieno[3,2-b]pyrrole;

iv) 2,3-dichloro-5-{N-[1-(methanesulphonamido)indan-2-yl]carbamoyl}-4H-thieno[3,2-b]pyrrole;

v) 2,3-dichloro-5-{N-[1-(methylamino)indan-2-yl]carbamoyl}-4H-thieno[3,2-b]pyrrole;

vi) 2,3-dichloro-5-{N-[1-(methylacetamido)indan-2-yl]carbamoyl}-4H-thieno[3,2-b]pyrrole;

vii) 2,3-dichloro-5-[N-(1-hydroxyindan-2-yl)carbamoyl]-4H-thieno[3,2-b]pyrrole;

viii) 2-chloro-5-[N-(1-hydroxyindan-2-yl)carbamoyl]-6H-thieno[2,3-b]pyrrole;

ix) 2,3-dichloro-5-[N-(6-fluoro-1-hydroxyindan-2-yl)carbamoyl]-4H-thieno[3,2-]pyrrole;

x) 2,3-dichloro-5-[N-(1-methoxyindan-2-yl)carbamoyl]-4H-thieno[3,2-b]pyrrole; or xi) 2,3-dichloro-5-[N-(1-hydroxy-1,2,3,4-tetrahydronaphth-2-yl)carbamoyl]-4H-thieno[3,2-b]pyrrole.

2. A compound of claim 1, wherein

R$^2$ and R$^3$ are independently selected from hydrogen, hydroxy, C$_{1-4}$alkyl [optionally substituted with 1 or 2 R$^8$ groups], C$_{3-7}$cycloalkyl (optionally substituted with 1 or 2 hydroxy groups), cyano(C$_{1-4}$)alkyl, phenyl, morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopydridyl, 2-oxopyrrolidyl, 4-oxothiazolidyl, furyl, thienyl, oxazolyl, 1,3,4-oxadiazolyl, and 1,2,4-oxadiazolyl, tetrahydrothiopyranyl, 1-oxotetrahydrothiopyranyl, 1,1-dioxotetrahydrothiopyranyl, —COR$^8$, and —SO$_b$R$^8$ (wherein b is 0, 1, or 2);

R$^8$ is independently selected from hydrogen, hydroxy, C$_{1-4}$alkoxy, C$_{1-4}$alkoxyC$_{1-4}$alkyl, C$_{1-4}$alkoxy C$_{1-4}$alkoxy, hydroxyC$_{1-4}$alkoxy, C$_{1-4}$alkyl, amino (C$_{1-4}$)alkyl [optionally substituted on nitrogen with 1 or 2 groups selected from C$_{1-4}$alkyl, hydroxy(C$_{1-4}$)alkyl, dihydroxy(C$_{1-4}$)alkyl, —CO$_2$C$_{1-4}$alkyl, aryl, and aryl(C$_{1-4}$alkyl], C$_{2-4}$alkenyl, C$_{3-7}$cycloalkyl (optionally substituted with —C(O)OC$_{1-4}$alkyl), 5- and 6-membered cyclic acetals and mono- and di-methyl derivatives thereof, halo(C$_{1-4}$)alkyl, dihalo(C$_{1-4}$)alkyl, trihalo (C$_{1-4}$)alkyl, hydroxy(C$_{1-4}$)alkyl, dihydroxy(C$_{1-4}$)alkyl, cyano(C$_{1-4}$)alkyl, heterocyclyl, heterocyclylC$_{1-4}$alkyl, aryl, C$_{1-4}$alkylS(O)$_b$— (wherein b is 0, 1, or 2), C$_{3-6}$cycloalkylS(O)$_b$— (wherein b is 0, 1, or 2), arylS(O)$_b$— (wherein b is 0, 1, or 2), heterocyclylS(O)$_b$— (wherein b is 0, 1, or 2), benzylS(O)$_b$— wherein b is 0,1, or 2), C$_{1-4}$alkylS(O)$_c$(C$_{1-4}$alkyl (wherein c is 0, 1, or 2), —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10}$)CO$_2$R$^{9'}$, and —CH$_2$OCOR$^9$;

R$^9$, R$^{9'}$, R$^{10}$, and R$^{10'}$ are independently selected from hydrogen, C$_{1-4}$alkyl (optionally substituted with 1 or 2 R$^{13}$), C$_{3-7}$cycloalkyl (optionally substituted with 1 or 2 hydroxy groups), —C(=O)O$^t$Bu, C$_{2-4}$alkenyl, cyano (C$_{1-4}$)alkyl, and phenyl (optionally substituted with 1 or 2 groups selected from nitro, halo, hydroxy, and cyano); or R$^9$ and R$^{10}$ together with the nitrogen to which they are attached, or R$^{9'}$ and R$^{10'}$ together with the nitrogen to which they are attached, form a 4- to 6-membered ring where the ring is optionally substituted on carbon with 1 or 2 substituents independently selected from oxo, hydroxy, carboxy, halo, nitro, cyano, carbonyl, and C$_{1-4}$alkoxy; or the ring may be optionally substituted on two adjacent carbons with —O—CH$_2$—O— to form a cyclic acetal wherein one or both of the hydrogens of the —O—CH$_2$—O— group may be replaced by a methyl; and R$^{13}$ is selected from halo, trihalomethyl, and C$_{1-4}$alkoxy; or a pharmaceutically acceptable salt or in-vivo hydrolysable ester thereof.

3. A compound of claim 1, wherein

R$^2$ and R$^3$ are independently selected from hydrogen, C$_{1-4}$alkyl [optionally substituted with 1 or 2 R$^8$ groups], —COR$^8$, and —SO$_b$R$^8$ (wherein b is 0, 1, or 2);

R$^8$ is independently selected from hydrogen, hydroxy, C$_{1-4}$alkoxy, C$_{1-4}$alkoxyC$_{1-4}$alkyl, C$_{1-4}$alkyl, amino (C$_{1-4}$)alkyl [optionally substituted on nitrogen with 1 or 2 groups selected from C$_{1-4}$alkyl, hydroxy(C$_{1-4}$)alkyl, dihydroxy(C$_{1-4}$)alkyl, —CO$_2$C$_{1-4}$alkyl, phenyl, and aryl(C$_{1-4}$)alkyl], C$_{2-4}$alkenyl, C$_{3-7}$cycloalkyl (optionally substituted with —C(O)OC$_{1-4}$alkyl), 5- and 6-membered cyclic acetals and mono- and di-methyl derivatives thereof, halo(C$_{1-4}$)alkyl, trihalo(C$_{1-4}$)alkyl, hydroxy(C$_{1-4}$)alkyl, dihydroxy(C$_{1-4}$)alkyl, cyano(C$_{1-4}$) alkyl, furyl (optionally substituted on carbon with 1 or 2 nitro groups), thienyl (optionally substituted on carbon with 1 or 2 nitro groups), morpholino, furyl(C$_{1-4}$) alkyl (wherein furyl is optionally substituted on carbon with 1 or 2 nitro groups), thienyl($C_{1-4}$)alkyl (wherein thienyl is optionally substituted on carbon with 1 or 2 nitro groups), 1,2,4-oxadiazolyl, tetrazolyl, imidazolyl, pyrrolidinyl, piperidyl, pyridyl, tetrahydrofuryl, tetrahydropyranyl, 1-oxo-tetrahydrothiopyranyl, tetrahydrothienyl, phenyl (optionally substituted with 1 or 2 groups selected from nitro, halo, cyano, hydroxy, and $C_{1-4}$alkyl), pyrazinyl, piperazinyl, 4-methylpiperazino, $C_{1-4}$alkylS(O)$_b$— (wherein b is 0, 1, or 2), $C_{3-6}$cycloalkylS(O)$_b$— (wherein b is 0, 1, or 2), arylS(O)$_b$— (wherein b is 0, 1, or 2), heterocyclylS(O)$_b$— (wherein b is 0, 1, or 2 —CH$_2$CH(NR$^9$R$^{10}$)CO(NR$^{9'}$R$^{10'}$), —CH$_2$OR$^9$, (R$^9$)(R$^{10}$)N—, —COOR$^9$, —CH$_2$COOR$^9$, —C(O)N(R$^9$)(R$^{10}$), —CH$_2$CH(CO$_2$R$^9$)OH, —CH$_2$CONR$^9$R$^{10}$, —CH$_2$CH(NR$^9$R$^{10'}$)CO$_2$R$^{9'}$, and —CH$_2$OCOR$^9$; and R$^9$, R$^{9'}$, R$^{10}$ and R$^{10'}$ are independently selected from hydrogen, $C_{1-4}$alkyl (optionally substituted with 1 or 2 hydroxy groups), $C_{2-4}$alkenyl, and phenyl (optionally substituted with 1 or 2 groups selected from nitro, halo, hydroxy, and cyano);

or a pharmaceutically acceptable salt or in-vivo hydrolysable ester thereof.

4. A compound of claim 1, wherein Y is NR$^2$R$^3$, or a pharmaceutically acceptable salt or in-vivo hydrolysable ester thereof.

5. A compound of claim 1, wherein Y is OR$^3$, or a pharmaceutically acceptable salt or in-vivo hydrolysable ester thereof.

6. A compound of claim 1, wherein R$^4$ and R$^5$ together are —S—C(R$^6$)=C(R$^7$)—, or a pharmaceutically acceptable salt or in-vivo hydrolysable ester thereof.

7. A compound of claim 1, wherein R$^4$ and R$^5$ together are —C(R$^7$)=C(R$^6$)—S—, or a pharmaceutically acceptable salt or in-vivo hydrolysable ester thereof.

8. A compound of claim 1, wherein A is phenylene, or a pharmaceutically acceptable salt or in-vivo hydrolysable ester thereof.

9. A compound of claim 1, wherein A is heteroarylene, or a pharmaceutically acceptable salt or in-vivo hydrolysable ester thereof.

10. A compound of claim 1, wherein Z is CH, or a pharmaceutically acceptable salt or in-vivo hydrolysable ester thereof.

11. A compound of claim 1, which is a compound of formula (1B)

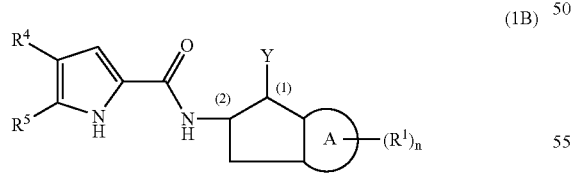

(1B)

or a pharmaceutically acceptable salt or an in-vivo hydrolysable ester thereof.

12. A compound of claim 1, selected from 2,3-dichloro-N-[(1R,2R)-1-(formylamino)-2,3-dihydro-1H-inden-2-yl]-4H-thieno[3,2-b]pyrrole-5-carboxamide;

2,3-dichloro-N-((1R,2R)-1-{[(methyloxy)acetyl]amino}-2,3-dihydro-1H-inden-2-yl)-4H-thieno[3,2-b]pyrrole-5-carboxamide;

N-((1S,2S)-1-{[(3R)-3-(tert-butoxycarbonylamino)-3-carbamoylpropanoyl]amino}-2,3-dihydro-1H-inden-2-yl)-2,3-dichloro-4H-thieno[3,2-b]pyrrole-5-carboxamide;

2,3-dichloro-N-[(1R,2R)-1-({[(4R)-2,2-dimethyl-5-oxo-1,3-dioxolan-4-yl]acetyl}amino)-2,3-dihydro-1H-inden-2-yl]-4H-thieno[3,2-b]pyrrole-5-carboxamide;

2,3-dichloro-N-{(1R,2R)-1-[(3-methoxypropanoyl)amino]-2,3-dihydro-1H-inden-2-yl}-4H-thieno[3,2-b]pyrrole-5-carboxamide;

N-{(1R,2R)-1-[(2-acetoxyacetyl)amino]-2,3-dihydro-1H-inden-2-yl}-2,3-dichloro-4H-thieno[3,2-b]pyrrole-5-carboxamide;

N-{(1R,2R)-1-[(2-carbamoylacetyl)amino]-2,3-dihydro-1H-inden-2-yl}-2,3-dichloro-4H-thieno[3,2-b]pyrrol-5-carboxamide;

2,3-dichloro-N-{(1R,2R)-1-[(trifluoroacetyl)amino]-2,3-dihydro-1H-inden-2-yl}-4H-thieno[3,2-b]pyrrole-5-carboxamide;

2,3-dichloro-N-{(1S,2S)-1-[(furan-2-ylcarbonyl)amino]-2,3-dihydro-1H-inden-2-yl}-4H-thieno[3,2-b]pyrrole-5-carboxamide;

2,3-dichloro-N-{(1S,2S)-1-[(furan-3-ylcarbonyl)amino]-2,3-dihydro-1H-inden-2-yl}-4H-thieno[3,2-b]pyrrole-5-carboxamide;

2,3-dichloro-N-{(1S,2S)-1-[(3-thienylcarbonyl)amino]-2,3-dihydro-1H-inden-2-yl}-4H-thieno[3,2-b]pyrrole-5-carboxamide;

2,3-dichloro-N-((1S,2S)-1-{[(5-nitrofuran-2-yl)carbonyl]amino}-2,3-dihydro-1H-inden-2-yl)-4H-thieno[3,2-b]pyrrole-5-carboxamide;

2,3-dichloro-N-{(1S,2S)-1-[(pyridin-3-ylcarbonyl)amino]-2,3-dihydro-1H-inden-2-yl}-4H-thieno[3,2-b]pyrrole-5-carboxamide;

N-[(1S,2S)-1-(acryloylamino)-2,3-dihydro-1H-inden-2-yl]-2,3-dichloro-4H-thieno3,2-b]pyrrole-5-carboxamide;

2,3-dichloro-N-((1S,2S)-1-{[(3-hydroxyphenyl)carbonyl]amino}-2,3-dihydro-1H-inden-2-yl)-4H-thieno[3,2-b]pyrrole-5-carboxamide;

N-[(1S,2S)-1-(acetylamino)-2,3-dihydro-1H-inden-2-yl]-2,3-dichloro-4H-thieno[3,2-b]pyrrole-5-carboxamide;

N-[(1S,2S)-1-[(2-carboxyacetyl)amino]-2,3-dihydro-1H-inden-2-yl]-2,3-dichloro-4H-thieno[3,2-b]pyrrole-5-carboxamide;

2,3-dichloro-N-((1S,2S)-1-{[(dimethylamino)carbonyl]amino}-2,3-dihydro-1H-inden-2-yl)-4H-thieno[3,2-b]pyrrole-5-carboxamide;

2,3-dichloro-N-((1S,2S)-1-{[(4-methylpiperazin-1-yl)carbonyl]amino}-2,3-dihydro-1H-inden-2yl)-4H-thieno[3,2-b]pyrrole-5-carboxamide;

2,3-dichloro-N-((1S,2S)-1-{[(ethylamino)carbonyl]amino}-2,3-dihydro-1H-inden-2-yl)-4H-thieno[3,2-b]pyrrole-5-carboxamide;

2,3-dichloro-N-((1S,2S)-1-{[(prop-2-en-1-ylamino)carbonyl]amino}-2,3-dihydro-1H-inden-2-yl)-4H-thieno[3,2-b]pyrrole-5-carboxamide;

2,3-dichloro-N-[(1S,2S)-1-({[(3,5-dinitrophenyl)amino]carbonyl}amino)-2,3-dihydro-1H-inden-2-yl]-4H-thieno[3,2-b]pyrrole-5-carboxamide;

2,3-dichloro-N-[(1S,2S)-1-(formylamino)-2,3-dihydro-1H-inden-2-yl]-4H-thieno[3,2-b]pyrrole-5-carboxamide;

N-{(1R,2R)-1-[((3R)-3-amino-3-carbamoylpropanoyl)amino]-2,3-dihydro-1H-inden-2-yl}-2,3-dichloro-4H-thieno[3,2-b]pyrrole-5-carboxamide;

N-{(1R,2R)-1-[((3R)-3-carboxy-3-hydroxypropanoyl)amino]-2,3-dihydro-1H-inden-2-yl}-2,3-dichloro-4H-thieno[3,2-b]pyrrole-5-carboxamide;

2,3-dichloro-N-{(1R,2R)-1-[(hydroxyacetyl)amino]-2,3-dihydro-1H-inden-2-yl}-4H-thieno[3,2-b]pyrrole-5-carboxamide;

2,3-dichloro-N-{(1S,2S)-1-[(methylsulfonyl)amino]-2,3-dihydro-1H-inden-2-yl}-4H-thieno[3,2-b]pyrrole-5-carboxamide;

2,3-dichloro-N-{(1S,2S)-1-[methyl(morpholin-4-ylacetyl)amino]-2,3-dihydro-1H-inden-2-yl}-4H-thieno[3,2-b]pyrrole-5-carboxamide;

N-{(1R,2R)-1-[(2-amino-2-oxoethyl)amino]-2,3-dihydro-1H-inden-2-yl}-2,3-dichloro-4H-thieno[3,2-b]pyrrole-5-carboxamide;

N-{(1R,2R)-1-[(tert-butoxycarbonylmethyl)amino]-2,3-dihydro-1H-inden-2-yl}-2,3-dichloro-4H-thieno[3,2-b]pyrrole-5-carboxamide;

N-[(1R,2R)-1-(carboxymethylamino)-2,3-dihydro-1H-inden-2-yl]-2,3-dichloro-4H-thieno[3,2-b]pyrrole-5-carboxamide;

N-{(1R,2R)-1-[N-acetyl-N-(carboxymethyl)amino]-2,3-dihydro-1H-inden-2-yl}-2,3-dichloro-4H-thieno[3,2-b]pyrrole-5-carboxamide;

N-{(1R,2R)-1-[acetyl(2-amino-2-oxoethyl)amino]-2,3-dihydro-1H-inden-2-yl}-2,3-dichloro-4H-thieno[3,2-b]pyrrole-5-carboxamide;

N-{(1R,2R)-1-[N-(carboxymethyl)-N-(hydroxyacetyl)amino]-2,3-dihydro-1H-inden-2-yl}-2,3-dichloro-4H-thieno[3,2-b]pyrrole-5-carboxamide;

2-chloro-N-[(1R,2R)-1-({[(2S)-5-oxotetrahydrofuran-2-yl]carbonyl}amino)-2,3-dihydro-1H-inden-2-yl]-6H-thieno[2,3-b]pyrrole-5-carboxamide;

2-chloro-N-[(1R,2R)-1-(formylamino)-2,3-dihydro-1H-inden-2-yl]-6H-thieno[2,3-b]pyrrole-5-carboxamide;

2-chloro-N-{(1R,2R)-1-[(methoxyacetyl)amino]-2,3-dihydro-1H-inden-2-yl}-6H-thieno[2,3-b]pyrrole-5-carboxamide;

N-[(1R,2R)-1-(acetylamino)-2,3-dihydro-1H-inden-2-yl]-2-chloro-6H-thieno[2,3-b]pyrrole-5-carboxamide;

2-chloro-N-{(1R,2R)-1-[(3-methoxypropanoyl)amino]-2,3-dihydro-1H-inden-2-yl}-6H-thieno[2,3-b]pyrrole-5-carboxamide;

N-{(1R,2R)-1-[(2-acetoxyaoetyl)amino]-2,3-dihydro-1H-inden-2-yl}-2-chloro-6H-thieno[2,3-b]pyrrole-5-carboxamide;

N-((1R,2R)-1-{[(3R)-3-(tert-butoxyoarbonylamino)-3-carbamoylpropanoyl]amino}-2,3-dihydro-1H-inden-2-yl)-2-chloro-6H-thieno[2,3-b]pyrrole-5-carboxamide;

N-{(1R,2R)-1-[2-(tert-butoxycarbonylamino)acetylamino]-2,3-dihydro-1H-inden-2-yl}-2-chloro-6H-thieno[2,3-b]pyrrole-5-carboxamide;

N-{(1R,2R)-1-[(2-carbamoylacetyl)amino]-2,3-dihydro-1H-inden-2-yl}-2-chloro-6H-thieno[2,3-b]pyrrole-5-carboxamide;

N-{(1R,2R)-1-[2-(tert-butoxycarbonyl)acetylamino]-2,3-dihydro-1H-inden-2-yl}-2-chloro-6H-thieno[2,3-b]pyrrole-5-carboxamide;

2-chloro-N-((1R,2R)-1-{[3-hydroxy-2-(hydroxymethyl)propanoyl]amino}-2,3-dihydro-1H-inden-2-yl)-6H-thieno[2,3-b]pyrrole-5-carboxamide;

N-{(1R,2R)-1-[((3R)-3-amino-3-carbamoylpropanoyl)amino]-2,3-dihydro-1H-inden-2-yl}-2-chloro-6H-thieno[2,3-b]pyrrole-5-carbaxamide;

N-{(1R,2R)-1-[(aminoacetyl)amino]-2,3-dihydro-1H-inden-2-yl}-2-chloro-6H-thieno[2,3-b]pyrrole-5-carboxamide;

2-chloro-N-[(1R,2R)-1-({[(2-hydroxyethyl)(phenylmethyl)amino]acetyl}amino)-2,3-dihydro-1H-inden-2-yl]-6H-thieno[2,3-b]pyrrole-5-carboxamide;

2-chloro-N-{(1R,2R)-1-[(morpholin-4-ylacetyl)amino]-2,3-dihydro-1H-inden-2-yl}-6H-thieno[2,3-b]pyrrole-5-carboxamide;

2-chloro-N-((1R,2R)-1-({[(2-hydroxyethyl)(methyl)amino]acetyl}amino)-2,3-dihydro-1H-inden-2-yl)-6H-thieno[2,3-b]pyrrole-5-carboxamide;

N-((1R,2R)-1-({[bis(2-hydroxyethyl)amino]acetyl}amino)-2,3-dihydro-1H-inden-2-yl)-2-chloro-6H-thieno[2,3-b]pyrrole-5-carboxamide;

2-chloro-N-((1R,2R)-1-({[ethyl (2-hydroxyethyl)amino]acetyl}amino)-2,3-dihydro-1H-inden-2-yl)-6H-thieno[2,3-b]pyrrole-5-carboxamide;

2-chloro-N-((1R,2R)-1-({[(2,3-dihydroxypropyl)(methyl)amino]acetyl}amino)-2,3-dihydro-1H-inden-2-yl)-6H-thieno[2,3-b]pyrrole-5-carboxamide;

N-((1R,2R)-1-({[bis(2-hydroxypropyl)amino]acetyl}amino)-2,3-dihydro-1H-inden-2-yl) -2-chloro-6H-thieno[2,3-b]pyrrole-5-carboxamide;

N-{(1R,2R)-1-[(2-amino-2-oxoethyl)amino]-2,3-dihydro-1H-inden-2-yl}-2-chloro-6H-thieno[2,3-b]pyrrole-5-carboxamide;

N-{(1R,2R)-1-[(tert-butoxycarbonylmethyl)amino]-2,3-dihydro-1H-inden-2-yl}-2-chloro-6H-thieno[2,3-b]pyrrole-5-carboxamide;

N-{(1R,2R)-1-(carboxymethylamino)-2,3-dihydro-1H-inden-2-yl}-2-chloro-6H-thieno [3,2-b]pyrrole-5-carboxamide;

2-chloro-N-{(1R,2R)-1-[(hydroxyacetyl)amino]-2,3-dihydro-1H-inden-2-yl}-6H-thieno[2,3-b]pyrrole-5-carboxamide;

2,3-dichloro-N-{(1R,2R)-1-[(chloroacetyl)amino]-2,3-dihydro-1H-inden-2-yl}-4H-thieno[3,2-b]pyrrole-5-carboxamide;

N-{(1R,2R)-1-[((3S)-3-amino-3-carboxypropanoyl)amino]-2,3-dihydro-1H-iden-2-yl}-2,3-dichloro-4H-thieno[3,2-b]pyrrole-5-carboxamide;

N-{(1R,2R)-1-[(2-carboxyacetyl)amino]-2,3-dihydro-1H-inden-2-yl}-2,3-dichloro-4H-thieno[3,2-b]pyrrole-5-carboxamide;

N-{(1R,2R)-1-[(2-carboxyacetyl)amino]-2,3-dihydro-1H-inden-2-yl}-2-chloro-6H-thieno[3,2-b]pyrrole-5-carboxamide;

N-{(1R,2R)-1-[((3S)-3-amino-3-carboxypropanoyl)amino]-2,3-dihydro-1H-inden-2-yl}-2-chloro-6H-thieno[3,2-b]pyrrole-5-carboxamide; and 2,3-dichloro-N-{(1R,2R)-1-[(methylsulfonyl)amino]-2,3-dihydro-1H-inden-2-yl}-4H-thieno[3,2-b]pyrrole-5-carboxamide;

or a pharmaceutically acceptable salt or an in-vivo hydrolysable ester thereof.

13. A pharmaceutical composition which comprises a compound claim 1 or a pharmaceutically acceptable salt or in-vivo hydrolysable ester thereof, in association with a pharmaceutically acceptable diluent or carrier.

14. A method for the treatment of type 2 diabetes in a warm-blooded animal, comprising administering a compound of claim 1, or a pharmaceutically acceptable salt or in-vivo hydrolysable ester thereof.

15. A process for the preparation of claim 1, which process comprises:

reacting an acid of the formula (2)

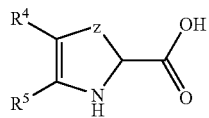
(2)

or an activated derivative thereof; with an amine of formula (3)

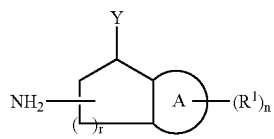
(3)

and thereafter if necessary i) converting a compound of the formula (1) into another compound of the formula (1);
ii) removing any protecting groups; or
iii) forming a pharmaceutically acceptable salt or in-vivo hydrolysable ester.

16. A compound of claim 1, selected from:
N-[(1R,2R)-1-amino-2,3-dihydro-1H-inden-2-yl]-2-chloro-6H-thieno[2,3-b]pyrrole-5-carboxamide; and
tert-butyl ((1R,2R)-2-{[(2-chloro-6H-thieno[2,3-b]pyrrol-5-yl)carbonyl]amino}-2,3-dihydro-1H-inden-1-yl)carbamate.

* * * * *